US011186848B2

(12) United States Patent
Prasad et al.

(10) Patent No.: US 11,186,848 B2
(45) Date of Patent: Nov. 30, 2021

(54) NON-HUMAN ANIMALS EXPRESSING HUMANIZED C1Q COMPLEX

(71) Applicant: Regeneron Pharmaceuticals, Inc., Tarrytown, NY (US)

(72) Inventors: Brinda Prasad, Long Island City, NY (US); Naxin Tu, Pleasantville, NY (US); Karolina Meagher, Yorktown Heights, NY (US); Lynn Macdonald, Harrison, NY (US); Andrew Murphy, Croton-on-Hudson, NY (US); Sean Stevens, Del Mar, CA (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 281 days.

(21) Appl. No.: 16/144,156

(22) Filed: Sep. 27, 2018

(65) Prior Publication Data

US 2019/0100772 A1    Apr. 4, 2019

Related U.S. Application Data

(60) Provisional application No. 62/565,438, filed on Sep. 29, 2017.

(51) Int. Cl.
*A01K 67/027* (2006.01)
*C12N 15/85* (2006.01)
*C07K 14/47* (2006.01)

(52) U.S. Cl.
CPC ...... *C12N 15/8509* (2013.01); *A01K 67/0278* (2013.01); *C07K 14/472* (2013.01); *A01K 2207/15* (2013.01); *A01K 2217/054* (2013.01); *A01K 2217/072* (2013.01); *A01K 2217/15* (2013.01); *A01K 2227/105* (2013.01); *A01K 2267/0337* (2013.01); *A01K 2267/0368* (2013.01); *A01K 2267/0387* (2013.01); *C12N 2015/8527* (2013.01)

(58) Field of Classification Search
CPC ................ A01K 67/0278; A01K 2207/15
See application file for complete search history.

(56) References Cited

U.S. PATENT DOCUMENTS

| | | | |
|---|---|---|---|
| 6,586,251 | B2 | 7/2003 | Economides et al. |
| 7,294,754 | B2 | 11/2007 | Poueymirou et al. |
| 7,576,259 | B2 | 8/2009 | Poueymirou et al. |
| 7,659,442 | B2 | 2/2010 | Poueymirou et al. |
| 2007/0264689 | A1 | 11/2007 | Gross et al. |
| 2008/0078000 | A1 | 3/2008 | Poueymirou et al. |
| 2014/0235933 | A1 | 8/2014 | Lee et al. |
| 2014/0310828 | A1 | 10/2014 | Lee et al. |
| 2017/0164588 | A1 | 6/2017 | Olson et al. |
| 2017/0190794 | A1 | 7/2017 | Green et al. |
| 2017/0190797 | A1 | 7/2017 | Green et al. |
| 2019/0098879 | A1 | 4/2019 | Drummond-Samuelson et al. |

FOREIGN PATENT DOCUMENTS

| | | |
|---|---|---|
| AU | 2004278556 A1 | 4/2005 |
| CN | 106659146 A | 5/2017 |
| CN | 107105633 A | 8/2017 |
| JP | 2017-143840 A | 8/2017 |
| WO | 2015/171523 A1 | 11/2015 |

OTHER PUBLICATIONS

Harari D. et al., "Bridging the Species Divide: Transgenic Mice Humanized for Type-I Interferon Response", PLoS ONE 9(1):e84259, XP055553720, DOI:10.1371/journal.pone.0084259 (Jan. 9, 2014).
Kishore U. et al., "Structural and Functional Anatomy of the Globular Domain of Complement Protein C1q", Immunol Lett. 95(2):113-128 (Sep. 1, 2004).
Kouser L. et al., "Emerging and Novel Functions of Complement Protein C1q", Frontiers in Immunology 6:317 (Jun. 29, 2015).
Li Q-X et al., "Experimental Animal Modeling for Immuno-Oncology", Pharmacology & Therapeutics 173:34-46 (May 1, 2017).
Li J. et al., "C1 Complex: An Adaptable Proteolytic Module for Complement and Non-Complement Functions", Frontiers in Immunology 8:592 (May 24, 2017).
Li M. et al., "Development of a Humanized C1qA A Chain Knock-In Mouse: Assessment of Antibody Independent β-Amyloid Induced Complement Activation", Molecular Immunology 45(11 ):3244-3252 (Jun. 1, 2008).
Phuan P-W et al., "C1q-Targeted Monoclonal Antibody Prevents Complement-Dependent Cytotoxicity and Neuropathology in In Vitro and Mouse Models of Neuromyelitis Optica", Acta Neuropathol 125(6):829-840 (Jun. 1, 2013).
Sontheimer R.D. et al., "C1q: Its Functions Within the Innate and Adaptive Immune Responses and its Role in Lupus Autoimmunity", Journal of Investigative Dermatology 125(1):14-23 (Jul. 1, 2005).
Database UniProt No. XP-002787214, dated Nov. 16, 2011 (2 pages).
International Search Report and Written Opinion dated Jan. 23, 2019 received in International Application No. PCT/US2018/053099.
Beinrohr L. et al., "C1, MBL-MASPs and C1-Inhibitor: Novel Approaches for Targeting Complement-Mediated Inflammation", Trends in Molecular Medicine 14(12):511-521 (Nov. 2008).
Bobak D.A. et al., "Modulation of FcR Function by Complement: Subcomponent C1q Enhances the Phagocytosis of IgG-Opsonized Targets by Human Monocytes and Culture-Derived Macrophages", The Journal of Immunology 138(4):1150-1156 (Feb. 15, 1987).
Bohlson S.S. et al., "Complement Proteins C1q and MBL are Pattern Recognition Molecules that Signal Immediate and Long-Term Protective Immune Functions", Molecular Immunology 44:33-43 (2007).
Castellano G. et al., "Maturation of Dendritic Cells Abrogates C1q Production In Vivo and In Vitro", Blood 103(10):3813-3820 (May 15, 2004).

(Continued)

Primary Examiner — Valarie E Bertoglio
(74) Attorney, Agent, or Firm — Scully, Scott, Murphy & Presser, P.C.; Eileen Woo

(57) ABSTRACT

Disclosed herein are nucleic acids encoding for and proteins expressing chimeric C1q polypeptides, non-human animals comprising said nucleic acids, and methods of making or using said non-human animals.

25 Claims, 13 Drawing Sheets
Specification includes a Sequence Listing.

(56) References Cited

OTHER PUBLICATIONS

Diebolder C.A. et al., "Complement is Activated by IgG Hexamers Assembled at the Cell Surface", Science 1260-1263 (Mar. 14, 2014).
Dillon S.P. et al., "SLE and C1q: A Quantitative ELISA for Determining C1q Levels in Serum", Biotechnol J. 4(8):1210-1214 (Aug. 2009).
Dunkelberger J.R. et al., "Complement and its Role in Innate and Adaptive Immune Responses", Cell Research 20:34-50 (2010).
Flieger D. et al., "Mechanism of Cytotoxicity Induced by Chimeric Mouse Human Monoclonal Antibody IDEC-C2B8 in CD20-Expressing Lymphoma Cell Lines", Cellular Immunology 204:55-63 (2000).
Ghai R. et al., "C1q and its Growing Family", Immunobiology 212:253-266 (2007).
Glennie M.J. et al., "Mechanisms of Killing by Anti-CD20 Monoclonal Antibodies", Molecular Immunology 44:3823-3837 (2007).
Hosszu K.K. et al., "DC-SIGN, C1q, and gC1qR Form a Trimolecular Receptor Complex on the Surface of Monocyte-Derived Immature Dendritic Cells", Blood 120(6):1228-1236 (Aug. 9, 2012).
Lu J. et al., "The Classical and Regulatory Functions of C1q in Immunity and Autoimmunity", Cellular & Molecular Immunology 5(1):9-21 (Feb. 2008).
O'Keefee K.M. et al., "Manipulation of Autophagy in Phagocytes Facilitates *Staphylococcus aureus* Bloodstream Infection", Infection and Immunity 83(9):3445-3457 (Sep. 2015).
Petry F. et al., "The Mouse C1q Genes are Clustered on Chromosome 4 and Show Conservation of Gene Organization", Immunogenetics 43:370-376 (1996).
Poueymirou W.T. et al., "F0 Generation Mice Fully Derived from Gene-Targeted Embryonic Stem Cells Allowing Immediate Phenotypic Analyses", Nature Biotechnology 25(1):91-99 (Jan. 2007).
Rauch S. et al., "Abscess Formation and Alpha-Hemolysin Induced Toxicity in a Mouse Model of *Staphylococcus aureus* Peritoneal Infection", Infection and Immunity 80(10):3721-3732 (Oct. 2012).
Reid K.B.M., "Proteins Involved in the Activation and Control of the Two Pathways of Human Complement", Biochemical Society Transactions 11:1-12 (1983).
Sato F. et al., "A Complement-Dependent Cytotoxicity-Enhancing Anti-CD20 Antibody Mediating Potent Antitumor Activity in the Humanized NOD/Shi-scid, IL-2Rynull Mouse Lymphoma Model", Cancer Immunol Immunother 59:1791-1800 (2010).
Thammavongsa V. et al., "*Staphylococcus aureus* Synthesizes Adenosine to Escape Host Immune Responses", J. Exp. Med. 206(11):2417-2427 (Oct. 26, 2009).
Tong C. et al., "Generating Gene Knockout Rats by Homologous Recombination in Embryonic Stem Cells", Nat Protoc. 6(6):doi:10.1038/nprot.2011.338 (Jun. 2011).
Tong C. et al., "Production of p53 Gene Knockout Rats by Homologous Recombination in Embryonic Stem Cells", Nature 467:211-213 (Sep. 9, 2010).
Valenzuela D.M. et al., "High-Throughput Engineering of the Mouse Genome Coupled With High-Resolution Expression Analysis", Nature Biotechnology 21(6):652-659 (Jun. 2003).
Yonemasu K. et al., "Complement Subcomponent C1q in Various Strains of Mice", Int. Archs Allergy Appl. Immun. 86:97-101 (1988).
NCBI Reference Sequence No. NC_005104.4 (3 pages) (Jul. 27, 2016).
NCBI Reference Sequence No. NC_000070.6 (2 pages) (Jun. 22, 2016).
NCBI Reference Sequence No. NG_007565.1 (9 pages) (Jun. 3, 2018).
NCBI Reference Sequence No. NG_007282.1 (6 pages) (Dec. 15, 2017).
NCBI Reference Sequence No. NG_007283.1 (7 pages) (Dec. 14, 2017).
NCBI Reference Sequence No. NP_001334394.1 (5 pages) (Oct. 22, 2018).
NCBI Reference Sequence No. NP_001334548.1 (5 pages) (Oct. 22, 2018).
NCBI Reference Sequence No. NP_000482.3 (6 pages) (Oct. 22, 2018).
NCBI Reference Sequence No. NP_001008524.1 (4 pages) (Oct. 20, 2018).
NCBI Reference Sequence No. NP_062135.1 (5 pages) (Oct. 2, 2018).
NCBI Reference Sequence No. NP_033907.1 (5 pages) (Oct. 2, 2018).
NCBI Reference Sequence No. NP_031600.2 (4 pages) (Oct. 2, 2018).
NCBI Reference Sequence No. NP_001008515.1 (4 pages) (Oct. 2, 2018).
NCBI Reference Sequence No. NP_031598.2 (4 pages) (Oct. 2, 2018).
Chinese Office Action & Search Report dated Jul. 30, 2021 received in Chinese Application No. 20188066080.7, together with an English-language translation.

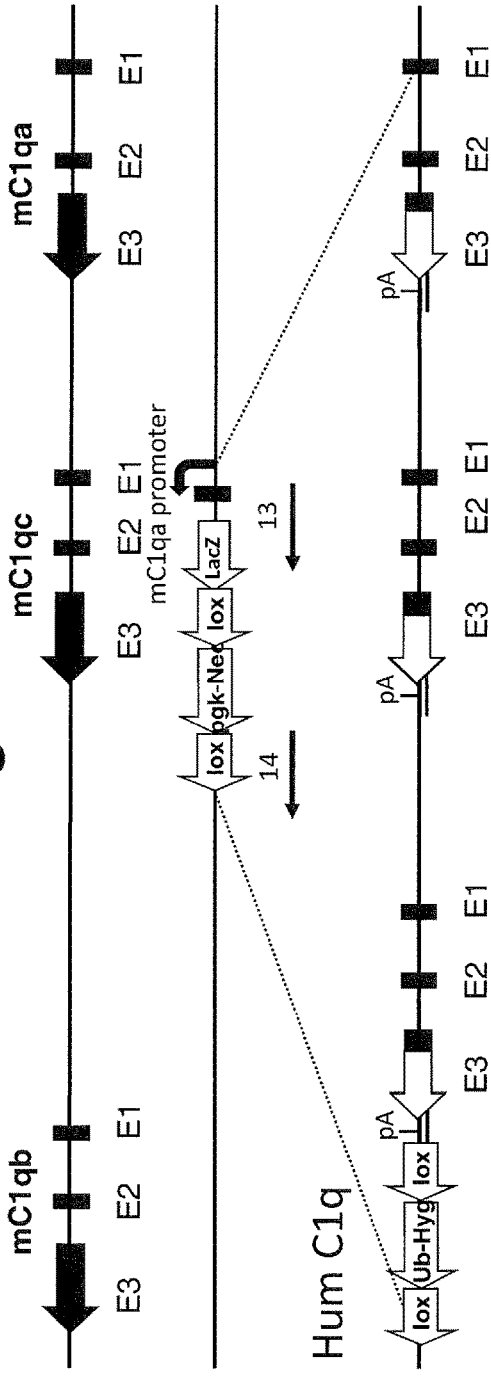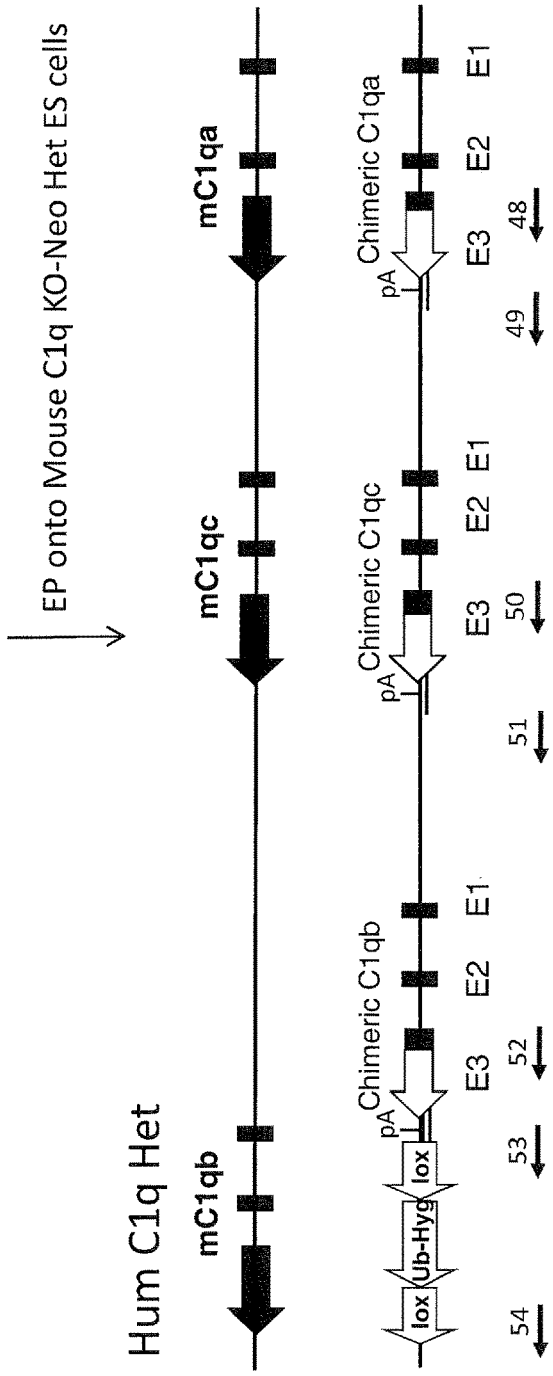
Figure 1C

C1Qa alignments

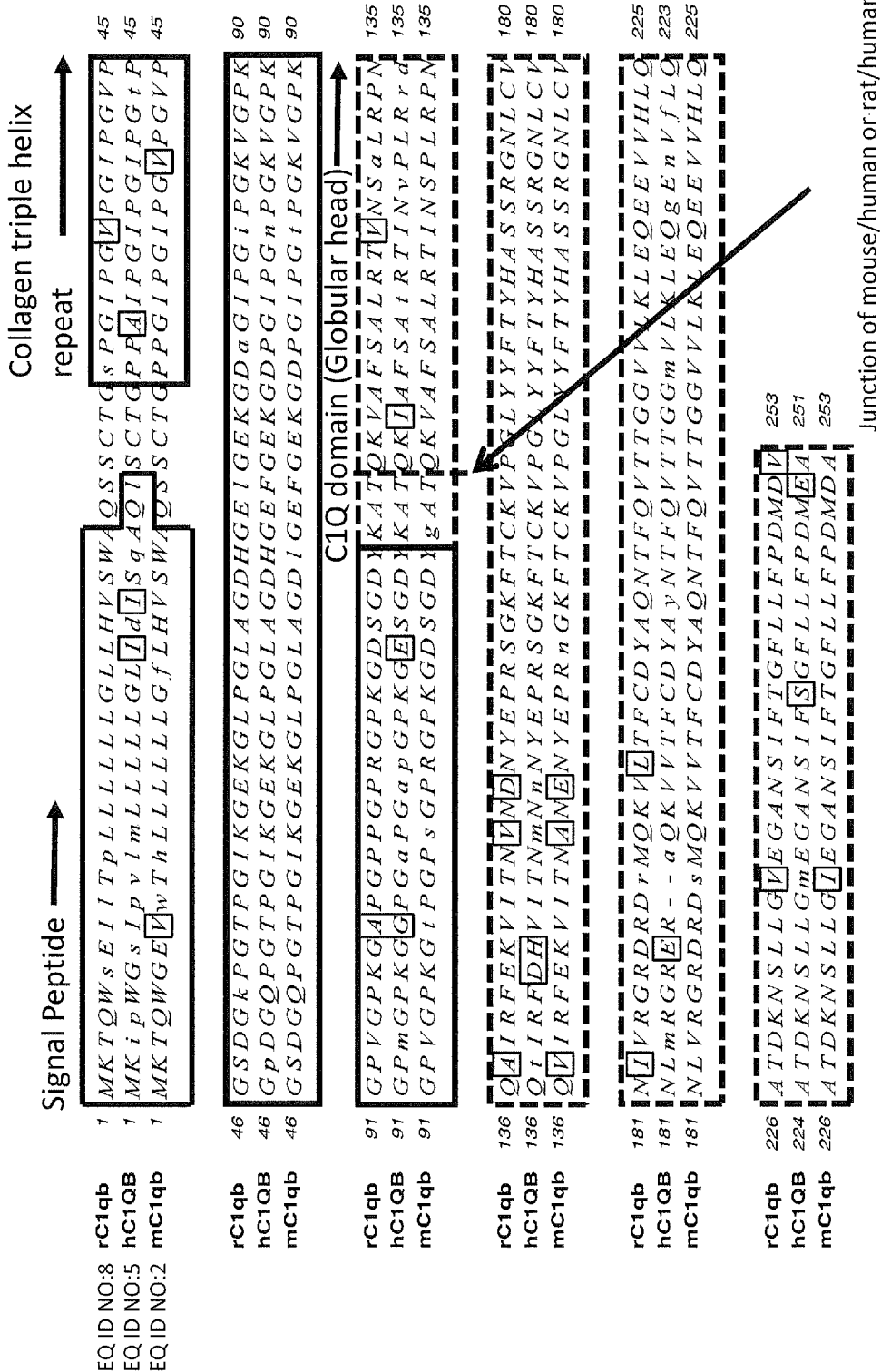

Figure 3C

C1Qc alignments

Signal Peptide →

| | | | |
|---|---|---|---|
| SEQ ID NO:9 | rC1qc | 1 | MLRMVVGtSCQPqhGLyLLLL-LLALPLRSQANAGCYGIPGMPGL 44 |
| SEQ ID NO:6 | hC1QC | 1 | MdVGPSslPhIGLkLLLL-LLLPLRgQANtGCYGIPGMPGL 41 |
| SEQ ID NO:3 | mC1qc | 1 | MVVGPSCQPpcGLcLLLLFLLALPLRSQAsAGCYGIPGMPGm 42 |

| | | |
|---|---|---|
| rC1qc | 45 | PGtPGKDGHDGLQGPKGEPGIPAIPGTgGPKGQKGEPGMPGHRGK 89 |
| hC1QC | 42 | PGAPGKDGyDGLpGPKGEPGIPALPGIRGPKGQKGEPGHpGK 86 |
| mC1qc | 43 | PGAPGKDGHDGLQGPKGEPGIPAVPGTRGPKGQKGEPGHRGK 87 |

| | | |
|---|---|---|
| rC1qc | 90 | NGPMGTSGsPGDPGPRGPPPGEEGRYKQKHQSVFTVTRQTaQY 134 |
| hC1QC | 87 | NGPMGppGmPGvPGPmGiPGEPGEEGRYKQKfQSVFTVTRQThQp 131 |
| mC1qc | 88 | NGPrGTSGIPGDPGPGvPGPPPGEPGvEGRYKQKHQSVFTVTRQTtQY 132 |

C1Q domain (Globular head)

← Junction of mouse/human or rat/human C1Qc

| | | |
|---|---|---|
| rC1qc | 135 | PAANGLVKFNSAITNPQGDYNTnTGKFTCKVPGLYYFVhHTSqTA 179 |
| hC1QC | 132 | PAPNsLIRFNaVLTNPQGDYdTSTGKFTCNVPGLYYFVYFVhaSHTA 176 |
| mC1qc | 133 | PeANALVRFNSVVTNPQGhYNpSTGKFTCePGLYYFVYyTSHTA 177 |

| | | |
|---|---|---|
| rC1qc | 180 | NLCVqLILNnAKVtSFCDHMSNSKQVSSGGVLLRLQRGDEVWLAV 224 |
| hC1QC | 177 | NLCVILyrsGVKVVTFCgHtSkITnQVnSGGVLLRQvGEEVWLAV 221 |
| mC1qc | 178 | NLCVhLnLNLARVASFCDHMfNSKQVSSGGVLLRLQRGDEVWLsV 222 |

| | | |
|---|---|---|
| rC1qc | 225 | NDYNGMVGiEGSDSVFSGFLLFPD 248 |
| hC1QC | 222 | NDYydMVGIqGSDSVFSGFLLFPD 245 |
| mC1qc | 223 | NDYNGMVGIEGSnSVFSGFLLFPD 246 |

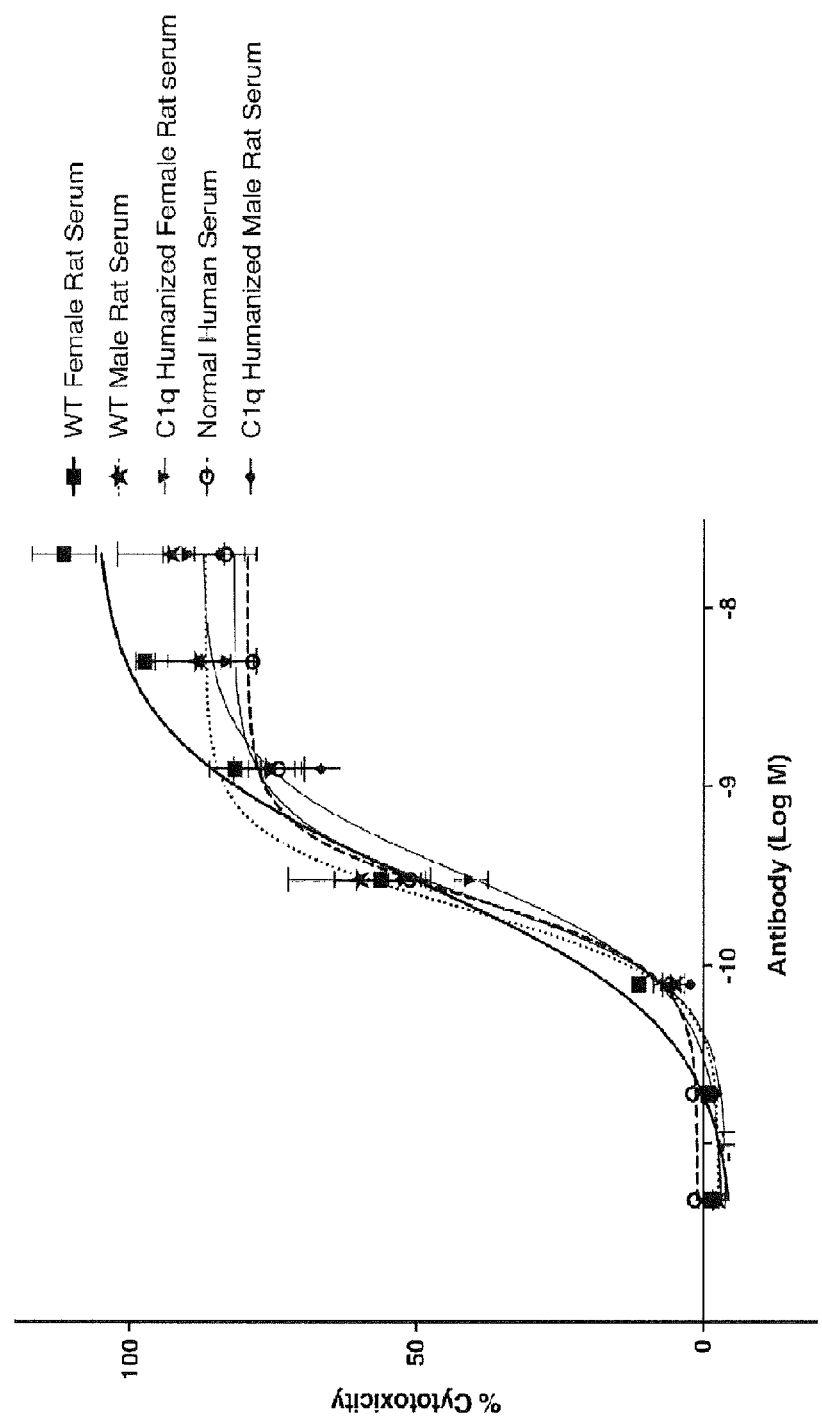

NON-HUMAN ANIMALS EXPRESSING HUMANIZED C1Q COMPLEX

CROSS REFERENCE TO RELATED APPLICATION

This application claims the benefit of priority from U.S. Provisional Application No. 62/565,438, filed Sep. 29, 2017, the contents of which are incorporated herein by reference in its entirety.

INCORPORATION BY REFERENCE OF SEQUENCE LISTING

The Sequence Listing in the ASCII text file, named as 35342_10353US01_SequenceListing.txt of 50 KB, created on Sep. 25, 2018 and submitted to the United States Patent and Trademark Office via EFS-Web, is incorporated herein by reference.

BACKGROUND

During preclinical drug development stage, candidate agents are typically studied based on their efficacy, toxicity, and other pharmacokinetic and pharmacodynamics properties. Candidate agents, such as antibodies, typically target a human antigen—as the end goal of investigation is to develop a human therapy. The ability to sequester the complement pathway provides a significant advantage to candidate therapeutic agents. The complement pathway is part of the innate immune response and assists humoral immune responses in the recruitment of marcrophage and phagocytes to the antigenic site. Activation of the complement pathway results in cytokine release and the opsonization of the antibody-bound antigen by phagocytes. During development of therapeutic agents that are aimed at activation of complement pathway and innate immune response in order to combat human disease, a model non-human animal system that would allow studies into the mechanisms of action and/or therapeutic potential of the agent is invaluable; but such system is lacking.

SUMMARY

Disclosed herein are chimeric mammalian C1q polypeptides (such as, for example chimeric mammalian C1qa, C1qb and/or C1qc polypeptides), nucleic acid molecules encoding chimeric mammalian C1q polypeptides, and non-human animals (e.g., mammals such as rodents) comprising said nucleic acid molecules and expressing chimeric C1q polypeptides.

In one aspect, disclosed herein is a genetically modified non-human animal comprising in its genome a nucleic acid encoding a chimeric C1q polypeptide (e.g., a chimeric C1qa polypeptide, a chimeric C1qb polypeptide, or a chimeric C1qc polypeptide), wherein the nucleic acid comprises a non-human nucleic acid sequence and a human nucleic acid sequence.

In some embodiments, the genetically modified non-human animal comprises in its genome more than one nucleic acid encoding a chimeric C1q polypeptide; for example, the non-human animal comprises in its genome a combination (e.g., two or all three) of a nucleic acid encoding a chimeric C1qa polypeptide, a nucleic acid encoding a chimeric C1qb polypeptide, and a nucleic acid encoding a chimeric C1qc polypeptide.

In some embodiments, the non-human animal is a mammal. In some embodiments, the non-human animal is a rodent, such as a rat or a mouse.

In some embodiments, the chimeric C1q polypeptide comprises a globular head domain that is substantially human (i.e., substantially identical to the globular head domain of a human C1q polypeptide), and an N-terminal stalk-stem region that is substantially non-human (i.e., substantially identical to the N-terminal stalk-stem region of a non-human C1q polypeptide such as an endogenous C1q polypeptide).

In some embodiments, the non-human animal comprises a nucleic acid encoding a chimeric C1q polypeptide that is a chimeric C1qa polypeptide. In some embodiments, the chimeric C1qa polypeptide comprises a globular head domain that is substantially identical to the globular head domain of a human C1qa polypeptide, and an N-terminal stalk-stem region that is substantially identical to the N-terminal stalk-stem region of a non-human C1qa polypeptide such as an endogenous C1qa polypeptide. In some embodiments, the globular head domain of a human C1qa polypeptide comprises amino acids 108-245 of SEQ ID NO: 4.

In some embodiments, the non-human animal is a mouse which comprises a nucleic acid encoding a chimeric C1qa polypeptide that comprises a globular head domain that is substantially identical to the globular head domain of a human C1qa polypeptide, and an N-terminal stalk-stem region that is substantially identical to the N-terminal stalk-stem region of a mouse C1qa polypeptide such as an endogenous mouse C1qa polypeptide. In certain embodiments, the N-terminal stalk-stem region of the endogenous mouse C1qa polypeptide comprises amino acids 23-107 of SEQ ID NO: 1. In specific embodiments, the chimeric C1qa polypeptide comprises amino acids 23-245 of SEQ ID NO: 10 (mouse/human). In specific embodiments, the chimeric C1qa polypeptide comprises the amino acid sequence of SEQ ID NO: 10 (mouse/human).

In some embodiments, the genetically modified non-human animal is a rat, which comprises a nucleic acid encoding a chimeric C1qa polypeptide that comprises a globular head domain that is substantially identical to the globular head domain of a human C1qa polypeptide, and an N-terminal stalk-stem region that is substantially identical to the N-terminal stalk-stem region of a rat C1qa polypeptide such as an endogenous rat C1qa polypeptide. In some embodiments, the N-terminal stalk-stem region of the endogenous rat C1qa polypeptide comprises amino acids 23-107 of SEQ ID NO: 7. In specific embodiments, the chimeric C1qa polypeptide comprises amino acids 23-245 of SEQ ID NO: 55 (rat/human). In specific embodiments, the chimeric C1qa polypeptide comprises the amino acid sequence of SEQ ID NO: 55 (rat/human).

In some embodiments, the non-human animal comprises a nucleic acid encoding a chimeric C1q polypeptide that is a chimeric C1qb polypeptide. In some embodiments, the chimeric C1qb polypeptide comprises a globular head domain that is substantially identical to the globular head domain of a human C1qb polypeptide, and an N-terminal stalk-stem region that is substantially identical to the N-terminal stalk-stem region of a non-human C1qb polypeptide such as an endogenous C1qb polypeptide. In some embodiments, the globular head domain of a human C1qb polypeptide comprises amino acids 115-251 of SEQ ID NO: 5.

In some embodiments, the non-human animal is a mouse, which comprises a nucleic acid encoding a chimeric C1qb polypeptide that comprises an N-terminal stalk-stem region that is substantially identical to the N-terminal stalk-stem region of a mouse C1qb polypeptide such as an endogenous mouse C1qb polypeptide. In some embodiments, the N-terminal stalk-stem region of the endogenous mouse C1qb polypeptide comprises amino acids 26-114 of SEQ ID NO: 2. In specific embodiments, the chimeric C1qb polypeptide comprises amino acids 26-251 of SEQ ID NO: 11 (mouse/human). In specific embodiments, the chimeric C1qb polypeptide comprises the amino acid sequence of SEQ ID NO: 11 (mouse/human).

In some embodiments, the non-human animal is a rat, which comprises a nucleic acid encoding a chimeric C1qb polypeptide that comprises an N-terminal stalk-stem region that is substantially identical to the N-terminal stalk-stem region of a rat C1qb polypeptide such as an endogenous rat C1qb polypeptide. In some embodiments, the N-terminal stalk-stem region of the endogenous rat C1qb polypeptide comprises amino acids 26-114 of SEQ ID NO: 8. In specific embodiments, the chimeric C1qb polypeptide comprises amino acids 26-251 of SEQ ID NO: 56 (rat/human). In specific embodiments, the chimeric C1qb polypeptide comprises the amino acid sequence of SEQ ID NO: 56 (rathuman).

In some embodiments, the non-human animal comprises a nucleic acid encoding a chimeric C1q polypeptide that is a chimeric C1qc polypeptide. In some embodiments, the chimeric C1qc polypeptide comprises a globular head domain that is substantially identical to the globular head domain of a human C1qc polypeptide, and an N-terminal stalk-stem region that is substantially identical to the N-terminal stalk-stem region of a non-human C1qc polypeptide such as an endogenous C1qc polypeptide. In some embodiments, the globular head domain of a human C1qc polypeptide comprises 113-245 of SEQ ID NO: 6.

In some embodiments, the non-human animal is a mouse which comprises a nucleic acid encoding a chimeric C1qc polypeptide that comprises a globular head domain that is substantially identical to the globular head domain of a human C1qc polypeptide, and an N-terminal stalk-stem region that is substantially identical to the N-terminal stalk-stem region of a mouse C1qc polypeptide such as an endogenous mouse C1qc polypeptide. In certain embodiments, the N-terminal stalk-stem region of the endogenous mouse C1qc polypeptide comprises amino acids 30-113 of SEQ ID NO: 3. In specific embodiments, the chimeric C1qc polypeptide comprises amino acids 30-246 of SEQ ID NO: 12 (mouse/human). In specific embodiments, the chimeric C1qc polypeptide comprises the amino acid sequence of SEQ ID NO: 12 (mouse/human).

In some embodiments, the genetically modified non-human animal is a rat, which comprises a nucleic acid encoding a chimeric C1qc polypeptide that comprises a globular head domain that is substantially identical to the globular head domain of a human C1qc polypeptide, and an N-terminal stalk-stem region that is substantially identical to the N-terminal stalk-stem region of a rat C1qc polypeptide such as an endogenous rat C1qc polypeptide. In some embodiments, the N-terminal stalk-stem region of the endogenous rat C1qc polypeptide comprises amino acids 32-115 of SEQ ID NO: 9. In specific embodiments, the chimeric C1qc polypeptide comprises amino acids 32-248 of SEQ ID NO: 57 (rat/human). In specific embodiments, the chimeric C1qc polypeptide comprises the amino acid sequence of SEQ ID NO: 57 (rat/human).

In some embodiments, a chimeric C1q polypeptide is translated in the non-human animal to contain a non-human C1q signal peptide such as an endogenous non-human C1q signal peptide. In other words, the nucleic acid molecule encoding a chimeric C1q polypeptide also comprises a coding sequence for a non-human C1q signal peptide such as an endogenous C1q signal peptide. For example, a nucleic acid molecule encoding a chimeric C1qa polypeptide also comprises a coding sequence for a non-human C1qa signal peptide such as an endogenous C1qa signal peptide; a nucleic acid molecule encoding a chimeric C1qb polypeptide also comprises a coding sequence for a non-human C1qb signal peptide such as an endogenous C1qb signal peptide; and a nucleic acid molecule encoding a chimeric C1qc polypeptide also comprises a coding sequence for a non-human C1qc signal peptide such as an endogenous C1qc signal peptide. Examples of mouse and rat C1q signal peptides are disclosed herein (see, e.g., in FIGS. 3A-3C).

In some embodiments, the nucleic acid encoding a chimeric C1q polypeptide is at a locus other than an endogenous non-human C1q locus. In other embodiments, the nucleic acid encoding a chimeric C1q polypeptide is at an endogenous non-human C1q locus. For example, a nucleic acid encoding a chimeric C1qa polypeptide is at an endogenous non-human C1qa locus; a nucleic acid encoding a chimeric C1qb polypeptide is at an endogenous non-human C1qb locus; and/or a nucleic acid encoding a chimeric C1qc polypeptide is at an endogenous non-human C1qc locus.

In embodiments where the nucleic acid encoding a chimeric C1q polypeptide is at an endogenous non-human C1q locus, in some such embodiments, an endogenous genomic sequence at the endogenous non-human C1q locus has been replaced by a human nucleic acid sequence. In some embodiments, the human nucleic acid sequence, such as a genomic fragment of a human C1q gene, encodes substantially the globular head domain of a human C1q polypeptide. In some embodiments, the human nucleic acid sequence also includes the 3' UTR of the human C1q gene (including the polyadenylation signal and the polyadenylation site of the human C1q gene).

In some embodiments, a genetically modified non-human animal comprises a nucleic acid encoding a chimeric C1qa polypeptide, wherein the nucleic acid comprises human and non-human nucleic acid sequences, and wherein the human nucleic acid sequence encodes substantially the globular head domain of a human C1qa polypeptide. In some embodiments, the globular head domain of the human C1qa polypeptide comprises amino acids 108-245 of SEQ ID NO: 4. In some embodiments, the human nucleic acid sequence encodes amino acids 112-245 of SEQ ID NO: 4.

In some embodiments, a genetically modified non-human animal comprises a nucleic acid encoding a chimeric C1qb polypeptide, wherein the nucleic acid comprises human and non-human nucleic acid sequences, and wherein the human nucleic acid sequence encodes substantially the globular head domain of a human C1qb polypeptide. In some embodiments, the globular head domain of the human C1qb polypeptide comprises amino acids 115-251 of SEQ ID NO: 5. In some embodiments, the human nucleic acid sequence encodes amino acids 118-251 of SEQ ID NO: 5.

In some embodiments, a genetically modified non-human animal comprises a nucleic acid encoding a chimeric C1qc polypeptide, wherein the nucleic acid comprises human and non-human nucleic acid sequences, and wherein the human nucleic acid sequence encodes substantially the globular head domain of a human C1qc polypeptide. In some embodiments, the globular head domain of the human C1qc polypeptide comprises amino acids 113-245 of SEQ ID NO: 6. In some embodiments, the human nucleic acid sequence encodes amino acids 114-245 of SEQ ID NO: 6.

In embodiments of a genetically modified non-human animal comprising a nucleic acid encoding a chimeric C1q polypeptide, wherein the nucleic acid comprises human and non-human nucleic acid sequences, the non-human nucleic acid sequences encode substantially the N-terminal stalk-stem region of a non-human C1q polypeptide such as an endogenous non-human C1q polypeptide. In embodiments where an endogenous genomic sequence at the endogenous non-human C1q locus has been replaced by a human nucleic acid sequence, in some such embodiments, the endogenous genomic sequence remaining at the C1q locus encodes substantially the N-terminal stalk-stem region of the endogenous C1q polypeptide.

In some embodiments, the non-human animal is a mouse, and the N-terminal stalk-stem region of an endogenous C1q polypeptide comprises amino acids 23-107 of SEQ ID NO: 1 (for C1qa), amino acids 26-114 of SEQ ID NO: 2 (for C1qb), or amino acids 30-113 of SEQ ID NO: 3 (for C1qc). In some embodiments, the mouse comprises a nucleic acid encoding a chimeric C1qa polypeptide, wherein the nucleic acid comprises a mouse nucleic acid sequence and a human nucleic acid sequence, and wherein the mouse nucleic acid sequence encodes amino acids 23-111 of SEQ ID NO: 1. In some embodiments, the mouse comprises a nucleic acid encoding a chimeric C1qb polypeptide, wherein the nucleic acid comprises a mouse nucleic acid sequence and a human nucleic acid sequence, and wherein the mouse nucleic acid sequence encodes amino acids 26-117 of SEQ ID NO: 2. In some embodiments, the mouse comprises a nucleic acid encoding a chimeric C1qc polypeptide, wherein the nucleic acid comprises a mouse nucleic acid sequence and a human nucleic acid sequence, wherein the mouse nucleic acid sequence encodes amino acids 30-114 of SEQ ID NO: 3.

In some embodiments, the non-human animal is a rat, and the N-terminal stalk-stem region of the endogenous C1q polypeptides comprises amino acids 23-107 of SEQ ID NO: 7 (for C1qa), amino acids 26-114 of SEQ ID NO: 8 (for C1qb), or amino acids 32-115 of SEQ ID NO: 9 (for C1qc). In some embodiments, the rat comprises a nucleic acid encoding a chimeric C1qa polypeptide, wherein the nucleic acid comprises a rat nucleic acid sequence and a human nucleic acid sequence, wherein the rat nucleic acid sequence encodes amino acids 23-111 of SEQ ID NO: 7. In some embodiments, the rat comprises a nucleic acid encoding a chimeric C1qb polypeptide, wherein the nucleic acid comprises a rat nucleic acid sequence and a human nucleic acid sequence, wherein the rat nucleic acid sequence encodes amino acids 26-117 of SEQ ID NO: 8. In some embodiments, the rat comprises a nucleic acid encoding a chimeric C1qc polypeptide, wherein the nucleic acid comprises a rat nucleic acid sequence and a human nucleic acid sequence, wherein the rat nucleic acid sequence encodes amino acids 32-116 of SEQ ID NO: 9.

In a specific embodiment, the genetically modified non-human animal is a rat and comprises in its genome: (i) at the endogenous C1qa locus a nucleic acid sequence encoding a chimeric rat human C1qa polypeptide wherein the nucleic acid sequence comprises, 5'-3' and in operable linkage a first nucleotide sequence encoding amino acids 1-111 of a rat C1qa polypeptide of SEQ ID NO: 7 and a second nucleotide sequence encoding amino acids 112-245 of a human C1qa polypeptide of SEQ ID NO: 4; (ii) at the endogenous C1qb locus a nucleic acid sequence encoding a chimeric rat/human C1qb polypeptide wherein the nucleic acid sequence comprises, 5'-3' and in operable linkage a third nucleotide sequence encoding amino acids 1-117 of a rat C1qb polypeptide of SEQ ID NO: 8 and a fourth nucleotide sequence encoding amino acids 118-251 of a human C1qb polypeptide of SEQ ID NO: 5; and (iii) at the endogenous C1qc locus a nucleic acid sequence encoding a chimeric rat/human C1qc polypeptide wherein the nucleic acid sequence comprises, 5'-3' and in operable linkage a fifth nucleotide sequence encoding amino acids 1-116 of a rat C1qc polypeptide of SEQ ID NO: 9 and a sixth nucleotide sequence encoding amino acids 114-245 of a human C1qc polypeptide of SEQ ID NO: 6. In a particular embodiment, the genetically modified non-human animal is a rat which comprises in its genome: at the endogenous C1qa locus a nucleic acid sequence encoding a chimeric rat/human C1qa polypeptide which comprises the amino acid sequence of SEQ ID NO: 55; at the endogenous C1qb locus a nucleic acid sequence encoding a chimeric rat/human C1qb polypeptide which comprises the amino acid sequence of SEQ ID NO: 56; and at the endogenous C1qa locus a nucleic acid sequence encoding a chimeric rat/human C1qc polypeptide which comprises the amino acid sequence of SEQ ID NO: 57.

In another specific embodiment, the genetically modified non-human animal is a mouse and comprises in its genome: (i) at the endogenous C1qa locus a nucleic acid sequence encoding a chimeric mouse/human C1qa polypeptide wherein the nucleic acid sequence comprises, 5'-3' and in operable linkage a first nucleotide sequence encoding amino acids 1-111 of a mouse C1qa polypeptide of SEQ ID NO: 1 and a second nucleotide sequence encoding amino acids 112-245 of a human C1qa polypeptide of SEQ ID NO: 4; (ii) at the endogenous C1qb locus a nucleic acid sequence encoding a chimeric mouse/human C1qb polypeptide wherein the nucleic acid sequence comprises, 5'-3' and in operable linkage a third nucleotide sequence encoding amino acids 1-117 of a mouse C1qb polypeptide of SEQ ID NO: 2 and a fourth nucleotide sequence encoding amino acids 118-251 of a human C1qb polypeptide of SEQ ID NO: 5; and (iii) at the endogenous C1qc locus a nucleic acid sequence encoding a chimeric mouse/human C1qc polypeptide wherein the nucleic acid sequence comprises, 5'-3' and in operable linkage a fifth nucleotide sequence encoding amino acids 1-114 of a mouse C1qc polypeptide of SEQ ID NO: 3 and a sixth nucleotide sequence encoding amino acids 114-245 of a human C1qc polypeptide of SEQ ID NO: 6. In a particular embodiment, the genetically modified non-human animal is a mouse which comprises in its genome: at the endogenous C1qa locus a nucleic acid sequence encoding a chimeric mouse/human C1qa polypeptide which comprises the amino acid sequence of SEQ ID NO: 10; at the endogenous C1qb locus a nucleic acid sequence encoding a chimeric mouse/human C1qb polypeptide which comprises the amino acid sequence of SEQ ID NO: 11; and at the endogenous C1qa locus a nucleic acid sequence encoding a chimeric mouse/human C1qc polypeptide which comprises the amino acid sequence of SEQ ID NO: 12.

In some embodiments disclosed herein, the genetically modified non-human animal does not express a functional endogenous C1qa, C1qb, and/or C1qc polypeptide(s).

In another aspect, provided herein are methods of making a genetically modified non-human animal (such as, for example a non-human mammal such as a rodent including but not limited to a mouse or rat) comprising in its genome a chimeric C1q locus that includes a gene encoding a chimeric non-human/human C1qa polypeptide, a gene encoding a chimeric non-human/human C1qb polypeptide, and/or a gene encoding a chimeric non-human/human C1qc polypeptide, the method comprising introducing into the non-human animal genome a nucleic acid sequence(s) comprising a) a gene encoding a chimeric non-human/human C1qa polypeptide, b) a gene encoding a chimeric non-human/human C1qb polypeptide, and/or c) a gene encoding a chimeric non-human/human C1qc polypeptide. In some embodiments, the nucleic acid comprising a gene encoding a chimeric C1q polypeptide is at a location in the genome outside the endogenous locus. Thus, in some embodiments, the endogenous C1q gene(s) or a portion thereof may be silenced and/or deleted, such that the non-human animal does not express a functional endogenous C1q polypeptide (e.g., does not express a functional endogenous C1qa, C1qb, and/or C1qc polypeptide). In other embodiments, the nucleic acid comprising a gene encoding a chimeric polypeptide is at the endogenous non-human C1q locus; and in one embodiment, the nucleic acid comprising a gene encoding a chimeric C1q polypeptide replaces the endogenous non-human C1q gene at the endogenous C1q locus.

Thus, provided herein are methods of making the genetically modified non-human animal described herein, wherein the nucleic acid sequence encoding a chimeric C1q polypeptide is introduced at the endogenous non-human mammal C1q locus. In a specific aspect, disclosed is a method of making a genetically modified non-human animal, wherein the nucleic acid sequence encoding a chimeric C1q polypeptide replaces a nucleotide sequence encoding an endogenous non-human mammal C1q polypeptide.

In some embodiments, the method of making a genetically modified non-human animal described herein, e.g., a genetically modified rat or mouse, comprises generating a targeting vector (e.g., a large targeting vector (LTVEC)) comprising nucleic acid sequence(s) encoding a chimeric C1qa, C1qb, and/or C1qc polypeptide(s), introducing said targeting vector into ES cells, and generating said non-human animal from said ES cell.

In another aspect, disclosed herein is a chimeric C1q polypeptide comprising a globular head domain that is substantially human and an N-terminal stalk-stem region that is substantially non-human, wherein the chimeric C1q polypeptide is selected from the group consisting of a chimeric C1qa polypeptide, a chimeric C1qb polypeptide, and a chimeric C1qc polypeptide. In some embodiments, such a chimeric C1q polypeptide is made from the genetically modified non-human animal disclosed herein. In other embodiments, a chimeric C1q polypeptide is made from an appropriate host cell.

In still another aspect, disclosed herein is a chimeric C1q protein comprising one or more of the chimeric C1q polypeptides disclosed herein. In some embodiments, the chimeric C1q protein comprises at least one chimeric C1qa, one chimeric C1qb, and one chimeric C1qc polypeptide. In some embodiments, the chimeric C1q protein comprises 6 each of a chimeric C1qa polypeptide, a chimeric C1qb polypeptide, and a chimeric C1qc polypeptide.

In another aspect, disclosed herein is an isolated nucleic acid encoding a chimeric C1q polypeptide (a C1qa polypeptide, a C1qb polypeptide, or a C1qc polypeptide), and comprising a non-human mammal nucleic acid sequence and a human nucleic acid sequence. In some embodiments, the human nucleic acid sequence encodes substantially the globular head domain of a human C1q polypeptide and the non-human nucleic acid sequence encodes substantially the N-terminal stalk-stem region of a cognate non-human C1q polypeptide. In some embodiments, the isolated nucleic acid encodes a chimeric C1q protein, and comprises one or more of a first, second or third nucleotide sequences, wherein the first nucleotide sequence encodes a chimeric C1qa polypeptide, the second nucleotide sequence encodes a chimeric C1qb polypeptide, and the third nucleotide sequence encodes a chimeric C1qc polypeptide.

In still another aspect, provided herein is a cell comprising an isolated nucleic acid disclosed herein. In some embodiments, the cell is an embryonic stem (ES) cell, e.g., a rodent (such as mouse or rat) ES cell.

In a further aspect, provided herein is a rodent model for testing a C1q-based bispecific antigen-binding protein, wherein the antigen-binding protein binds both human C1q and an antigen of interest, comprising a genetically modified rodent disclosed herein and further comprising the antigen of interest or a cell expressing the antigen of interest.

In another aspect, disclosed herein are methods of screening for a drug candidate that targets an antigen of interest comprising introducing the antigen of interest into the genetically modified non-human animal. e.g., the rodent, e.g., the rat or the mouse, provided herein, contacting said animal with a drug candidate of interest, wherein the drug candidate is directed against the human C1q and the antigen of interest, and assaying to determine whether the drug candidate is efficacious in preventing, reducing, or eliminating cells characterized by the presence or expression of the antigen of interest. In one embodiment, the step of introducing comprises expressing in the animal the antigen of interest (such as, for example, genetically modifying the rodent that expresses the antigen of interest) or introducing into said animal a cell or virus expressing the antigen of interest. In one specific aspect, the cell can be a tumor cell or bacterial cell. In a further aspect the antigen of interest can be a tumor associated antigen or a bacterial antigen. In another aspect, the cell can be a bacterial cell.

In another aspect, provided herein is a method of screening among therapeutic drug candidates that target an antigen of interest, the method comprising mixing a cell or virus expressing the antigen of interest with (i) a drug candidate of interest, wherein the drug candidate is directed against the human C1q and the antigen of interest, and (ii) a blood sample (e.g., a whole blood sample) of a genetically modified rodent described herein, and (b) assaying to determine whether the drug candidate is efficacious in reducing or eliminating the cell or virus characterized by the presence or expression of the antigen of interest. The determination can be made based on measuring, e.g., percentage survival of the cell or virus where a drug candidate is used as compared to a control drug or no drug at all. The antigen of interest may be a tumor-associated antigen or an infectious disease associated antigen, e.g., a bacterial or a viral antigen. In some embodiments, the antigen of interest is a bacterial antigen such as a *Staphylococcus* antigen. In some embodiments, the cell is a bacterial cell such as a *Staphylococcus* cell.

In some embodiments, provided is a method of screening for a drug candidate, wherein the step of introducing comprises infecting the animal (e.g., the rat or the mouse) with the antigen of interest (for example, a viral antigen or a bacterial antigen such as a *Staphylococcus* antigen). Thus, in one aspect, the step of introducing comprises infecting the animal with a virus or bacteria.

In some embodiments, the genetically modified non-human animal provided herein (e.g., the rodent, e.g., the rat or the mouse) is an immunocompetent animal (e.g., immunocompetent rat or mouse).

In another aspect, disclosed herein are methods of assessing whether an antibody comprising a human Fc region can activate classical complement pathway by utilizing a genetically engineered non-human animal (e.g., a rodent such as a mouse or rat) expressing a humanized C1q protein disclosed herein. In some embodiments, the method comprises (a)

providing a cell expressing an antigen of interest on the cell surface, a candidate antibody comprising a human Fc region and directed to the antigen of interest, and a serum sample from a genetically engineered non-human animal expressing a humanized C1q protein; (b) mixing the cell with the candidate antibody to allow the antibody to bind to the antigen of interest expressed on the cell surface; (c) adding the serum sample to the cell-antibody mixture to permit binding of the humanized C1q proteins in the serum sample to antibodies bound to the antigen of interest on the cell; and (d) measuring cytotoxicity of the cell.

BRIEF DESCRIPTION OF THE DRAWINGS

The accompanying drawings, which are incorporated in and constitute a part of this specification, illustrate several embodiments and together with the description illustrate the disclosed compositions and methods.

Unless specifically indicated (e.g., loxP, etc.), all human exon sequences are in empty boxes and all human intron sequences are in double lines. All mouse or rat sequences are either in filled boxes (exons) or single lines (introns).

FIG. 1C shows a schematic representation (not to scale) of the electroporation (EP) of a large targeting vector containing all three mouse/human chimeric C1q genes into mouse C1q KO HET ES cells. Exons of the three C1q genes are labeled below the diagram (e.g., E1, E2, and E3). Lox=loxP site; Ub-Hyg=hgromycin selection cassette; pgk-Neo=neomycin selection cassette; p=polyA sequence. Sequence junctions between mouse, human, or cassette sequences are indicated with a line and a SEQ ID NO for that respective sequence below each junction.

FIG. 3B shows C1qb amino acid alignments for rat (rC1qb), human (hC1QB), and mouse (mC1qb) polypeptides, with similarities being outlined and mismatches shown in lower cases. Signal peptide sequences are boxed and labeled. The collagen triple helix repeat sequences are boxed and labeled. The C1qb globular head domain sequences are boxed with dashed lines, and the junction of mouse/human or rat/human sequence in the chimeric polypeptides is depicted with a dashed line and indicated with an arrow.

FIG. 3C shows C1qc amino acid alignments for rat (rC1qc), human (hC1QC), and mouse (mC1qc) polypeptides, with similarities being outlined and mismatches shown in lower cases. Signal peptide sequences are boxed and labeled. The collagen triple helix repeat sequences are boxed and labeled. The C1qc globular head domain sequences are boxed with dashed lines, and the junction of mouse/human or rat/human sequence in the chimeric polypeptides is depicted with a dashed line and indicated with an arrow.

FIG. 4 bottom panel shows a hemolysis assay measuring complement activity comparing serum samples from wild-type littermate mouse (WT) and chimeric C1q mouse (1615 HO; HO=homozygous), and human serum.

FIG. 7 shows complement dependent cytotoxicity (CDC) activity mediated by a human anti-CD20 antibody at 20 nM and a serum sample (normal human serum, humanized C1q rat serum, or wild type rat serum) on Raji cells.

DETAILED DESCRIPTION

Figure 1A:
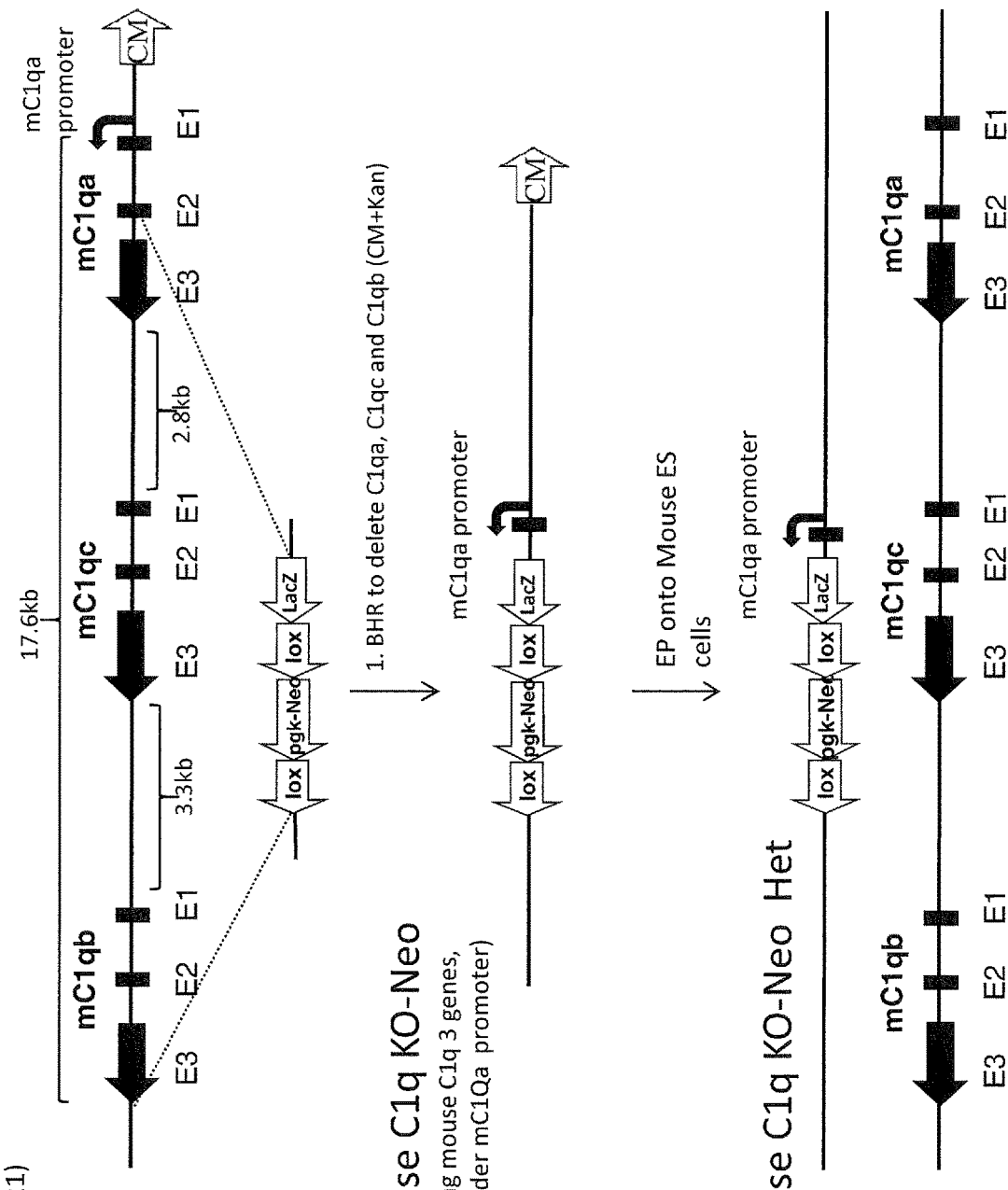
FIG. 1A is a schematic representation (not to scale) of the exemplary method of deleting of the mouse C1q locus comprising all three mouse C1q genes (mouse genes are indicated with "m" before the gene label). Exons of the three C1q genes are labeled below the diagram (e.g., E1, E2, and E3). Mouse BAC stands for bacterial artificial chromosome; BHR stands for bacterial homologous recombination; EP stands for electroporation. HET=heterozygous; CM=chloramphenicol; lox=loxP site; pgk-Neo=neomycin selection cassette.

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

"Primers" are a subset of probes which are capable of supporting some type of enzymatic manipulation and which can hybridize with a target nucleic acid such that the enzymatic manipulation can occur. A primer can be made from any combination of nucleotides or nucleotide derivatives or analogs available in the art which do not interfere with the enzymatic manipulation.

"Probes" are molecules capable of interacting with a target nucleic acid, typically in a sequence specific manner, for example through hybridization. The hybridization of nucleic acids is well understood in the art and discussed herein. Typically a probe can be made from any combination of nucleotides or nucleotide derivatives or analogs available in the art.

"Functional" as used herein, e.g., in reference to a functional protein, includes a protein that retains at least one biological activity normally associated with the native protein. For example, in some embodiments, a replacement at an endogenous locus (e.g., replacement at endogenous non-human C1q loci) results in a locus that fails to express a functional endogenous protein.

The term "operably linked" includes a juxtaposition wherein the components so described are in a relationship permitting them to function in their intended manner. As such, a nucleic acid sequence encoding a protein may be operably linked to regulatory sequences (e.g., promoter, enhancer, silencer sequence, etc.) so as to retain proper transcriptional regulation. For example, by "operably linked" is meant a functional linkage between a nucleic acid expression control sequence (such as a promoter) and a second nucleic acid sequence, wherein the expression control sequence directs transcription of the nucleic acid corresponding to the second sequence. In addition, various portions of the humanized protein of the present disclosure may be operably linked or fused to retain proper folding, processing, targeting, expression, and other functional properties of the protein in the cell. Unless stated otherwise, various domains of the humanized protein of the present disclosure are operably linked to each other.

The term "humanized" as used in the phrases "humanized C1q allele," "humanized C1qa allele," "humanized C1qb allele," "humanized C1qc allele," "humanized C1q gene," "humanized C1qa gene," "humanized C1qb gene" or "humanized C1qc gene," includes, but is not limited to, embodiments wherein all or a portion of an endogenous non-human C1q, C1qa, C1qb, and/or C1qc gene or allele is replaced by a corresponding portion of the human C1q, C1qa, C1qb, and/or C1qc gene or allele. For example, in some embodiments, the term "humanized" refers to the complete replacement of the coding region (e.g., the exons) of the endogenous non-human C1q, C1qa, C1qb, and/or C1qc gene or allele with the corresponding coding region of the human C1q, C1qa, C1qb, and/or C1qc gene or allele, while the endogenous non-coding region(s) (such as, but not limited to, the promoter, the 5' and/or 3' untranslated region(s), enhancer elements, etc.) of the non-human animal may not be replaced. In some embodiments, the humanized gene or allele are placed either randomly in the genome or targeted to a particular location within the genome. Thus, in some embodiments, the humanized gene or allele is placed in a location in the genome that is not the native location for corresponding endogenous gene or allele, i.e., it is placed at a location other than the endogenous locus. In other embodiments, the humanized gene or allele is placed at the endogenous locus; for example, the humanized gene or allele may replace the endogenous gene or allele at the endogenous locus. In some embodiments, the non-human animal is a rodent, such as a rat or mouse.

A "humanized protein" includes, but is not limited to, embodiments wherein all or a portion of the encoded endogenous non-human C1q, C1qa, C1qb, and/or C1qc protein is replaced by the corresponding portion of the human C1q, C1qa, C1qb, and/or C1qc protein. In some embodiments, a "humanized protein" can be encoded by a humanized C1q, C1qa, C1qb, and/or C1qc gene or allele but still is a fully human C1q, C1qa, C1qb, and/or C1qc protein (such as, but not limited to, the situation wherein all of the coding regions (e.g., the exons) of the endogenous non-human C1q, C1qa, C1qb, and/or C1qc gene or allele are replaced by the corresponding coding regions of the human C1q, C1qa, C1qb, and/or C1qc gene or allele but the endogenous non-coding region(s) (such as, but not limited to, the promoter, the 5' and/or 3' untranslated region(s), enhancer elements, etc.) of the non-human animal is not replaced). In some embodiments, the humanized protein is expressed from the humanized gene or allele that is not at its native location in the genome, e.g., it is not at the endogenous locus. In other embodiments, the humanized protein is expressed from the humanized gene or allele that is at the endogenous locus. In some embodiments, the humanized protein is expressed from the humanized gene or allele that replaces the endogenous gene or allele at the endogenous locus. In some embodiments, the non-human animal is a rodent, such as a rat or mouse.

The present disclosure is directed to like-for-like humanization. For example, a nucleotide sequence of an endogenous non-human C1q gene is operably linked to a nucleotide sequence of a cognate human C1q gene to form a chimeric humanized gene. In some embodiments, a nucleotide sequence of an endogenous C1qa gene is operably linked to a nucleotide sequence of a human C1qa gene to form a humanized C1qa gene. In other embodiments, a nucleotide sequence of an endogenous C1qb gene is operably linked to a nucleotide sequence of a human C1qb gene to form a humanized C1qb gene. In still other embodiments, a nucleotide sequence of an endogenous C1qc gene is operably linked to a nucleotide sequence of a human C1qc gene to form a humanized C1qc gene.

The term "chimeric" as used herein includes a sequence, e.g., nucleic acid or polypeptide sequence, where a portion of the sequence is derived from one organism and a portion of the sequence is derived from a different organism. For example, a chimeric C1q polypeptide may comprise a sequence derived from a mouse or a rat, and another sequence derived from a human C1q protein. In one embodiment, a chimeric C1q polypeptide comprises a globular head domain or a fragment thereof of a human C1q polypeptide, and a stalk domain and a stem domain of a cognate mouse or rat C1q polypeptide.

The term "locus" as in "C1q locus" refers to the location of the genomic DNA comprising a C1q coding region. For example, a C1qa locus refers to the location of the genomic DNA comprising the C1qa coding region; a C1qb locus refers to the location of the genomic DNA comprising the C1qb coding region; and a C1qc locus refers to the location of the genomic DNA comprising the C1qc coding region. A reference to "a C1q locus" means any one of C1qa, C1qb or C1qc locus. Other sequences may be included in a C1q locus that have been introduced for the purposes of genetic manipulation, e.g., selection cassettes, restriction sites, etc.

Other definitions and meaning of various terms used throughout this specification and the claims are included throughout in the relevant sections.

Throughout this application, various publications are referenced. The disclosures of these publications in their entireties are hereby incorporated by reference into this application. The references disclosed are also individually and specifically incorporated by reference herein in their entireties for the material contained in them that is discussed in the sentence in which the reference is relied upon.

B. Compositions

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed, while specific reference to each various individual and collective combinations and permutations of these components may not be explicitly listed, each is specifically contemplated and described herein. For example, if a particular chimeric C1qa, C1qb, and/or C1qc nucleic acid or polypeptide is disclosed and discussed and a number of modifications that can be made to a number of molecules including the chimeric C1qa, C1qb, and/or C1qc nucleic acid or polypeptide are discussed, specifically contemplated is each and every combination and permutation of chimeric C1qa, C1qb, and/or C1qc nucleic acid or polypeptide and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

C. Polypeptides

The present disclosure provides novel chimeric mammalian C1q polypeptides, nucleic acids encoding said polypeptides, and genetically modified non-human mammals that comprise said nucleic acids and can express the chimeric C1q polypeptides.

As used herein, "C1q" (e.g., as in "C1q protein" or "C1q complex"), is one portion of the C1 complex which, along with C1r and C1s, initiates activation of the complement pathway. C1q is the first component of the classical complement pathway, required for clearance of pathogens, apoptotic bodies and possibly tumor cells (Ghai R et al., Immunobiology. 2007; 212(4-5):253-66; Lu J H et al., Cell Mol Immunol. 2008 February; 5(1):9-21). The complement pathway is a part of the innate immune system. Activation of the complement pathway can result in direct lysis of antigen, recruitment of phagocytes and macrophages to the antigenic site, opsonization of the antigen by phagocytes, and cytokine secretion.

Human/mouse/rat C1q protein is composed of polypeptides encoded by three genes, C1qa, C1qc, and C1qb genes, which are arranged tandemly 5'-3' in the order A-C-B (Petry F et al., Immunogenetics. 1996:43(6):370-6). These polypeptides are also referred to herein as a "C1q polypeptide", which can be a C1qa polypeptide, a C1qb polypeptide or a C1qc polypeptide. Each of the C1qa C1qb and C1qc polypeptide chains has an N-terminus region that includes a stalk (or neck) domain containing a cysteine residue followed by a collagen-like domain (stem domain), and an C-terminus region (globular head domain). The N-terminal region is also referred to herein as "N-terminal stalk-stem region", and the C-terminal region is also referred to as the "globular head domain". Human C1q protein (approx. 410 kDa) resembles a bouqet-like structure assembled from six collagenous stems, each ending with a globular head. Each stem/globular head is made up of three polypeptide chains (C1qA, C1qB and C1qC) for a total of 18 polypeptides (six A-, six B-, and six C-chains making up one C1q molecule (Reid K B Biochem Soc Trans. 1983 January; 11(1): 1-12)).

C1q is expressed by splenic macrophages and dendritic cells in both humans and rodents (Castellano G et al., Blood. 2004 May 15; 103(10):3813-20). C1q is secreted and found in human circulation at approximately 100 ug/ml, and at similar levels in mice (Dillon S P et al., Biotechnol J. 2009 August; 4(8): 1210-1214; Yonemasu K et al., Int Arch Allergy Appl Immunol. 1988:86(1):97-101). The protein belongs to a group of defense collagens which recognize pathogen-associated molecular patterns (PAMPs), where the C-terminus/globular head of C1q recognizes the CH3 domain of IgM; CH2 domain of IgG: beta-amyloid; polyanions including DNA; C-reactive protein; serum amyloid P, as well as PAMPs associated with LPS, viruses, and prions (Dunkelberger J R. Song W C, Cell Res. 2010 January; 20(1):34-50; Ghai R et al., Immunobiology. 2007:212(4-5): 253-66). C1q spontaneously assembles with C1s-C1r-C1r-C1s tetramer to form C1 macrocomplex. The C1 macrocomplex is a pentamer of three proteins comprising one C1q complex, and two each of C1r and C1s, where C1r and C1s associate with the stalk-stem domains of C1q. C1r and C1s are regulated by serpin protease inhibitor family member C1 inhibitor (C1INH) (Beinrohr L et al., Trends Mol Med. 2008 December; 14(12):511-21). C1q also binds receptors including CD93, DC-SIGN and CR1/CD35 (Hosszu K K et al., Blood. 2012 Aug. 9;120(6): 1228-36; Bohlson S S at al., Mol Immunol. 2007 January; 44(1-3):33-43). By binding PAMPs, C1q opsonizes and facilitates pathogen clearance and can enhance phagocytosis of target particles sub-optimally opsonized with C3b/C4b or IgG, via CR1 or FcgR, respectively (Bobak D A et al., J Immunol. 1987 Feb. 15; 138(4):1150-6). Thus, C1q activates the classical complement pathway, resulting in both formation of the membrane attack complex (target lysis) and also generation of activation fragments C3a and C5a (Bohlson S S at al., Mol Immunol. 2007 January; 44(1-3):33-43). Lastly, C1q mediates clearance of immune complexes, as well as cells undergoing apoptosis and cells blebs by recognizing apoptotic cell-associated molecular patterns.

To activate the classical complement pathway, C1q binds to the pathogen surface or Fc domain of antibodies through its six globular heads, which results in activation of C1r and C is serine proteases, leading to cleavage of downstream complement components and ultimately complement activation, deposition and cell lysis through the membrane attack complex (see Reid K B Biochem Soc Trans. 1983 January; 11(1): 1-12)).

Exemplary sequences and GenBank Accession Numbers of human, mouse and rat C1qa, C1qb, and C1qc are presented in Tables 1, 2, and 8 below, and in FIG. 3A (C1qa), FIG. 3B (C1qb), and FIG. 3C (C1qc).

As it is C1q that recognizes either the Fc domain of antibodies or antigen directly, it is C1q that is key to providing a humanized complement system. As the globular head domain of C1q (often abbreviated as gC1q) is what recognizes the human antibody or the human pathogen, in certain embodiments provided herein, the globular head domain of C1q was engineered such that it more readily recognizes these molecules. In certain embodiments, the globular head domain of C1q is human while the remainder of the protein is non-human. In such embodiment, the non-human animals provided herein retain the portion of the protein that is known to interact with the C1r/C1s and the remainder of the complement system (e.g., the stem and stalk portion of the protein). Thus, in the embodiments provided herein, the non-human animal expressing C1q harboring a globular head domain that is substantially human and an N-terminal stalk-stem region that is substantially non-human is useful in assessing the requirement for complement system as an effector mechanism of action of a therapeutic molecule, e.g., an antibody. In embodiments provided, said non-human animal is also useful to study the effectiveness of the therapeutic treatment if the complement system is engaged by the antibody. In embodiments provided, said non-human animals are also useful as an in vivo model to test the efficacy of fully human therapeutic antibodies, e.g., bispecific antibodies, designed for infectious disease indications.

Thus, in one aspect, disclosed herein are chimeric mammalian C1q polypeptides (such as, for example chimeric mammalian C1qa, C1qb and/or C1qc polypeptides).

In some embodiments, the chimeric C1q polypeptide provided herein comprises a human C terminal region that is responsible for recognition of immunoglobulin Fc domain, or responsible for recognizing pathogen-associated molecular patterns (PAMPs).

In some embodiments, the chimeric C1q polypeptide provided herein comprises a human globular head domain or a fragment thereof.

In some embodiments, a chimeric C1q polypeptide provided herein comprises a globular head domain that is substantially human. By "a globular head domain that is substantially human", it is meant that the globular head domain in a chimeric (humanized) C1q polypeptide is substantially identical to the globular head domain of a human C1q polypeptide. By "substantially identical", it refers to, (i) in some embodiments, a globular head domain that is at least 90%, 95%, 98%, 99% or 100% identical in sequence to the globular head domain of a human C1q polypeptide; (ii) in other embodiments, a globular head domain that differs from the globular head domain of a human C1q polypeptide by not more than 5, 4, 3, 2 or 1 amino acid(s); (iii) in still other embodiments, a globular head domain that differs from the globular head domain of a human C1q polypeptide only at the N- or C-terminal portion of the domain, e.g., by having the same length but with one or more (e.g., 1, 2, 3, 4, or 5, but not more than 5) amino acid substitutions (such as a conservative substitution) within the N- or C-terminal portion of the globular head domain (e.g., within the 5-10 amino acids at the N- or C-terminus of the globular head domain); and/or (iv) in other embodiments, a globular head domain that is shorter or longer than the globular head domain of a human C1q polypeptide by 1, 2, 3, 4, 5 but not more than 5 amino acids at either the N- or C-terminus of the domain. In some embodiments, a globular head domain substantially identical to the globular head domain of a human C1q polypeptide differs from the human globular head domain by not more than 1, 2, or 3 amino acids within the N-terminal portion (e.g., within the 5-10 amino acids from the N-terminus) of the domain, and in certain such embodiments, the difference comprises a substitution(s) of an amino acid in the human globular head domain with the amino acid at the corresponding position from a cognate non-human (e.g., a mouse or rat) globular head domain. For example, disclosed herein in FIG. 3A is a chimeric C1qa polypeptide that has a globular head domain that is substantially human—the globular domain of this chimeric C1qa polypeptide differs from the globular head domain of a human C1qa of SEQ ID NO: 4 by only one amino acid at the third position from the N-terminus of the globular head domain ("K" in human, and "R" in the chimeric, mouse and rat C1qa polypeptides).

In some embodiments, the chimeric C1q polypeptide comprises an N terminal stalk-stem region that is responsible for recognizing non-human (e.g., endogenous rodent) C1s and C1r and/or other non-human (e.g., endogenous rodent) components of the complement pathway.

In some embodiments, the chimeric C1q polypeptide comprises a non-human stalk-stem region. In some embodiments, the chimeric C1q polypeptide comprises a non-human stalk domain. In some embodiments, the chimeric C1q polypeptide comprises a non-human collagen triple helix domain. In some embodiments, the chimeric C1q polypeptide comprises a non-human N terminal region comprising non-human stem and non-human stalk domains.

In some embodiments, a chimeric C1q polypeptide provided herein comprises an N-terminal stalk-stem region that is substantially non-human. By "an N-terminal stalk-stem region that is substantially non-human", it is meant that the N-terminal stalk-stem region of a chimeric C1q polypeptide is substantially identical to the corresponding N-terminal stalk-stem region of a non-human (e.g., a rodent) C1q polypeptide. By "substantially identical", it is meant (i) in some embodiments, an N-terminal stalk-stem region that is at least 90%, 95%, 95%, 99% or 100% identical in sequence with the N-terminal stalk-stem region of a non-human C1q polypeptide; (ii) in other embodiments, an N-terminal stalk-stem region that differs from the N-terminal stalk-stem region of a non-human C1q polypeptide by not more than 5, 4, 3, 2 or 1 amino acid(s); (iii) in still other embodiments, an N-terminal stalk-stem region that differs from the N-terminal stalk-stem region of a non-human C1q polypeptide only at the C-terminus, e.g., by having the same length but with one or more amino acid substitutions of the 5-10 amino acids from the C-terminus of the stalk-stem region; and/or (iv) in other embodiments, an N-terminal stalk-stem region that is shorter or longer than the N-terminal stalk-stem region of a non-human C1q polypeptide by 1, 2, 3, 4, or 5 but not more than 5 amino acids at the N- or C-terminus of the region. In specific embodiments, the N-terminal stalk-stem region of a chimeric C1q polypeptide is identical to the N-terminal stalk-stem region of a non-human (e.g., rodent) C1q polypeptide.

In one embodiment, a human C1qa polypeptide comprises the amino acid sequence as set forth in SEQ ID NO: 4. In another embodiment, a human C1qa polypeptide comprises the amino acid sequence as set forth in GenBank Accession No. NP_001334394.1. In one embodiment, a human C1qb polypeptide comprises the amino acid sequence as set forth in SEQ ID NO: 5. In another embodiment, a human C1qb polypeptide comprises the amino acid sequence as set forth in GenBank Accession No. NP_000482.3. In one embodiment, a human C1qc polypeptide comprises the amino acid sequence as set forth in SEQ ID NO: 6. In another embodiment, a human C1qc polypeptide comprises the amino acid sequence as set forth in GenBank Accession No. NP_001334548.1.

In one embodiment, a mouse C1qa polypeptide comprises the amino acid sequence as set forth in SEQ ID NO: 1. In another embodiment, a mouse C1qa polypeptide comprises the amino acid sequence as set forth in GenBank Accession No. NP_031598.2. In one embodiment, a mouse C1qb polypeptide comprises the amino acid sequence as set forth in SEQ ID NO: 2. In another embodiment, a mouse C1qb polypeptide comprises the amino acid sequence as set forth in GenBank Accession No. NP_033907.1. In one embodiment, a mouse C1qc polypeptide comprises the amino acid sequence as set forth in SEQ ID NO: 3. In another embodiment, a mouse C1qc polypeptide comprises the amino acid sequence as set forth in GenBank Accession No. NP_031600.2.

In one embodiment, a rat C1qa polypeptide comprises the amino acid sequence as set forth in SEQ ID NO: 7. In another embodiment, a rat C1qa polypeptide comprises the amino acid sequence as set forth in GenBank Accession No. NP_001008515.1. In one embodiment, a rat C1qb polypeptide comprises the amino acid sequence as set forth in SEQ ID NO: 8. In another embodiment, a rat C1qb polypeptide comprises the amino acid sequence as set forth in GenBank Accession No. NP_062135.1. In one embodiment, a rat C1qc polypeptide comprises the amino acid sequence as set forth in SEQ ID NO: 9. In another embodiment, a rat C1qc polypeptide comprises the amino acid sequence as set forth in GenBank Accession No. NP_001008524.1.

Thus, in one aspect, the chimeric mammalian C1q polypeptide is a chimeric C1qa polypeptide.

In some embodiments, the chimeric C1qa polypeptide comprises a human globular head domain or a fragment thereof. In one embodiment, the polypeptide is a chimeric C1qa polypeptide comprising amino acids 122-222 of the human C1qa polypeptide as set forth in SEQ ID NO: 4 (for example, a chimeric mammalian C1qa polypeptide comprising amino acids 122-235 or 112-245 of the human C1qa polypeptide).

In some embodiments, the chimeric C1qa polypeptide comprises a globular head domain that is substantially human (i.e., a globular head domain substantially identical to the globular head domain of a human C1qa polypeptide). In one embodiment, a human C1qa polypeptide comprises the amino acid sequence of SEQ ID NO: 4, and amino acids 108-245 of SEQ ID NO: 4 constitute the globular head domain of the human C1qa polypeptide of SEQ ID NO: 4 (see FIG. 3A). Thus, in some embodiments, a chimeric C1qa polypeptide comprises a globular head domain that is substantially identical to the human C1qa globular head domain represented by amino acids 108-245 of SEQ ID NO: 4. In a specific embodiment, the globular head domain of a chimeric C1qa polypeptide is represented by amino acids 108-245 of SEQ ID NO: 10, such domain differing from the human C1qa globular head domain represented by amino acids 108-245 of SEQ ID NO: 4 in one amino acid (the third amino acid residue being "R" as in mouse and rat C1qa, instead of "K" in human C1qa). In another specific embodiment, a chimeric C1qa polypeptide comprises a globular head domain that is identical to the human C1qa globular head domain represented by amino acids 108-245 of SEQ ID NO: 4.

In some embodiments, a chimeric C1qa polypeptide comprises non-human C1qa stalk and/or stem domains. Thus, in some embodiments, a chimeric mammalian C1qa polypeptide comprises a non-human sequence which is a mouse sequence comprising at least amino acids 33-102, 30-102, 25-105, 23-107 or 23-111 of the mouse C1qa polypeptide set forth in SEQ ID NO: 1. In other embodiments, the chimeric mammalian C1qa polypeptide comprises a non-human sequence which is a rat sequence comprising at least amino acids 33-102, 30-102, 25-105, 23-107 or 23-111 of the rat C1qa polypeptide set forth in SEQ ID NO: 7.

In some embodiments, the chimeric C1qa polypeptide comprises an N-terminal stalk-stem region that is substantially non-human, i.e., an N-terminal stalk-stem region that is substantially identical to the N-terminal stalk-stem region of a non-human C1qa polypeptide. In certain embodiments, the chimeric C1qa polypeptide comprises an N-terminal stalk-stem region that is substantially identical to the N-terminal stalk-stem region of a mouse C1qa polypeptide. In one embodiment, the mouse C1qa polypeptide comprises the amino acid sequence of SEQ ID NO: 1 (FIG. 3A), and amino acids 23-107 of SEQ ID NO: 1 constitute the N-terminal stalk-stem region of the mouse C1qa polypeptide of SEQ ID NO: 1 (FIG. 3A). Thus, in some embodiments, a chimeric C1qa polypeptide comprises an N-terminal stalk-stem region that is substantially identical to the mouse C1qa N-terminal stalk-stem region represented by amino acids 23-107 of SEQ ID NO: 1. In a specific embodiment, the N-terminal stalk-stem region of a chimeric C1qa polypeptide is represented by amino acids 23-107 of SEQ ID NO: 1. In some embodiments, the chimeric C1qa polypeptide comprises an N-terminal stalk-stem region that is substantially identical to the N-terminal stalk-stem region of a rat C1qa polypeptide. In one embodiment, the rat C1qa polypeptide comprises the amino acid sequence of SEQ ID NO: 7 (FIG. 3A), and amino acids 23-107 of SEQ ID NO: 7 constitute the N-terminal stalk-stem region of the rat C1qa polypeptide of SEQ ID NO: 7 (FIG. 3A). Thus, in some embodiments, a chimeric C1qa polypeptide comprises an N-terminal stalk-stem region that is substantially identical to the rat C1qa N-terminal stalk-stem region represented by amino acids 23-107 of SEQ ID NO: 7. In a specific embodiment, the N-terminal stalk-stem region of a chimeric C1qa polypeptide is represented by amino acids 23-107 of SEQ ID NO: 7.

In some embodiments, the chimeric C1qa polypeptide comprises a globular head domain that is substantially human and an N-terminal stalk-stem region that is substantially non-human. For example, disclosed herein is a chimeric mammalian C1qa polypeptide, wherein the chimeric mammalian C1qa polypeptide comprises at least amino acids 23-245 of the polypeptide set forth in SEQ ID NO: 10 (mouse/human) or at least amino acids 23-245 of the polypeptide set forth in SEQ ID NO:55 (rat/human). In one aspect, the chimeric C1qa polypeptide is or comprises SEQ ID NO: 10 or SEQ ID NO: 55.

In another aspect, the chimeric mammalian C1q polypeptide is a C1qb polypeptide.

In some embodiments, the chimeric C1qb polypeptide comprises a human C1qb globular head or a fragment thereof. In one embodiment, the polypeptide is a chimeric C1qb polypeptide comprising amino acids 125-233 of the human C1qb polypeptide as set forth in SEQ ID NO: 5 (such as, for example, amino acids 120-250 or 118-251 of the human C1qb polypeptide).

In some embodiments, the chimeric C1qb polypeptide comprises a globular head domain that is substantially human (i.e., a globular head domain substantially identical to the globular head domain of a human C1qb polypeptide). In one embodiment, a human C1qb polypeptide comprises the amino acid sequence of SEQ ID NO: 5 (FIG. 3B), and amino acids 115-251 of SEQ ID NO: 5 constitute the globular head domain of the human C1qb polypeptide of SEQ ID NO: 5 (FIG. 3B). Thus, in some embodiments, a chimeric C1qb polypeptide comprises a globular head domain that is substantially identical to the human globular head domain represented by amino acids 115-251 of SEQ ID NO: 5. In a specific embodiment, the globular head domain of a chimeric C1qb polypeptide is represented by amino acids 115-251 of SEQ ID NO: 11, such domain differing from the human C1qb globular head domain represented by amino acids 115-251 of SEQ ID NO: 5 in one amino acid (the first amino acid residue being "G" as in mouse C1qb, instead of "K" in human C1qb). In another specific embodiment, a chimeric C1qb polypeptide comprises a globular head domain that is identical to the human C1qb globular head domain represented by amino acids 115-251 of SEQ ID NO: 5.

In some embodiments, a chimeric C1qb polypeptide comprises non-human C1qb stalk and/or stem domains. In some embodiments, the chimeric mammalian C1qb polypeptide comprises a non-human mammal sequence which is a mouse sequence comprising at least amino acids 32-105, 27-105, 27-110, 26-114, or 26-117 of the mouse C1qb polypeptide set forth in SEQ ID NO: 2. In other embodiments, the chimeric mammalian C1qb polypeptide comprises a non-human mammal sequence which is a rat sequence comprising at least amino acids 32-105, 27-105, 27-110, 26-114, or 26-117 of the rat C1qb polypeptide set forth in SEQ ID NO: 8.

In some embodiments, the chimeric C1qb polypeptide comprises an N-terminal stalk-stem region that is substantially non-human, i.e., an N-terminal stalk-stem region that is substantially identical to the N-terminal stalk-stem region of a non-human C1qb polypeptide. In certain embodiments, the chimeric C1qb polypeptide comprises an N-terminal stalk-stem region that is substantially identical to the N-terminal stalk-stem region of a mouse C1qb polypeptide. In one embodiment, the mouse C1qb polypeptide comprises the amino acid sequence of SEQ ID NO: 2 (FIG. 3B), and amino acids 26-114 of SEQ ID NO: 2 constitute the N-terminal stalk-stem region of the mouse C1qb polypeptide of SEQ ID NO: 2 (FIG. 3B). Thus, in some embodiments, a chimeric C1qb polypeptide comprises an N-terminal stalk-stem region that is substantially identical to the mouse C1qb N-terminal stalk-stem region represented by amino acids 26-114 of SEQ ID NO: 2. In a specific embodiment, the N-terminal stalk-stem region of a chimeric C1qb polypeptide is represented by amino acids 26-114 of SEQ ID NO: 2. In some embodiments, the chimeric C1qb polypeptide comprises an N-terminal stalk-stem region that is substantially identical to the N-terminal stalk-stem region of a rat C1qb polypeptide. In one embodiment, the rat C1qb polypeptide comprises the amino acid sequence of SEQ ID NO: 8 (FIG. 3B), and amino acids 26-114 of SEQ ID NO: 8 constitute the N-terminal stalk-stem region of the rat C1qb polypeptide of SEQ ID NO: 8 (FIG. 3B). Thus, in some embodiments, a chimeric C1qb polypeptide comprises an N-terminal stalk-stem region that is substantially identical to the rat C1qb N-terminal stalk-stem region represented by amino acids 26-114 of SEQ ID NO: 8. In a specific embodiment, the N-terminal stalk-stem region of a chimeric C1qb polypeptide is represented by amino acids 26-114 of SEQ ID NO: 8.

In some embodiments, the chimeric C1qb polypeptide comprises a globular head domain that is substantially human and an N-terminal stalk-stem region that is substantially non-human. For example, disclosed herein is a chimeric mammalian C1qb polypeptide, wherein the polypeptide comprises at least amino acids 26-251 of the polypeptide set forth in SEQ ID NO: 11 (mouse/human) or at least amino acids 26-251 of the polypeptide set forth in SEQ ID NO: 56 (rat/human). In one aspect, the chimeric C1qb polypeptide is or comprises SEQ ID NO: 11 or SEQ ID NO: 56.

In another aspect, the chimeric mammalian C1q polypeptide is a chimeric C1qc polypeptide.

In some embodiments, the chimeric C1qc polypeptide comprises a human C1qc globular head or a fragment thereof. In one embodiment, the polypeptide is a chimeric C1qc polypeptide comprising amino acids 118-234 of the human C1qc polypeptide as set forth in SEQ ID NO: 6 (for example, a chimeric mammalian C1qc polypeptide comprising amino acids 114-245 of the human C1qc polypeptide set forth in SEQ ID NO:6).

In some embodiments, the chimeric C1qc polypeptide comprises a globular head domain that is substantially human (i.e., a globular head domain substantially identical to the globular head domain of a human C1qc polypeptide). In one embodiment, the human C1qc polypeptide comprises the amino acid sequence of SEQ ID NO: 6 (FIG. 3C), and amino acids 113-245 of SEQ ID NO: 6 constitute the globular head domain of the human C1qc polypeptide of SEQ ID NO: 6 (FIG. 3C). Thus, in some embodiments, a chimeric C1qc polypeptide comprises a globular head domain that is substantially identical to the human C1qc globular head domain represented by amino acids 113-245 of SEQ ID NO: 6. In a specific embodiment, the globular head domain of a chimeric C1qc polypeptide is identical to the human C1qc globular head domain represented by amino acids 113-245 of SEQ ID NO: 6.

In some embodiments, a chimeric C1qc polypeptide comprises non-human C1qc stalk and/or stem domains. For example, disclosed herein is a chimeric mammalian C1qc polypeptide wherein the non-human mammal sequence is a mouse sequence comprising at least amino acids 31-111, 30-113, or 30-114 of the mouse C1qc polypeptide set forth in SEQ ID NO: 3; or the chimeric mammalian C1qc polypeptide wherein the non-human mammal sequence is a rat sequence comprising at least amino acids 33-113, 32-115, or 32-116 of the rat C1qc polypeptide set forth in SEQ ID NO: 9.

In some embodiments, the chimeric C1qc polypeptide comprises an N-terminal stalk-stem region that is substantially non-human, i.e., an N-terminal stalk-stem region that is substantially identical to the N-terminal stalk-stem region of a non-human C1qc polypeptide. In certain embodiments, the chimeric C1qc polypeptide comprises an N-terminal stalk-stem region that is substantially identical to the N-terminal stalk-stem region of a mouse C1qc polypeptide. In one embodiment, the mouse C1qc polypeptide comprises the amino acid sequence of SEQ ID NO: 3 (FIG. 3C), and amino acids 30-113 of SEQ ID NO: 3 constitute the N-terminal stalk-stem region of the mouse C1qc polypeptide of SEQ ID NO: 3 (FIG. 3C). Thus, in some embodiments, a chimeric C1qc polypeptide comprises an N-terminal stalk-stem region that is substantially identical to the mouse C1qc N-terminal stalk-stem region represented by amino acids 30-113 of SEQ ID NO: 3. In a specific embodiment, the N-terminal stalk-stem region of a chimeric C1qc polypeptide is represented by amino acids 30-113 of SEQ ID NO: 3. In some embodiments, the chimeric C1qc polypeptide comprises an N-terminal stalk-stem region that is substantially identical to the N-terminal stalk-stem region of a rat C1qc polypeptide. In one embodiment, the rat C1qc polypeptide comprises the amino acid sequence of SEQ ID NO: 9 (FIG. 3C), and amino acids 32-115 of SEQ ID NO: 9 constitute the N-terminal stalk-stem region of the rat C1qc polypeptide of SEQ ID NO: 9 (FIG. 3C). Thus, in some embodiments, a chimeric C1qc polypeptide comprises an N-terminal stalk-stem region that is substantially identical to the rat C1qc N-terminal stalk-stem region represented by amino acids 32-115 of SEQ ID NO: 9. In a specific embodiment, the N-terminal stalk-stem region of a chimeric C1qc polypeptide is represented by amino acids 32-115 of SEQ ID NO: 9.

In some embodiments, the chimeric C1qc polypeptide comprises a globular head domain that is substantially human and an N-terminal stalk-stem region that is substantially non-human. For example, also disclosed herein is a chimeric mammalian C1qc polypeptide, wherein the polypeptide comprises at least amino acids 30-246 of the polypeptide set forth in SEQ ID NO: 12 (mouse/human) or at least amino acids 32-248 of the polypeptide set forth in SEQ ID NO: 57 (rat/human). In one aspect, the chimeric C1qc polypeptide is or comprises SEQ ID NO: 12 or SEQ ID NO: 57.

In one particular aspect, disclosed herein is a chimeric C1q protein comprising one or more of the chimeric C1q polypeptides described herein. For example, disclosed herein is a chimeric C1q protein, wherein the protein comprises at least one, two, three, four, five, or six chimeric C1qa, one, two, three, four, five, or six chimeric C1qb, and/or one, two, three, four, five, or six chimeric C1qc polypeptide. Thus, in some embodiments, the chimeric protein comprises six of each chimeric C1qa polypeptide, chimeric C1qb polypeptide, and chimeric C1qc polypeptide.

The disclosed C1q polypeptides are chimeric polypeptides comprising part human and part non-human amino acid structure. It is understood and herein contemplated that the human and non-human portions of the disclosed chimeric polypeptides are linked, fused, or otherwise chemically joined in such a manner as to retain functionality of the C1q polypeptide. As used herein, "function" and "functionality" refer to the ability to carry out the duties of the native molecule. For C1qa, C1qb and C1qc, functionality includes the ability to form dimers (for C1qa and C1qb heterodimers and for C1qc homodimers), the ability for each portion of the chimeric polypeptide to assume proper folding, the ability to assemble as a trimer of dimers (two C1qa and C1qb heterodimers and 1 C1qc homodimer per trimer) forming a C1q complex, the ability to form a pentamer C1 complex with C1r and C1s, the ability to recognize an Fc domain of an antibody or PAMPs, and the ability initiate the classical complement pathway. The assembly of a C1q protein has been described (see, e.g., Lu et al. (Cellular & Mol. Immunol. 2008, 5(1): 9-21), especially FIG. 1). C1qa and C1qb polypeptide chains dimerize through a disulphide bond at the N-terminal end and two C1qc chains form homodimers through similar disulphide bonding. A C1qa-C1qb dimer and a single C1qc chain form a triple helix and the other C1qc-chain in a C1qc-C1qc dimer trimerizes with another C1qa-C1qb dimer forming two triple helices linked by the disulphide bond between the two C1qc chains. Three such structures form a C1q protein molecule through N-terminal association.

In a particular aspect, disclosed herein is a chimeric mammalian C1qa, C1qb, and/or C1qc polypeptides, wherein the polypeptide disclosed herein further comprises a human, a mouse, or a rat C1qa, C1qb, and/or C1qc signal sequence, respectively. Exemplary human, mouse, and rat C1qa, C1qb, and C1qc signal sequence are shown in FIGS. 3A, 3B, and 3C, respectively.

It is understood and herein contemplated that any of the disclosed chimeric polypeptides can be expressed in a non-human animal. Thus, encompassed by the disclosure is a genetically modified non-human animal, e.g., rodent, e.g., mouse or rat, expressing a chimeric C1q protein(s) described herein or chimeric C1q protein(s) comprising variants, e.g., conservative amino acid substitutions, of the amino acid sequence(s) described herein.

Thus, the chimeric polypeptide can be one of the numerous variants of the chimeric C1qa, C1qb, and/or C1qc polypeptide that are known and herein contemplated. In addition to the known functional C1qa, C1qb, and/or C1qc species and strain variants, there are derivatives of the C1qa, C1qb, and/or C1qc polypeptides which also function in the disclosed methods and compositions. Protein variants and derivatives are well understood to those of skill in the art and can involve amino acid sequence modifications. For example, amino acid sequence modifications typically fall into one or more of three classes: substitutional, insertional or deletional variants. These types of modifications and molecular techniques to achieve them are known in the art. Substitutions, deletions, insertions or any combination thereof may be combined to arrive at a final construct. These modifications must not place the sequence out of reading frame and preferably will not create complementary regions that could produce secondary mRNA structure. The term "conservative," when used to describe a conservative amino acid substitution, includes substitution of an amino acid residue by another amino acid residue having a side chain R group with similar chemical properties (e.g., charge or hydrophobicity). Conservative amino acid substitutions may be achieved by modifying a nucleotide sequence so as to introduce a nucleotide change that will encode the conservative substitution. In general, a conservative amino acid substitution will not substantially change the functional properties of interest of a protein, for example, the ability of C1q complex to bind immunoglobulin or activate the complement pathway. Examples of groups of amino acids that have side chains with similar chemical properties include aliphatic side chains such as glycine, alanine, valine, leucine, and isoleucine; aliphatic-hydroxyl side chains such as serine and threonine; amide-containing side chains such as asparagine and glutamine; aromatic side chains such as phenylalanine, tyrosine, and tryptophan; basic side chains such as lysine, arginine, and histidine; acidic side chains such as aspartic acid and glutamic acid; and, sulfur-containing side chains such as cysteine and methionine. Conservative amino acids substitution groups include, for example, valine/leucine/isoleucine, phenylalanine/tyrosine, lysine/arginine, alanine/valine, glutamate/aspartate, and asparagine/glutamine. In some embodiments, a conservative amino acid substitution can be a substitution of any native residue in a protein with alanine, as used in, for example, alanine scanning mutagenesis. In some embodiments, a conservative substitution is made that has a positive value in the PAM250 log-likelihood matrix disclosed in Gonnet et al. ((1992) Exhaustive Matching of the Entire Protein Sequence Database. Science 256:1443-45), hereby incorporated by reference. In some embodiments, the substitution is a moderately conservative substitution wherein the substitution has a nonnegative value in the PAM250 log-likelihood matrix.

Substantial changes in function are made by selecting substitutions that are less conservative than those listed above, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, (e) by increasing the number of sites for sulfation and/or glycosylation.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

It is understood that one way to define the variants and derivatives of the disclosed proteins herein is through defining the variants and derivatives in terms of homology/identity to specific known sequences. For example, SEQ ID NO: 1 sets forth a particular sequence of mouse C1qa polypeptide, SEQ ID NO: 2 sets forth a particular sequence of mouse C1qb polypeptide, SEQ ID NO: 3 sets forth a particular sequence of mouse C1qc polypeptide, SEQ ID NO: 4 sets forth a particular sequence of human C1qa polypeptide, SEQ ID NO: 5 sets forth a particular sequence of human C1qb polypeptide, SEQ ID NO: 6 sets forth a particular sequence of human C1qc polypeptide, SEQ ID NO: 7 sets forth a particular sequence of rat C1qa polypeptide, SEQ ID NO: 8 sets forth a particular sequence of rat C1qb polypeptide and SEQ ID NO: 9 sets forth a particular sequence of a rat C1qc polypeptide. Specifically disclosed are variants of these and other proteins herein disclosed which have at least 90%, 95%, 98%, or 99% homology to the stated sequence. In some embodiments, the homologous sequences are those represented by GenBank Accession Numbers listed in Tables 1, 2, and 8. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989.

It is understood that the description of conservative mutations and homology can be combined together in any combination, such as embodiments that have at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e., all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence.

D. Nucleic acids

There are a variety of molecules disclosed herein that are nucleic acid based, including for example the nucleic acids that encode, for example the chimeric C1qa, C1qb, C1qc, or any of the nucleic acids disclosed herein for making C1qa, C1qb, and/or C1qc genetically modified non-human animals, as well as various functional nucleic acids.

Disclosed herein are isolated nucleic acids encoding a chimeric mammalian C1qa. C1qb, and/or C1qc polypeptides comprising non-human and human nucleic acid sequences. In some embodiments, the isolated nucleic acid sequences described herein are large targeting vectors including entire regions of the genome, and include exons, introns, and/or intergenic sequences. These may include 5' and 3' untranslated regions, enhancers, promoters, and other regulatory regions. In some embodiments, these regulatory elements are non-human regulatory elements, e.g., regulatory elements of an endogenous non-human C1q gene. In other embodiments, these regulatory elements are human regulatory elements, e.g., regulatory elements of a human C1q gene. In other embodiments, the isolated nucleic acid sequences described herein are cDNA sequences. In some embodiments, the isolated nucleic acids, e.g., a large targeting vector, described herein may include more than a single C1q gene, e.g., two or three genes (e.g., it may encode all three chimeric C1qa, C1qb, and C1qc genes described herein).

In one aspect, disclosed herein is an isolated nucleic acid comprising non-human and human nucleic acid sequences, wherein the nucleic acid encodes a chimeric mammalian C1q polypeptide (e.g., C1qa, C1qb, or C1qc polypeptide) described hereinabove, e.g., a chimeric C1q polypeptide comprising an N-terminal stalk-stem region that is substantially non-human and a globular head domain that is substantially human.

In some embodiments, an isolated nucleic acid encoding a chimeric mammalian C1qa polypeptide comprises non-human and human nucleic acid sequences, wherein the human nucleic acid sequence encodes substantially the globular head domain of a human C1q polypeptide, and the non-human nucleic acid sequence encodes substantially the N-terminal stalk-stem region of a cognate non-human C1q polypeptide.

By "a human C1q nucleic acid sequence encoding substantially the globular head domain of a human C1q polypeptide", it means a fragment of a human C1q gene that encodes the globular head domain or a polypeptide fragment that is slightly longer or shorter than the globular domain of the human C1q polypeptide. By "slightly longer or shorter" is meant a difference in length of not more than 5, 4, 3, 2, or 1 amino acid. Similarly, by "a non-human C1q nucleic acid sequence encoding substantially the N-terminal stalk-stem region of a non-human C1q polypeptide", it means a fragment of a non-human C1q gene that encodes the N-terminal stalk-stem region or a polypeptide fragment that is slightly longer or shorter than the N-terminal stalk-stem region of the non-human C1q polypeptide.

In circumstances where a non-human C1q polypeptide and a cognate human C1q polypeptide share common amino acids near the junction between the stalk-stem region and the globular head domain, it may not be necessary to utilize a human C1q nucleic acid sequence that encodes precisely the globular head domain of the human C1q polypeptide. It is possible to use a nucleic acid sequence of a human C1q gene that encodes substantially the globular head domain of the human C1q polypeptide, in operable linkage to a nucleic acid that encodes substantially the stalk-stem region of the non-human animal C1q polypeptide, such that the chimeric C1q polypeptide includes a globular head domain that is substantially or fully identical to the globular head domain of the human C1q polypeptide, and a stalk-stem region that is substantially or fully identical to stalk-stem region of the non-human C1q polypeptide. Similarly, in circumstances where a non-human C1q polypeptide and a human C1q polypeptide share common amino acids near the C-terminus of the globular head domain, it may not be necessary to utilize a human C1q nucleic acid that encodes precisely the globular head domain of the human C1q polypeptide. It is possible to insert a slightly shorter nucleic acid of a human C1q gene that encodes a polypeptide slightly shorter than the globular head domain of the human C1q polypeptide, in operable linkage to a non-human nucleic acid that encodes the remainder amino acids at the C-terminus of the globular head domain, such that the chimeric C1q polypeptide includes a globular head domain that is still substantially or fully identical to the globular head domain of the human C1q polypeptide.

In one aspect, disclosed herein is an isolated nucleic acid encoding a chimeric mammalian C1qa polypeptide, wherein the human nucleic acid sequence encodes substantially the globular head domain of a human C1qa polypeptide. e.g., encodes the globular head domain of a human C1qa polypeptide or a fragment thereof. For example, in one aspect, disclosed herein is an isolated nucleic acid encoding a chimeric mammalian C1qa polypeptide, wherein the nucleic acid comprises at least a nucleic acid sequence encoding amino acids 122-222 of the human C1qa polypeptide as set forth in SEQ ID NO: 4. For example, the nucleic acid can comprise a nucleic acid sequence (e.g., a portion of human C1qa exon 3) encoding amino acids 122-235 or 112-245 of the human C1qa polypeptide as set forth in SEQ ID NO: 4.

The disclosed nucleic acid encoding chimeric mammalian C1qa polypeptide may further comprise non-human nucleic acid sequences (such as, for example, a nucleic acid sequence encoding substantially the N-terminal stalk-stem region of a non-human C1qa polypeptide). Thus, also disclosed herein are isolated nucleic acids, wherein the nucleic acid sequence comprises at least a nucleotide sequence encoding amino acids 33-102, 30-102, 25-105, 23-107 or 23-111 of the mouse C1qa polypeptide set forth in SEQ ID NO: 1, or at least a nucleotide sequence encoding amino acids 33-102, 30-102, 25-105, 23-107 or 23-111 of the rat C1qa polypeptide set forth in SEQ ID NO: 7. In a particular aspect, disclosed herein is an isolated nucleic acid, wherein the isolated nucleic acid encodes at least amino acids 23-245 of the polypeptide set forth in SEQ ID NO: 10 (mouse/human) or at least amino acids 23-245 of the polypeptide set forth in SEQ ID NO: 55 (rat/human). In one aspect, the isolated nucleic acid encodes a functional chimeric mammalian C1qa polypeptide which is or comprises SEQ ID NO: 10 or SEQ ID NO: 55.

Also disclosed herein is an isolated nucleic acid encoding a chimeric mammalian C1qb polypeptide comprising a nucleic acid sequence encoding substantially the globular head domain of a human C1qb polypeptide, e.g., encoding the globular head domain of a human C1qb polypeptide or a fragment thereof. For example, the nucleic acid encoding the chimeric mammalian C1qb polypeptide comprises at least a nucleic acid sequence encoding amino acids 125-233 of the human C1qb polypeptide as set forth in SEQ ID NO: 5. For example, the nucleic acid can comprise a nucleic acid sequence (e.g., a portion of human C1qb exon 3) encoding amino acids 118-251 of human C1qb polypeptide as set forth in SEQ ID NO: 5.

The disclosed nucleic acid encoding chimeric mammalian C1qb polypeptide may further comprise non-human nucleic acid sequences (such as, for example, a nucleic acid sequence encoding substantially the N-terminal stalk-stem region of a non-human C1qb polypeptide). Thus, also disclosed herein is an isolated nucleic acid, wherein the nucleic acid sequence comprises at least a nucleotide sequence encoding amino acids 32-105, 27-105, 27-110, 26-114, or 26-117 of the mouse C1qb polypeptide set forth in SEQ ID NO: 2, or wherein the nucleic acid sequence comprises at least a nucleotide sequence encoding amino acids 32-105, 27-105, 27-110, 26-114, or 26-117 of the rat C1qb polypeptide set forth in SEQ ID NO: 8. In a particular aspect, disclosed herein is an isolated nucleic acid, wherein the isolated nucleic acid encodes at least amino acids 26-251 of the polypeptide set forth in SEQ ID NO: 11 (mouse/human) or wherein the isolated nucleic acid encodes at least amino acids 26-251 of the polypeptide set forth in SEQ ID NO: 56 (rat/human). In one aspect, the isolated nucleic acid encodes a functional chimeric mammalian C1qb polypeptide which is or comprises SEQ ID NO: 11 or SEQ ID NO: 56.

Also disclosed herein is an isolated nucleic acid encoding a chimeric mammalian C1qc polypeptide comprising a nucleic acid sequence encoding substantially the globular head domain of a human C1qc polypeptide, e.g., encoding the globular head domain of a human C1qc polypeptide or a fragment thereof. In one aspect, the isolated nucleic acid encoding chimeric mammalian C1qc polypeptide, wherein the nucleic acid encoding the chimeric mammalian C1qc polypeptide comprises at least a nucleic acid sequence encoding amino acids 118-234 of human C1qc polypeptide set forth in SEQ ID NO: 6. For example, the nucleic acid can comprise a nucleic acid sequence (e.g., a portion of human C1qa exon 3) encoding amino acids 114-245 of human C1qc polypeptide as set forth in SEQ ID NO: 6.

The nucleic acids encoding chimeric mammalian C1qc polypeptide may further comprise non-human nucleic acid sequences (such as, for example, a nucleic acid sequence encoding the substantially the N-terminal stalk-stem region of a non-human C1qc polypeptide). Thus, also disclosed herein is an isolated nucleic acid, wherein the nucleic acid sequence comprises at least a nucleotide sequence encoding amino acids 31-111, 30-113, or 30-114 of the mouse C1qc polypeptide set forth in SEQ ID NO: 3, or wherein the nucleic acid sequence comprises at least a nucleotide sequence encoding amino acids 33-113, 32-115, or 32-116 of the rat C1qc polypeptide set forth in SEQ ID NO: 9. In a particular aspect, disclosed herein is an isolated nucleic acid, wherein the isolated nucleic acid encodes at least amino acids 30-246 of the polypeptide set forth in SEQ ID NO: 12 (mouse/human) or wherein the isolated nucleic acid encodes at least amino acids 32-248 of the polypeptide set forth in SEQ ID NO: 57 (rat/human). In one aspect, the isolated nucleic acid encodes a functional chimeric mammalian C1qc polypeptide which is or comprises SEQ ID NO: 12 or SEQ ID NO: 57.

In some embodiments, the non-human nucleic acid sequence in an isolated nucleic acid encoding a chimeric C1q polypeptide also encodes a non-human signal peptide, e.g., the signal peptide of an endogenous non-human C1q polypeptide.

In some embodiments, the non-human nucleic acid sequence in an isolated nucleic acid encoding a chimeric C1q polypeptide also comprises a non-human 5' UTR region. e.g., the 5' UTR region of an endogenous non-human C1q gene.

In some embodiments, the human nucleic acid sequence in an isolated nucleic acid encoding a chimeric C1q polypeptide also comprises a human 3' UTR region, e.g., the 3' UTR region of a human C1q gene.

In some embodiments, the non-human nucleic acid sequence is a genomic fragment of a non-human C1q gene which comprises a coding portion of exon 2 (e.g., the portion that encodes amino acids of the mature form of the non-human C1q polypeptide) and a portion of exon 3 (e.g., the portion that encodes amino acids of the N-terminal stalk-stem region).

In some embodiments, the non-human nucleic acid sequence is a genomic fragment of a non-human C1q gene comprising the entire coding portion of exon 2 which encodes both the signal peptide and amino acids of the mature form of the non-human C1q polypeptide, and the portion of exon 3 that encodes amino acids of the N-terminal stalk-stem region. In some embodiments, the non-human nucleic acid sequence is a genomic fragment of a non-human C1q gene comprising exon 1, exon 2, and the portion of exon 3 that encodes amino acids of the N-terminal stalk-stem region, thereby encompassing the 5' UTR of the non-human C1q gene.

In some embodiments, the human nucleic acid sequence is a genomic fragment of a human C1q gene which comprises a portion of exon 3 that encodes the globular head domain or a fragment thereof of a human C1q polypeptide. The human nucleic acid sequence is operably linked to the non-human nucleic acid sequence such that the encoded chimeric C1q polypeptide comprises an N-terminal stalk-stem region that is substantially non-human and a globular head domain that is substantially human and is a functional C1q polypeptide.

In some embodiments, the human nucleic acid sequence is a genomic fragment of a human C1q gene comprising a 3' portion of exon 3 that encodes the globular head domain or a fragment thereof and includes the entire 3' UTR of the human C1q gene.

In one particular aspect, disclosed herein is an isolated nucleic acid encoding a chimeric non-human C1q protein, wherein the nucleic acid comprises a sequence encoding a chimeric C1qa, a chimeric C1qb, and/or a chimeric C1qc. In some embodiments, one or more of the sequence(s) encoding the chimeric C1qa, C1qb, and/or C1qc comprise a sequence encoding a human globular head domain or a fragment thereof. In some embodiments, one or more of the sequence(s) encoding the chimeric C1qa, C1qb, and/or C1qc comprise a sequence encoding non-human (e.g., rodent, e.g., rat or mouse) stem and/or stalk. In some embodiments, one or more of the sequence(s) encoding the chimeric C1qa, C1qb, and/or C1qc comprise a sequence encoding non-human (e.g., rodent, e.g., rat or mouse) collagen triple helix domain.

Thus, in some embodiments, disclosed herein is an isolated nucleic acid, wherein the isolated nucleic acid encodes a chimeric non-human mammal C1q protein, comprising one or more of a first, second or third nucleotide sequences, wherein the first nucleotide sequence encodes a chimeric non-human mammalian C1qa polypeptide, the second nucleotide sequence encodes a chimeric non-human mammalian C1qb polypeptide, and the third nucleotide sequence encodes a chimeric non-human mammalian C1qc polypeptide.

Figure 3A:
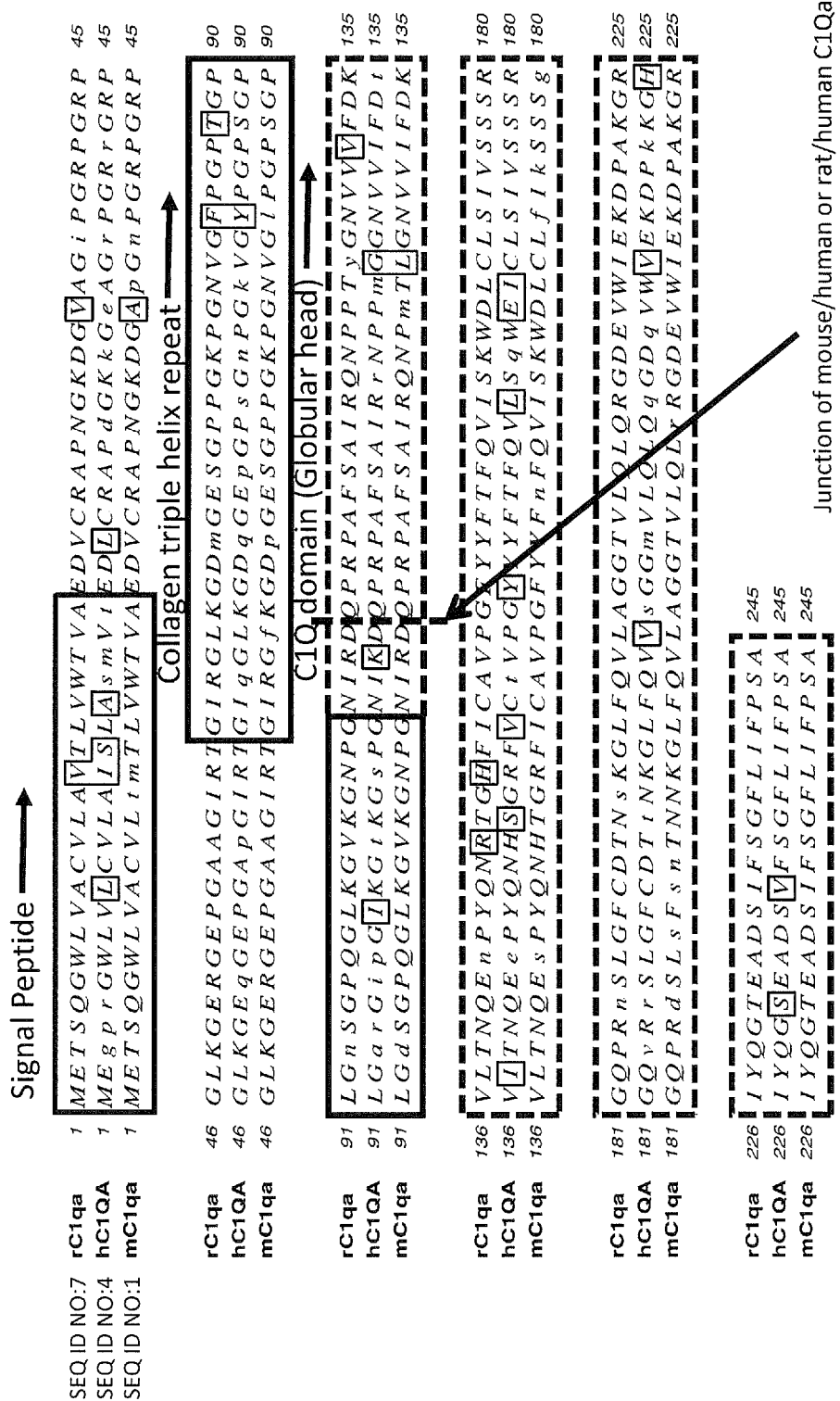
FIG. 3A shows C1qa amino acid alignments for rat (rC1qa), human (hC1QA), and mouse (mC1qa) polypeptides, with similarities being outlined and mismatches shown in lower cases. Signal peptide sequences are boxed and labeled. The collagen triple helix repeat sequences are boxed and labeled. The C1qa globular head domain sequences are boxed with dashed lines, and the junction of mouse/human or rat/human sequence in the chimeric polypeptides is depicted with a dashed line and indicated with an arrow.

In one embodiment, the disclosed isolated nucleic acids can further comprise a nucleotide sequence that encodes a human, a mouse or a rat C1qa, C1qb, and/or C1qc signal peptide as set forth in FIGS. 3A, 3B, and/or 3C.

Also disclosed herein is an isolated nucleic acid encoding a chimeric mammalian C1q polypeptide, wherein the non-human mammal nucleic acid sequence comprises exons 1 and 2 of the non-human mammal C1qa, C1qb, and/or C1qc gene.

It is understood and herein contemplated that the disclosed nucleic acids can be incorporated into a cell to be translated and expressed. Thus, any of the disclosed nucleic acids can be cloned into the genome of a cell for expression of the chimeric C1q polypeptide. Therefore, provided herein is a genetically modified cell comprising one or more isolated nucleic acids of any preceding aspect.

The term "cell" includes any cell that is suitable for expressing a recombinant nucleic acid sequence. Cells include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g., *S. cerevisiae, S. pombe, P. pastoris, P. methanolica*, etc.), plant cells, insect cells (e.g., SF-9, SF-21, baculovirus-infected insect cells, *Trichoplusia ni*, etc.), non-human animal cells, human cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21). Jurkat, Daudi, A431 (epidermal), CV-1, U937, 3T3. L cell, C127 cell, SP2/0, NS-0, MMT 060562, Sertoli cell, BRL 3A cell, HT1080 cell, myeloma cell, tumor cell, and a cell line derived from an aforementioned cell. In some embodiments, the cell comprises one or more viral genes, e.g. a retinal cell that expresses a viral gene (e.g., a PER.C6™ cell). In some embodiments, the cell is an ES cell. In other embodiments, the cell is a dendritic cell, a fibroblast, a epithelial cell, or a primary cell. In some embodiments, the cell is used to produce genetically modified non-human animals. It is further understood that some said cells can be incorporated into and used to develop a genetically modified non-human animal comprising any of the disclosed nucleic acids which at least encode one or more chimeric C1qa, C1qb, and/or C1qc polypeptides, and can express said polypeptides. In some embodiments, a cell is obtained from the genetically modified non-human animal provided herein. In some such embodiments, the cell may be a primary cell. In some embodiments, the cell may be a macrophage or a dendritic cell.

One skilled in the art would understand that in addition to the nucleic acid residues encoding humanized C1q proteins described herein, due to the degeneracy of the genetic code, other nucleic acids may encode the polypeptides of the present disclosure. Therefore, in addition to a genetically modified non-human animal that comprises in its genome nucleotide sequences encoding humanized C1q proteins described herein, a non-human animal that comprises in its genome nucleotide sequences that differ from those described herein due to the degeneracy of the genetic code are also provided.

There are a variety of sequences related to the protein C1q, for example the polypeptides C1qa, C1qb, and/or C1qc as well as chimeric C1qa, C1qb, and/or C1qc, or any of the nucleic acids disclosed herein for making chimeric C1qa, C1qb, and/or C1qc polypeptides, all of which are encoded by nucleic acids or are nucleic acids. The sequences for the human analogs of these genes, as well as other analogs, and alleles of these genes, and splice variants and other types of variants, are available in a variety of protein and gene databases, including Genbank. Those of skill in the art understand how to resolve sequence discrepancies and differences and to adjust the compositions and methods relating to a particular sequence to other related sequences.

E. Genetically Modified Humanized C1q Animals

In a further aspect, provided herein is a genetically modified non-human animal (e.g., rodent such as mouse or rat) that expresses a chimeric, humanized C1q polypeptide (e.g., a chimeric C1qa, C1qb or C1qc) as described hereinabove. Such non-human animal expresses a humanized C1q complex comprising the humanized C1q polypeptide.

In one aspect, disclosed herein are non-human animals (e.g., rodent such as mouse or rat) that comprise in their genome a nucleic acid molecule encoding a chimeric C1q polypeptide described hereinabove, e.g., a chimeric C1q polypeptide (C1qa, C1qb, or C1qc) comprising an N-terminal stalk-stem region that is substantially non-human (endogenous) and a globular head domain that is substantially human.

In some embodiments, the animal disclosed herein comprises a nucleic acid molecule encoding a chimeric C1q polypeptide (e.g., C1qa, C1qb or C1qc polypeptide) as described hereinabove, wherein the nucleic acid molecule comprises non-human (e.g., endogenous) and human nucleic acid sequences.

In some embodiments, the nucleic acid molecule encoding a chimeric C1q polypeptide includes a non-human (e.g., endogenous) C1q nucleic acid sequence and a cognate human C1q nucleic acid sequence, operably linked to each other such that the nucleic acid molecule encodes a functional C1q polypeptide. The term "cognate" is used herein in the context of a chimeric molecule to indicate that the sequences in the chimeric molecule that are of different origins correspond to the same gene. For example, a mouse or rat C1qa sequence is linked to a human C1qa sequence to form a chimeric C1qa molecule, a mouse or rat C1qb sequence is linked to a human C1qb sequence to form a chimeric C1qb molecule, a mouse or rat C1qc sequence is linked to a human C1qc sequence to form a chimeric C1qc molecule. In some embodiments, the chimeric C1q polypeptide comprises an N-terminal stalk-stem region that is substantially non-human and a globular head domain that is substantially human.

In some embodiments, the nucleic acid molecule encoding a chimeric C1q polypeptide in the genome of a genetically modified non-human animal includes a non-human C1q nucleic acid sequence (e.g., an endogenous non-human C1q nucleic acid sequence) and a human C1q nucleic acid sequence, wherein the human C1q nucleic acid sequence encodes substantially the globular head domain of a human C1q polypeptide.

In some embodiments, the nucleic acid molecule encoding a chimeric C1q polypeptide in the genome of a genetically modified non-human animal includes a non-human (e.g., endogenous) C1q nucleic acid sequence and a human C1q nucleic acid sequence, wherein the non-human C1q nucleic acid sequence encodes substantially the N-terminal stalk-stem region of a non-human (e.g., endogenous) C1q polypeptide.

In some embodiments, the nucleic acid molecule encoding a chimeric C1q polypeptide is operably linked to a 5' regulatory element(s), such as the promoter and/or enhancer(s), of a non-human (e.g., endogenous) C1q gene.

In some embodiments, the nucleic acid molecule encoding a chimeric C1q polypeptide in the genome is at a locus other than an endogenous C1q locus.

In some embodiments, the chimeric C1q nucleic acid molecule in the genome is at an endogenous C1q locus. In some such embodiments, the chimeric C1q nucleic acid molecule in the genome can result from a replacement of a nucleotide sequence of an endogenous C1q gene at its endogenous locus with a nucleotide sequence of a cognate human C1q gene.

In some embodiments, a contiguous genomic sequence of a non-human C1q gene at an endogenous C1q locus has been replaced with a contiguous genomic sequence of a cognate human C1q gene to form a chimeric, humanized C1q gene.

In some embodiments, a contiguous genomic sequence of a human C1q gene inserted into an endogenous non-human C1q gene includes a portion of exon 3 of the human C1q gene such that the resulting chimeric, humanized C1q gene encodes a chimeric C1q polypeptide comprising a globular head domain that is substantially human. In some embodiments, a contiguous genomic sequence of a human C1q gene inserted into an endogenous non-human C1q gene includes a portion of exon 3 of the human C1q gene that encodes substantially the globular head domain the human C1q polypeptide.

In some embodiments, the genomic sequence of an endogenous C1q gene that remains at an endogenous locus after the humanization and is operably linked to the inserted contiguous human C1q genomic sequence, includes a 3' portion of exon 2 and a 5' portion of exon 3, and encodes substantially the N-terminal stalk-stem region of the endogenous C1q polypeptide.

In circumstances where a non-human C1q polypeptide and a cognate human C1q polypeptide share common amino acids near the junction between the stalk-stem region and the globular head domain, it may not be necessary to insert a human C1q nucleic acid that encodes precisely the globular head domain of the human C1q polypeptide. It is possible to insert a slightly longer or shorter nucleic acid of a human C1q gene that encodes substantially the globular head domain of the human C1q polypeptide, in operable linkage to a nucleic acid that encodes substantially the stalk-stem region of the non-human animal C1q polypeptide, such that the chimeric C1q polypeptide includes a globular head domain that is substantially or fully identical to the globular head domain of the human C1q polypeptide, and a stalk-stem region that is substantially or fully identical to stalk-stem region of the non-human C1q polypeptide. Similarly, in circumstances where a non-human C1q polypeptide and a human C1q polypeptide share common amino acids near the C-terminus of the globular head domain, it may not be necessary to utilize a human C1q nucleic acid that encodes precisely the globular head domain of the human C1q polypeptide. It is possible to insert a slightly shorter nucleic acid of a human C1q gene that encodes substantially (i.e., slightly shorter than) the globular head domain of the human C1q polypeptide, in operable linkage to a non-human nucleic acid that encodes the remainder of amino acids at the C-terminus of the globular head domain, such that the chimeric C1q polypeptide includes a globular head domain that is still substantially or fully identical to the globular head domain of the human C1q polypeptide.

In some embodiments, the human C1q nucleotide sequence included in a humanized, chimeric C1q gene also includes the 3' untranslated region ("UTR") of the human C1q gene, which is the last part of exon 3 in all C1q genes (i.e., C1qa, C1qb and C1qc genes). In certain embodiments, in addition to the 3' UTR of a human C1q gene, an additional human genomic sequence from the human C1q gene locus can also be included. The additional human genomic sequence can consist of at least 10-200 bp, e.g., 50 bp, 75 bp, 100 bp, 125 bp, 150 bp, 175 bp, 200 bp, or more, found in the human C1q gene locus immediately downstream of the 3' UTR of the human C1q gene. In other embodiments, the human C1q nucleotide sequence included in a humanized C1q gene does not include the 3' UTR of the human C1q gene; instead, the 3' UTR of an endogenous C1q gene is included and follows immediately the stop codon of the humanized C1q gene.

In some embodiments, the endogenous non-human C1q nucleic acid sequence included in a humanized, chimeric C1q gene (e.g., the endogenous genomic C1q sequence remaining at an endogenous locus after humanization) includes the 5' UTR of endogenous C1q gene (which may include exon 1 and in most cases a 5' portion of exon 2). In some embodiments, the endogenous non-human C1q nucleotide sequence included in a humanized, chimeric C1q gene also includes a nucleotide sequence (e.g., a 5' portion of exon 2) coding for the signal peptide of the endogenous C1q polypeptide.

In some embodiments, a non-human animal provided herein is heterozygous for a humanized C1q gene in its genome. In other embodiments, a non-human animal provided herein is homozygous for a humanized C1q gene in its genome.

In certain embodiments, a non-human animal includes multiple, i.e., two or more, chimeric C1q genes in its genome, each at an endogenous C1q locus or a different locus. In some embodiments, the multiple chimeric C1q genes are on a contiguous nucleic acid fragment at a non-endogenous C1q locus. In some embodiments, the multiple chimeric C1q genes are each at its endogenous C1q locus. For example, two or all three endogenous C1q genes (C1qa, C1qb and C1qc) in a non-human animal have been humanized using nucleotide sequences of cognate human C1q genes.

In various embodiments provided, the genetically modified non-human animal expresses the polypeptide(s) encoded by the chimeric non-human/human C1q nucleic acid molecules. Thus, disclosed herein is a genetically modified non-human animal, wherein the non-human animal expresses one or more chimeric non-human/human C1qa, C1qb, and/or C1qc polypeptides. In such an aspect, the genetically modified non-human animals can express one, two, three, four, five, or six chimeric non-human/human C1qa polypeptides, one, two, three, four, five, or six chimeric non-human/human C1qb polypeptides, and/or one, two, three, four, five, or six chimeric non-human/human C1qc polypeptides. In various embodiments, the expressed chimeric C1q polypeptides are functional C1q polypeptides. In various embodiments, the C1q polypeptides provided herein arrange in a typical C1q bouquet structure to form a functional C1q protein comprising 18 polypeptide chains.

In some embodiments, the non-human animal does not express a functional endogenous C1q polypeptide (e.g., an endogenous C1qa, C1qb or C1qc polypeptide). In some embodiments, the non-human animal does not express a functional endogenous C1qa polypeptide, a functional endogenous C1qb polypeptide, or a functional endogenous C1qc polypeptide. The lack of expression of a functional endogenous C1q polypeptide(s) can be a result of inactivation, deletion, and/or humanization of the endogenous C1q gene(s).

In some aspects, the non-human animal expresses one or more chimeric C1qa, C1qb, and/or C1qc polypeptides comprising the globular head domains of human C1qa, C1qb, and/or C1qc polypeptides. In some aspects, the non-human animal expresses a chimeric C1qa polypeptide comprising an globular head domain of human C1qa set forth in SEQ ID NO: 4 or a fragment thereof (for example, amino acids 112-245, 122-235 or 122-222 as set forth in SEQ ID NO: 4). In some aspects, the non-human animal expresses a chimeric C1qb polypeptide comprising a globular head domain of human C1qb set forth in SEQ ID NO: 5 or a fragment thereof (for example, amino acids 118-251, 120-251 or 125-233 as set forth in SEQ ID NO: 5). In some aspects, the non-human animal expresses a chimeric C1qc polypeptide comprising a globular head domain of human C1qc set forth in SEQ ID NO: 6 or a fragment thereof (for example, amino acids 118-234 or amino acids 114-245 as set forth in SEQ ID NO: 6). In some aspects, the non-human animal expresses the chimeric C1qa as set forth in SEQ ID NOs: 10 or 55, C1qb as set forth in SEQ ID NOs: 11 or 56, and/or C1qc polypeptide as set forth in SEQ ID NOs: 12 or 57.

In one aspect, it is understood and herein contemplated that the disclosed genetically modified non-human animals comprise nucleic acids encoding C1q polypeptides that comprise non-human amino acid sequences and human amino acid sequences. It is further understood that all or a portion of the globular head domain of chimeric C1q is comprised of human amino acid sequences. In one aspect, disclosed herein is a genetically modified non-human animal (such as, for example a rodent such as a mouse or rat), wherein the nucleic acid sequence encoding the globular head of a human C1qa polypeptide or a fragment thereof encodes at least amino acids 122-222 of the human C1qa polypeptide as set forth in SEQ ID NO: 4 (for example, a nucleic acid sequence encoding amino acids 122-235 or 112-245 of the human C1qa polypeptide as set forth in SEQ ID NO: 4). In one aspect, the genetically modified non-human animal is a rat and further comprises, operably linked to the nucleic acid sequence encoding the globular head domain or the fragment thereof of the human C1qa polypeptide, a nucleotide sequence encoding at least amino acids 33-102, 30-102, 25-105, 23-107 or 23-111 of the rat C1qa polypeptide set forth in SEQ ID NO: 7, or the genetically modified non-human animal is a mouse and further comprises, operably linked to the nucleic acid sequence encoding the globular head domain or the fragment thereof of the human C1qa polypeptide, a nucleotide sequence encoding at least amino acids 33-102, 30-102, 25-105, 23-107 or 23-111 of the mouse C1qa polypeptide set forth in SEQ ID NO: 1. In one aspect, the genetically modified non-human animals comprise one or more nucleic acid sequences encoding at least amino acids 23-245 of a C1qa polypeptide as set forth in SEQ ID NO: 10 or SEQ ID NO: 55. In a specific aspect, disclosed herein are genetically modified non-human animals (such as, for example a rodent such as a mouse or rat), wherein the non-human animal comprises one or more nucleic acid sequences encoding a C1qa polypeptide as set forth in SEQ ID NO: 10 or SEQ ID NO: 55. In some embodiments, a genetically modified non-human animal is a mouse that comprises a nucleic acid encoding a C1qa polypeptide as set forth in SEQ ID NO: 10. In some embodiments, a genetically modified non-human animal is a rat that comprises a nucleic acid encoding a C1qa polypeptide as set forth in SEQ ID NO: 55.

In another aspect, disclosed herein is a genetically modified non-human animal (such as, for example a rodent such as a mouse or rat), wherein the nucleic acid sequence encoding the globular head of a human C1qb polypeptide or a fragment thereof encodes at least amino acids 125-233 of the human C1qb polypeptide as set forth in SEQ ID NO: 5 (for example, a nucleic acid sequence encoding amino acids 120-250 or 118-251 of the human C1qb polypeptide).

Also disclosed herein is a genetically modified non-human animal (such as, for example a rodent such as a mouse or rat) wherein the genetically modified non-human animal is a rat and comprises, operably linked to the nucleic acid sequence encoding the globular head domain or the fragment thereof of the human C1qb polypeptide, a nucleotide sequence encoding at least amino acids 32-105, 27-105, 27-110, 26-114, or 26-117 of the rat C1qb polypeptide set forth in SEQ ID NO: 8, or wherein the genetically modified non-human animal is a mouse and further comprises, operably linked to the nucleic acid sequence encoding the globular head domain or the fragment thereof of the human C1qb polypeptide, a nucleotide sequence encoding at least amino acids 32-105, 27-105, 27-110, 26-114, or 26-117 of the mouse C1qb polypeptide set forth in SEQ ID NO: 2.

In one aspect, the genetically modified non-human animal comprises one or more nucleic acid sequences encoding at least amino acids 26-251 of a C1qb polypeptide as set forth in SEQ ID NO: 11 or SEQ ID NO: 56. In a specific aspect, disclosed herein is a genetically modified non-human animal (such as, for example a rodent such as a mouse or rat), wherein the non-human animal comprises one or more nucleic acid sequences encoding a C1qb polypeptide as set forth in SEQ ID NO: 11 or SEQ ID NO: 56. In some embodiments, a genetically modified non-human animal is a mouse that comprises a nucleic acid encoding a C1qb polypeptide as set forth in SEQ ID NO: 11. In some embodiments, a genetically modified non-human animal is a rat that comprises a nucleic acid encoding a C1qb polypeptide as set forth in SEQ ID NO: 56.

In one aspect, the genetically modified non-human animal (such as, for example a rodent such as a mouse or rat) comprises a nucleic acid, wherein the nucleic acid sequence encoding the globular head of a human C1qc polypeptide or a fragment thereof encodes at least amino acids 118-234 of the human C1qc polypeptide as set forth in SEQ ID NO: 6 (for example, a nucleic acid sequence encoding amino acids 114-245 of the human C1qc polypeptide).

Also disclosed herein is a genetically modified non-human animal (such as, for example a rodent such as a mouse or rat), wherein the non-human animal is a rat and further comprises, operably linked to the nucleic acid sequence encoding the globular head domain or the fragment thereof of the human C1qc polypeptide, a nucleotide sequence encoding at least amino acids 33-113, 32-115, or 32-116 of the rat C1qc polypeptide set forth in SEQ ID NO: 9, or wherein the non-human animal is a mouse and further comprises, operably linked to the nucleic acid sequence encoding the globular head domain or the fragment thereof of the human C1qc polypeptide, a nucleotide sequence encoding at least amino acids 31-111, 30-113, or 30-114 of the mouse C1qc polypeptide set forth in SEQ ID NO: 3.

In one aspect, the genetically modified non-human animal comprises one or more nucleic acid sequences encoding at least amino acids 30-246 of a C1qc polypeptide as set forth in SEQ ID NO: 12 or one or more nucleic acid sequences encoding at least amino acids 32-248 of a C1qc polypeptide as set forth in SEQ ID NO: 57. In a specific aspect, disclosed herein is a genetically modified non-human animal (such as, for example a rodent such as a mouse or rat), wherein the non-human animal comprises one or more nucleic acid sequences encoding a C1qc polypeptide as set forth in SEQ ID NO: 12 or SEQ ID NO: 57. In some embodiments, a genetically modified non-human animal is a mouse that comprises a nucleic acid encoding a C1qc polypeptide as set forth in SEQ ID NO: 12. In some embodiments, a genetically modified non-human animal is a rat that comprises a nucleic acid encoding a C1qb polypeptide as set forth in SEQ ID NO: 57.

In some aspect, it is beneficial for the expression of a polypeptide for a signal sequence to be present. The disclosed polypeptides and disclosed nucleic acids encoding said polypeptides can comprise signal sequences or have signal sequences absent. Thus, in one aspect, disclosed herein is a genetically modified non-human animal (such as, for example a rodent such as a mouse or rat) wherein the non-human animal further comprises, in operable linkage, a nucleotide sequence encoding a rat, a mouse or a human C1qa, C1qb, and/or C1qc signal peptide. Examples of signal peptides from rat, mouse and human C1qa, C1qb, and C1qc polypeptides are shown in FIGS. 3A-3C. For example, disclosed herein is a non-human animal comprising, in operable linkage, a nucleic acid sequence comprising a signal peptide-encoding portion of the rat or mouse C1qa, C1qb, and/or C1qc gene, and at least the nucleic acid sequence encoding the globular head domain or the fragment thereof of the human C1qa, C1qb, and/or C1qc polypeptide, respectively.

In one aspect, disclosed herein is a genetically modified non-human animal (such as, for example a rodent such as a mouse or rat) comprising in its genome a) at the endogenous C1qa locus a nucleic acid sequence encoding a chimeric rat/human C1qa polypeptide wherein the nucleic acid sequence comprises, 5'-3' and in operable linkage a first nucleotide sequence encoding amino acids 1-111 of a rat C1qa polypeptide of SEQ ID NO: 7 and a second nucleotide sequence encoding amino acids 112-245 of a human C1qa polypeptide of SEQ ID NO: 4: b) at the endogenous C1qb locus a nucleic acid sequence encoding a chimeric rat/human C1qb polypeptide wherein the nucleic acid sequence comprises, 5'-3' and in operable linkage a third nucleotide sequence encoding amino acids 1-117 of a rat C1qb polypeptide of SEQ ID NO: 8 and a fourth nucleotide sequence encoding amino acids 118-251 of a human C1qb polypeptide of SEQ ID NO: 5; and c) at the endogenous C1qc locus a nucleic acid sequence encoding a chimeric rat/human C1qc polypeptide wherein the nucleic acid sequence comprises, 5'-3' and in operable linkage a fifth nucleotide sequence encoding amino acids 1-116 of a rat C1qc polypeptide of SEQ ID NO: 9 and a sixth nucleotide sequence encoding amino acids 114-245 of a human C1qc polypeptide of SEQ ID NO: 6. In one embodiment, such genetically modified non-human animal is a rat.

Also disclosed herein is a genetically modified non-human animal (such as, for example a rodent such as a mouse or rat) comprising in its genome a) at the endogenous C1qa locus a nucleic acid sequence encoding a chimeric mouse/human C1qa polypeptide wherein the nucleic acid sequence comprises, 5'-3' and in operable linkage a first nucleotide sequence encoding amino acids 1-111 of a mouse C1qa polypeptide of SEQ ID NO: 1 and a second nucleotide sequence encoding amino acids 112-245 of a human C1qa polypeptide of SEQ ID NO: 4; b) at the endogenous C1qb locus a nucleic acid sequence encoding a chimeric mouse/human C1qb polypeptide wherein the nucleic acid sequence comprises, 5'-3' and in operable linkage a third nucleotide sequence encoding amino acids 1-117 of a mouse C1qb polypeptide of SEQ ID NO: 2 and a fourth nucleotide sequence encoding amino acids 118-251 of a human C1qb polypeptide of SEQ ID NO: 5; and c) at the endogenous C1qc locus a nucleic acid sequence encoding a chimeric mouse/human C1qc polypeptide wherein the nucleic acid sequence comprises, 5'-3' and in operable linkage a fifth nucleotide sequence encoding amino acids 1-114 of a mouse C1qc polypeptide of SEQ ID NO: 3 and a sixth nucleotide sequence encoding amino acids 114-245 of a human C1qc polypeptide of SEQ ID NO: 6. In one embodiment, such genetically modified non-human animal is a mouse.

In one aspect disclosed herein is a genetically modified non-human animal, wherein the non-human animal, e.g., the rat or the mouse, does not express a functional endogenous C1qa, C1qb, and/or C1qc polypeptide(s).

In some embodiments, the non-human animal is a mammal. In one aspect, the non-human animal is a small mammal, e.g., of the superfamily Dipodoidea or Muroidea. In one embodiment, the genetically modified animal is a rodent. In one embodiment, the rodent is selected from a mouse, a rat, and a hamster. In one embodiment, the rodent is selected from the superfamily Muroidea. In one embodiment, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, white-tailed rats, Malagasy rats and mice), Platacanthomyidae (e.g., spiny dormice), and Spalacidae (e.g., mole rats, bamboo rats, and zokors). In a specific embodiment, the genetically modified rodent is selected from a true mouse or rat (family Muridae), a gerbil, a spiny mouse, and a crested rat. In one embodiment, the genetically modified mouse is from a member of the family Muridae. In one embodiment, the animal is a rodent. In a specific embodiment, the rodent is selected from a mouse and a rat. In one embodiment, the non-human animal is a mouse.

In one embodiment, the non-human animal is a rodent that is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In another embodiment, the mouse is a 129 strain selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129S6 (129/SvEvTac), 129S7, 129S8, 129T1, 129T2 (see, e.g., Festing et al. (1999) Revised nomenclature for strain 129 mice, Mammalian Genome 10:836, see also, Auerbach et al (2000) Establishment and Chimera Analysis of 129/SvEv- and C57BL/6-Derived Mouse Embryonic Stem Cell Lines). In a specific embodiment, the genetically modified mouse is a mix of an aforementioned 129 strain and an aforementioned C57BL/6 strain. In another specific embodiment, the mouse is a mix of aforementioned 129 strains, or a mix of aforementioned BL/6 strains. In a specific embodiment, the 129 strain of the mix is a 129S6 (129/SvEvTac) strain. In another embodiment, the mouse is a BALB strain, e.g., BALB/c strain. In yet another embodiment, the mouse is a mix of a BALB strain and another aforementioned strain.

In one embodiment, the non-human animal is a rat. In one embodiment, the rat is selected from a Wistar rat, an LEA strain, a Sprague Dawley strain, a Fischer strain, F344, F6, and Dark Agouti. In one embodiment, the rat strain is a mix of two or more strains selected from the group consisting of Wistar, LEA, Sprague Dawley, Fischer, F344, F6, and Dark Agouti.

In some embodiments, a genetically engineered animal disclosed herein expresses in its serum a humanized C1q protein comprising one or more chimeric C1q polypeptides. In specific embodiments, the animal expresses in its serum a C1q protein composed of chimeric C1qa, C1qb and C1qc polypeptides, each of which comprises a globular head domain that is substantially human. In some embodiments, the level of a humanized C1q protein in the serum of a genetically engineered animal is comparable to the level of the C1q protein in a control animal without the humanization, as detected by any of conventional assays such as Western Blot or ELISA. By "comparable" it is meant to refer to level and values within a variation of e.g., 10%, 20%, 30%, or 40%.

In some embodiments, a genetically engineered animal expressing a humanized C1q protein in its serum displays complement activity. In some embodiments, the complement activity is detectable by a classical hemolysis assay, as further illustrated in the examples below. In specific embodiments, the genetically engineered animal displays classical hemolytic activity in its serum at a level comparable to the level in a control animal without the humanization. In other embodiments, the complement activity is detectable in an in vitro complement-dependent cytotoxicity (CDC) assay. In specific embodiments, the serum of a genetically engineered animal comprising a humanized C1q protein displays CDC activity at a level comparable to that of normal human serum.

In a further aspect, provided herein are methods of making the genetically modified non-human animal described herein.

In some embodiments, the method comprises modifying the genome of a non-human animal such that the modified genome comprises a nucleic acid molecule encoding a humanized C1q polypeptide (i.e., a humanized C1qa, C1qb, and/or C1qc polypeptide).

In some embodiments, the modified genome comprises a nucleic acid encoding a chimeric C1q polypeptide, wherein the nucleic acid is located at a locus different from an endogenous C1q locus. In certain embodiments, a contiguous nucleic acid fragment comprising multiple nucleic acid molecules encoding different humanized C1q polypeptides is located at a locus different from an endogenous C1q locus. For example, a contiguous nucleic acid fragment comprising a nucleic acid sequence encoding a humanized C1qa polypeptide, a nucleic acid sequence encoding a humanized C1qb polypeptide, and a nucleic acid sequence encoding a humanized C1qc polypeptide, is located at a locus different from the endogenous C1q locus.

In some embodiments, the modified genome comprises a nucleic acid encoding a chimeric C1q polypeptide wherein the nucleic acid is located at an endogenous C1q locus. In certain embodiments, a contiguous nucleic acid fragment comprising a nucleic acid sequence encoding a humanized C1qa polypeptide, a nucleic acid sequence encoding a humanized C1qb polypeptide, and a nucleic acid sequence encoding a humanized C1qc polypeptide, is located at an endogenous C1q locus.

The modification to introduce a nucleic acid encoding a chimeric C1q polypeptide into an endogenous C1q locus can, in some embodiments, result in replacement of an endogenous C1q nucleotide sequence with a human C1q nucleotide sequence. In one embodiment, the replacement comprises the replacement of sequences of C1qa, C1qb, and C1qc.

Humanization may be accomplished by creating a large targeting vector that incorporates a genetic modification, e.g., a genetic modification in one, two or all three C1q loci and then introducing the large targeting vector into non-human (e.g., rodent such as mouse or rat) ES cells to make a non-human animal such as a mouse, e.g., as described in Example 1, or a rat, e.g., as described in Example 2.

Thus, in one embodiment, provided herein is a large targeting vector for making a genetically modified animal of the present disclosure. In an exemplary embodiment, the large targeting vector comprises 5' and 3' mouse homology arms; a DNA fragment comprising the C1qa gene which comprises a replacement of partial sequence of mouse C1qa coding exon 3 with partial sequence of human C1qa coding exon 3; a DNA fragment comprising the C1qb gene which comprises a replacement of partial sequence of mouse C1qb coding exon 3 with partial sequence of human C1qb coding exon 3; a DNA fragment comprising the C1qc gene which comprises a replacement of partial sequence of mouse C1qc coding exon 3 with partial sequence of human C1qc coding exon 3; and a selection cassette. In another exemplary embodiment, the large targeting vector comprises 5' and 3' rat homology arms; a DNA fragment comprising the C1qa gene which comprises a replacement of partial sequence of rat C1qa coding exon 3 with partial sequence of human C1qa coding exon 3; a DNA fragment comprising the C1qb gene which comprises a replacement of partial sequence of rat C1qb coding exon 3 with partial sequence of human C1qb coding exon 3; a DNA fragment comprising the C1qc gene which comprises a replacement of partial sequence of rat C1qc coding exon 3 with partial sequence of human C1qc coding exon 3; and a selection cassette.

In some embodiments, a large targeting vector is a genetically modified bacterial artificial chromosome (BAC) clone. A BAC clone carrying one or more of non-human (e.g., rodent) C1qa, C1qb and C1qc genes can be modified and humanized using bacterial homologous recombination and VELOCIGENE® technology (see, e.g., U.S. Pat. No. 6,586,251 and Valenzuela et al. (2003). High-throughput engineering of the mouse genome coupled with high-resolution expression analysis. *Nature Biotech.* 21(6):652-659). In embodiments where the BAC clone comprises more than one non-human C1q gene (e.g., a combination of non-human C1qa, C1qb and C1qc genes), the multiple non-human C1q genes can be sequentially modified through serial bacterial homologous recombination. As a result, a non-human C1q nucleotide sequence has been deleted from the original BAC clone, and a human C1q nucleotide sequence has been inserted, resulting in a modified BAC clone carrying one or more humanized C1q genes, flanked by 5' and 3' non-human homology arms.

A selection cassette is a nucleotide sequence inserted into a targeting construct to facilitate selection of cells (e.g., bacterial cells, ES cells) that have integrated the construct of interest. A number of suitable selection cassettes are known in the art (Neo, Hyg, Pur, CM, SPEC, etc.). In addition, a selection cassette may be flanked by recombination sites, which allow deletion of the selection cassette upon treatment with recombinase enzymes. Commonly used recombination sites are loxP and Frt, recognized by Cre and Flp enzymes, respectively, but others are known in the art. A selection cassette may be located anywhere in the construct outside the coding region. In one embodiment, the selection cassette is inserted upstream of an inserted human C1qa sequence.

The large targeting vector, such as a modified BAC clone can be introduced into non-human (e.g., rodent) embryonic stem (ES) cells by known techniques, e.g., electroporation. Both mouse ES cells and rat ES cells have been described in the art. See, e.g., U.S. Pat. Nos. 7,576,259, 7,659,442, 7,294,754, and US 2008-0078000 A1 (all of which are incorporated herein by reference) describe mouse ES cells and the VELOCIMOUSE® method for making a genetically modified mouse; US 2014/0235933 A1, US 2014/0310828 A1. Tong et al. (2010) *Nature* 467:211-215, and Tong et al. (2011) *Nat Protoc.* 6(6): doi: 10.1038/nprot.2011.338 (all of which are incorporated herein by reference) describe rat ES cells and methods for making a genetically modified rat. In some embodiments, the recipient ES cell to which a modified BAC clone is to be introduced comprises a deletion of a nucleotide sequence at an endogenous C1q locus. In some embodiments, the deletion comprises the coding region of one or more of the C1qa, C1qb and C1qc genes. In specific embodiments, the deletion comprises the coding regions of all of the C1qa, C1qb and C1qc genes; for example, a deletion that comprises the start codon of C1qa through the stop codon of C1qb. In some embodiments, the recipient ES cell is heterozygous for a deletion at an endogenous C1q locus. In other embodiments, the recipient ES cell is homozygous for a deletion at an endogenous C1q locus.

Upon completion of gene targeting, ES cells or genetically modified non-human animals are screened to confirm successful incorporation of exogenous nucleotide sequence of interest or expression of exogenous polypeptide. Numerous techniques are known to those skilled in the art, and include (but are not limited to) Southern blotting, long PCR, quantitative PCR (e.g., real-time PCR using TAQMAN™), fluorescence in situ hybridization, Northern blotting, flow cytometry. Western analysis, immunocytochemistry, immunohistochemistry, etc. In one example, non-human animals (e.g., mice) bearing the genetic modification of interest can be identified by screening for loss of mouse allele and/or gain of human allele using a modification of allele assay described in Valenzuela et al. (2003) High-throughput engineering of the mouse genome coupled with high-resolution expression analysis, Nature Biotech. 21(6):652-659. Other assays that identify a specific nucleotide or amino acid sequence in the genetically modified animals are known to those skilled in the art. Selected ES cells are then used as donor ES cells for injection into a pre-morula stage embryo (e.g., 8-cell stage embryo) by using the VELOCIMOUSE® method (see, e.g., U.S. Pat. No. 7,576,259. U.S. Pat. Nos. 7,659,442, 7,294,754, and US 2008-0078000 A1), or methods described in US 2014/0235933 A1 and US 2014/0310828 A1. The embryo comprising the donor ES cells is incubated until blastocyst stage and then implanted into a surrogate mother to produce an F0 rodent. Pups bearing the humanized C1q gene can be identified by genotyping of DNA isolated from tail snips using loss of non-human allele and/or gain of human allele assays. Non-human animals heterozygous for a humanized C1q gene can be crossed to generated homozygous offersprings.

In one aspect, a method for making a chimeric human/non-human C1q molecule is provided, comprising expressing in a single cell a chimeric C1q protein from a nucleotide construct as described herein. In one embodiment, the nucleotide construct is a viral vector; in a specific embodiment, the viral vector is a lentiviral vector. In one embodiment, the cell is selected from a CHO, COS, 293, HeLa, and a retinal cell expressing a viral nucleic acid sequence (e.g., a PERC.6™ cell).

In one aspect, a cell that expresses a chimeric human/non-human C1q protein is provided. In one embodiment, the cell comprises an expression vector comprising a chimeric C1q sequence as described herein. In one embodiment, the cell is selected from CHO, COS, 293, HeLa, and a retinal cell expressing a viral nucleic acid sequence (e.g., a PERC.6™ cell).

A chimeric C1q molecule made by a non-human animal as described herein is also provided, wherein, in one embodiment, the chimeric C1q molecule comprises an amino acid sequence of all or substantially all of a globular head domain of a human C1qa, C1qb, and/or C1qc polypeptides, and at least stem and/or stalk domains from a non-human C1q protein, e.g., mouse C1q protein.

In addition to a genetically engineered non-human animal, a non-human embryo (e.g., a rodent, e.g., a mouse or a rat embryo) is also provided, wherein the embryo comprises a donor ES cell that is made as disclosed hereinabove or is derived from a non-human animal (e.g., a rodent, e.g., a mouse or a rat) as described herein. In one aspect, the embryo comprises an ES donor cell that comprises a chimeric C1q gene, and host embryo cells.

Also provided is a tissue, wherein the tissue is derived from a non-human animal (e.g., a rodent, e.g., a mouse or a rat) as described herein, and expresses a chimeric C1q protein. In some embodiments, a tissue is selected from blood, plasma, serum, bone marrow, spleen, lymph nodes, brain, and a combination thereof.

In addition, a non-human cell isolated from a non-human animal as described herein is provided. In one embodiment, the cell is an ES cell. In one embodiment, the cell is a dendritic cell.

F. Rodent Model for Testing Human Therapies

C1q molecules are being studied as targets for bispecific agents, e.g., bispecific antibodies, with one arm binding human C1q and another binding an antigen of interest.

During preclinical drug development stage, candidate agents are typically studied based on their efficacy, toxicity, and other pharmacokinetic and pharmacodynamics properties. Candidate agents, such as antibodies, typically target a human antigen—as the end goal of investigation is to develop a human therapy. Many preclinical studies are conducted in large animals such as primates as their physiology and drug metabolism are most similar to humans. To conduct effective preclinical investigations relating to efficacy, toxicity, and other parameters of a drug candidate, first, the drug candidate must be determined to recognize primate C1q molecule.

However, a separate factor complicating development of anti-C1q therapy is that large primates such as chimpanzees are endangered and in many countries studies in chimpanzees are prohibited; while studies in other primates, e.g., cynomolgus monkeys (*Macaca fascicularis*), may raise ethical concerns. Thus, any preliminary data on a specific therapeutic candidate that can be obtained in a smaller animal model, such as a rodent, e.g., a mouse, can be helpful in determining further progress of preclinical investigations in large primates.

The most useful small animal model to conduct preliminary studies is a non-human animal, e.g., a rodent, that expresses a human or humanized C1q protein, and allows the testing of anti-C1q drug candidates that also target, for example a tumor antigen, viral antigen, or bacterial antigen (such, as for example, a *Staphylococcus* antigen).

Accordingly, in some aspects, provided herein is a rodent model (such as, for example, a mouse or rat model) for testing C1q-targeted ("anti-C1q") therapeutic agents. In some embodiments, provided herein is a rodent model (such as, for example, a mouse or rat model) for testing anti-C1q antigen-binding proteins. In some embodiments, provided herein is a rodent model (such as, for example, a mouse or rat model) for testing anti-C1q antibodies. In some such embodiments, provided is a rodent model for testing anti-C1q multi-specific, e.g. bispecific, antigen-binding proteins or anti-C1q bispecific antibodies. As such, an anti-C1q multi-specific antigen-binding protein, e.g. an anti-C1q bispecific antigen-binding protein, targets or specifically binds said humanized C1q polypeptide or humanized C1q complex and at least one other antigen of interest. In various aspects, the rodent model for testing anti-C1q bispecific antigen-binding proteins wherein the antigen-binding protein is capable of binding both a humanized C1q complex (with one or more C1qa, C1qb, and/or C1qc polypeptides of the complex being humanized) and the antigen of interest comprises a nucleic acid sequence encoding a humanized C1q complex, wherein the humanized C1q polypeptide is selected from the group consisting of C1qa, C1qb, C1qc, and/or a combination thereof, and a cell expressing or comprising the antigen of interest. In one embodiment, the rodent comprises a dendritic cell expressing said humanized C1q protein(s).

The term "germline" in reference to an immunoglobulin nucleic acid sequence includes a nucleic acid sequence that can be passed to progeny.

The phrase "immunoglobulin molecule" includes two immunoglobulin heavy chains and two immunoglobulin light chains. The heavy chains may be identical or different, and the light chains may be identical or different.

The term "antigen-binding protein" as used herein includes antibodies and various naturally produced and engineered molecules capable of binding the antigen of interest. Such include, e.g., domain-specific antibodies, single domain antibodies (e.g., derived from camelids and fish, etc.), domain-deleted antibodies, chimeric antibodies. CDR-grafted antibodies, diabodies, triabodies, tetrabodies, minibodies, nanabodies (e.g., monovalent nanobodies, bivalent nanobodies, etc.), small modular immunopharmaceuticals (SMIPs), shark variable IgNAR domains. T cell receptor molecules and molecules comprising T cell receptor variable domains and fragments thereof, etc. Antigen-binding protein may also include antigen-binding fragments such as, e.g., (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), etc.

The term "antibody", as used herein, includes immunoglobulin molecules comprising four polypeptide chains, two heavy (H) chains and two light (L) chains inter-connected by disulfide bonds. Each heavy chain comprises a heavy chain variable domain and a heavy chain constant region ($C_H$). The heavy chain constant region comprises three domains, $C_H1$, $C_H2$ and $C_H3$. Each light chain comprises a light chain variable domain and a light chain constant region ($C_L$). The heavy chain and light chain variable domains can be further subdivided into regions of hypervariability, termed complementarity determining regions (CDR), interspersed with regions that are more conserved, termed framework regions (FR). Each heavy and light chain variable domain comprises three CDRs and four FRs, arranged from amino-terminus to carboxy-terminus in the following order: FR1, CDR1, FR2, CDR2, FR3, CDR3, FR4 (heavy chain CDRs may be abbreviated as HCDR1, HCDR2 and HCDR3; light chain CDRs may be abbreviated as LCDR1, LCDR2 and LCDR3).

As used herein, "an antibody that binds C1q" or an "anti-C1q antibody" includes antibodies and antigen-binding fragments thereof that specifically recognize a single C1q subunit (e.g., C1qa, C1qb, and/or C1qc), as well as antibodies and antigen-binding fragments thereof that specifically recognize a dimeric complex of two C1q subunits (e.g., C1qa/C1qb, and C1qc/C1qc dimers) as well as trimers of dimers. The antibodies and antigen-binding fragments can also bind soluble C1q and/or IgM or IgG bound C1q.

The term "high affinity" antibody or antigen-binding protein refers to an antibody that has a $K_D$ with respect to its target epitope about of $10^{-9}$ M or lower (e.g., about $1\times10^{-9}$M, $1\times10^{-10}$ M, $1\times10^{-11}$ M, or about $1\times10^{-12}$ M).

The phrase "bispecific antibody" or "bispecific antigen-binding protein" includes an antibody or antigen-binding protein capable of selectively binding two epitopes. Bispecific antibodies generally comprise two arms, each binding a different epitope (e.g., two heavy chains with different specificities)—either on two different molecules (e.g., different epitopes on two different immunogens) or on the same molecule (e.g., different epitopes on the same immunogen). If a bispecific antibody or antigen-binding protein is capable of selectively binding two different epitopes (a first epitope and a second epitope), the affinity of the first antibody arm for the first epitope will generally be at least one to two or three or four or more orders of magnitude lower than the affinity of the first antibody arm for the second epitope, and vice versa. Epitopes specifically bound by the bispecific antibody can be on the same or a different target (e.g., on the same or a different protein). Exemplary bispecific antibodies include those with a first antibody arm specific for C1q, and a second antibody arm specific for an antigen of interest (e.g., an antigen of an infectious agent). Bispecific antibodies can be made, for example, by combining heavy chains that recognize different epitopes of the same immunogen. For example, nucleic acid sequences encoding heavy chain variable sequences that recognize different epitopes of the same immunogen can be fused to nucleic acid sequences encoding the same or different heavy chain constant regions, and such sequences can be expressed in a cell that expresses an immunoglobulin light chain. A typical bispecific antibody has two heavy chains each having three heavy chain CDRs, followed by (N-terminal to C-terminal) a $C_H1$ domain, a hinge, a $C_H2$ domain, and a $C_H3$ domain, and an immunoglobulin light chain that either does not confer epitope-binding specificity but that can associate with each heavy chain, or that can associate with each heavy chain and that can bind one or more of the epitopes bound by the heavy chain epitope-binding regions, or that can associate with each heavy chain and enable binding of one or both of the heavy chains to one or both epitopes. Similarly, the phrase "multispecific antibody" includes an antibody capable of selectively binding multiple epitopes (e.g., two, three, four epitopes).

The phrase "complementarity determining region," or the term "CDR," includes an amino acid sequence encoded by a nucleic acid sequence of an organism's immunoglobulin genes that normally (i.e., in a wild-type animal) appears between two framework regions in a variable region of a light or a heavy chain of an immunoglobulin molecule. A CDR can be encoded by, for example, a germline sequence or a rearranged or unrearranged sequence, and, for example, by a naive or a mature B cell. A CDR can be somatically mutated (e.g., vary from a sequence encoded in an animal's germline), humanized, and/or modified with amino acid substitutions, additions, or deletions. In some circumstances (e.g., for a CDR3), CDRs can be encoded by two or more sequences (e.g., germline sequences) that are not contiguous (e.g., in an unrearranged nucleic acid sequence) but are contiguous in a B cell nucleic acid sequence, e.g., as the result of splicing or connecting the sequences (e.g., V-D-J recombination to form a heavy chain CDR3).

The phrase "functional fragment" includes fragments of antigen-binding proteins such as antibodies that can be expressed, secreted, and specifically bind to an epitope with a $K_D$ in the micromolar, nanomolar, or picomolar range. Specific recognition includes having a $K_D$ that is at least in the micromolar range, the nanomolar range, or the picomolar range.

The phrase "heavy chain," as in "immunoglobulin heavy chain", includes an immunoglobulin heavy chain sequence, including immunoglobulin heavy chain constant region sequence, from any organism. Heavy chain variable domains include three heavy chain CDRs and four FR regions, unless otherwise specified. Fragments of heavy chains include CDRs, CDRs and FRs, and combinations thereof. A typical heavy chain has, following the variable domain (from N-terminal to C-terminal), a $C_H1$ domain, a hinge, a $C_H2$ domain, and a $C_H3$ domain. A functional fragment of a heavy chain includes a fragment that is capable of specifically recognizing an epitope (e.g., recognizing the epitope with a $K_D$ in the micromolar, nanomolar, or picomolar range), that is capable of expressing and secreting from a cell, and that comprises at least one CDR. A heavy chain variable domain is encoded by a variable region gene sequence, which generally comprises $V_H$, $D_H$, and $J_H$ segments derived from a repertoire of $V_H$, $D_H$, and $J_H$ segments present in the germline. Sequences, locations and nomenclature for V, D, and J heavy chain segments for various organisms can be found on the website for the International Immunogenetics Information System (IMGT database).

The phrase "light chain", as in "immunoglobulin light chain", includes an immunoglobulin light chain sequence from any organism, and unless otherwise specified includes human kappa and lambda light chains and a VpreB, as well as surrogate light chains. Light chain variable domains typically include three light chain CDRs and four framework (FR) regions, unless otherwise specified. Generally, a full-length light chain includes, from amino terminus to carboxyl terminus, a variable domain that includes FR1-CDR1-FR2-CDR2-FR3-CDR3-FR4, and a light chain constant region. A light chain variable domain is encoded by a light chain variable region gene sequence, which generally comprises $V_L$ and $J_L$ segments, derived from a repertoire of V and J segments present in the germline. Sequences, locations and nomenclature for V and J light chain segments for various organisms can be found on the website for the International Immunogenetics Information System (IMGT database). Light chains include those, e.g., that do not selectively bind any epitopes recognized by antigen-binding protein (e.g., antibody) in which they appear. Light chains also include those that bind and recognize, or assist the heavy chain with binding and recognizing, one or more epitopes selectively bound by the antigen-binding protein (e.g., an antibody) in which they appear.

In various embodiments, the antigen-binding protein binds both C1q and an antigen of interest.

In another embodiment, the rodent model is used to determine if a candidate bispecific antigen-binding protein is capable of blocking or affecting an antigen of interest which is an infectious disease associated antigen. In one embodiment, the rodent is infected with an infectious agent. In one embodiment, the infectious disease associated antigen is a viral antigen.

In another embodiment, wherein the antigen of interest is an infectious disease associated antigen, the antigen of interest is a bacterial antigen. In some aspects, the bacterial antigen is a *Staphylococcus* antigen.

In some aspects, the C1q-based bispecific antigen binding protein is a human C1q based antigen binding protein. In one embodiment, the antigen binding protein is an antibody, e.g., a human antibody, or an antigen-binding fragment thereof.

In some embodiments, the testing of a bispecific antibody with one arm targeting human C1q and another arm targeting an infectious disease associated antigen (such as *S. aureus*), is done in vivo using a genetically engineered animal disclosed herein that expresses a humanized C1q having a human or substantially human globular head domain in each of its C1qa, C1qb and C1qc polypeptide chains. The animal can be infected with the infectious disease associated antigen (such as *S. aureus*), and the bispecific antibody can be evaluated in such animal, e.g., in its ability to reduce bacterial burden and/or improve survival.

G. Use of Genetically Modified Non-Human Animals

Further disclosed are various methods of using the genetically modified non-human animals described herein.

In one embodiment, provided herein is a method of screening therapeutic drug candidates that target an antigen of interest comprising (a) providing or receiving a genetically modified rodent (such as a mouse or rat) comprising at its endogenous rodent C1q locus a nucleic acid sequence encoding a chimeric, humanized C1qa polypeptide, C1qb polypeptide and/or C1qc polypeptide and/or any combination thereof, (b) introducing into said genetically modified rodent an antigen of interest, (c) contacting said rodent with a drug candidate of interest, wherein the drug candidate is directed against the human C1q and the antigen of interest, and (d) assaying if the drug candidate is efficacious in preventing, reducing or eliminating cells or viruses characterized by the presence or expression of the antigen of interest. In various embodiments, the rodent expresses a functional humanized C1q complex. In one embodiment of the method, the genetically modified rodent comprises at the endogenous rodent C1q locus a nucleic acid sequence encoding a chimeric C1qa polypeptide comprising a globular head domain that is substantially human, a chimeric C1qb polypeptide comprising a globular head domain that is substantially human, and a chimeric C1qc polypeptide comprising a globular head domain that is substantially human. In one embodiment of the method described herein, the rodent does not comprise a nucleic acid sequence encoding a functional globular head domain of the corresponding rodent protein.

In various embodiments of the method described herein, introduction of the antigen of interest into the genetically modified rodent described herein may be accomplished by any methods known to those skilled in the art, which may include, without limitation, transgenesis, injection, infection, tissue or cell transplantation. As such, introduction may be achieved by expressing in the rodent the antigen of interest, which can comprise genetically modifying said rodent to express the antigen of interest. Alternatively, introduction may comprise introduction into said rodent a cell expressing the antigen of interest, e.g., as in cell or tissue transplantation. Introduction may also comprise infecting said rodent with the antigen of interest, e.g., as in bacterial or viral infection. In one embodiment, the antigen of interest may be a human antigen of interest. In another embodiment, it may be a bacterial or a viral antigen of interest. The antigen of interest may be a tumor-associated antigen or an infectious disease associated antigen, e.g., a bacterial or a viral antigen, as described in detail above.

In another embodiment, provided herein is a method of assessing or screening therapeutic drug candidates that target an antigen of interest comprising mixing a cell or virus expressing the antigen of interest with (i) a drug candidate of interest, wherein the drug candidate is directed against the human C1q and the antigen of interest, and (ii) a blood sample (e.g., a whole blood sample) of a genetically modified rodent described herein, and (b) assaying to determine whether the drug candidate is efficacious in reducing or eliminating the cell or virus characterized by the presence or expression of the antigen of interest. The determination can be made based on measuring, e.g., percentage survival of the cell or virus where a drug candidate is used as compared to a control drug or no drug at all. The antigen of interest may be a tumor-associated antigen or an infectious disease associated antigen, e.g., a bacterial or a viral antigen, as described in detail above. In some embodiments, the antigen of interest is a bacterial antigen such as a *Staphylococcus* antigen. In some embodiments, the cell is a bacterial cell such as a *Staphylococcus* cell.

In various embodiments of the methods of screening a therapeutic drug candidate, the drug candidate may be an antigen-binding protein, e.g., an antibody, e.g., a bispecific antibody. In various aspects, such drug candidate is capable of binding both human C1q and the antigen of interest. The antigen of interest may be a human antigen. The antigen of interest may also be a primate, e.g., a monkey, antigen. Thus, the drug candidate used for screening may be capable of binding both a human antigen and a corresponding primate antigen, in addition to binding human C1q. The drug candidate may also be capable of binding primate, e.g., monkey, C1q. Thus, the drug candidate may be capable of binding both human and primate, e.g., monkey, C1q; and also, in one embodiment, be capable of binding a human antigen of interest. In another embodiment, the antigen of interest may be a bacterial or a viral antigen, and the drug candidate may be capable of binding both the human and primate, e.g., monkey, C1q and the antigen of interest (e.g., a viral or bacterial antigen).

In various embodiments of the methods described herein, the therapeutic candidate is capable of reducing, eliminating, or preventing a disease. In one embodiment, the disease is a tumor, and the therapeutic candidate is capable of reducing, eliminating, or preventing tumor growth as compared to an agent that does not target the antigen of interest. In such an embodiment of the method, determination whether the drug candidate is efficacious in preventing, reducing or eliminating cells characterized by the presence or expression of the antigen of interest can be performed using a tumor volume assay, a tumor cell killing assay, induction of apoptotic markers in tumors, reduction in blood vessel growth in tumors, infiltration of immune cells into tumors, etc. In another embodiment, the disease is an infectious disease, and a therapeutic candidate is capable reducing, eliminating, or preventing a bacterial or a viral infection as compared to an agent that does not target the antigen of interest. In such an embodiment of the method, determination whether the drug candidate is efficacious in preventing, reducing or eliminating cells or viruses characterized by the presence or expression of the antigen of interest can be performed using a measure of bacterial or viral titers, induction of apoptotic markers in infected cells, etc., or by measuring survival of bacterial cells or viruses using a blood sample (e.g., a whole blood sample).

In addition to evaluating bispecific antibodies with one arm targeting a humanized C1q protein and the other arm targeting an antigen of interest, the genetically engineered non-human animals expressing a humanized C1q protein disclosed herein are useful for evaluating the effects of other antibodies, e.g., monospecific antibodies having a human Fc region (such as a human antibody). The binding of a humanized C1q to the human Fc region of an antibody can activate classical complement pathway, which leads to complement-dependent cytotoxicity (CDC). There had been a difficulty in assessing whether an antibody has an effect on the complement system of a recipient, or whether or how much of the efficacy of a therapeutic antibody is attributable to the action of the complement system. The genetically engineered non-human animals expressing a humanized C1q disclosed herein will permit assessment of whether an antibody having a human Fc region (e.g., a human antibody) will be capable of activating classical complement pathway, and the results of such assessment will more accurately reflect whether such antibody will activate classical complement pathway when given to human patients.

Therefore, in a further aspect, disclosed herein is a method of assessing whether an antibody comprising a human Fc region can activate classical complement pathway by utilizing a genetically engineered non-human animal (e.g., a rodent such as a mouse or rat) expressing a humanized C1q protein disclosed herein.

In some embodiments, the method utilizes a cell expressing an antigen of interest on the cell surface, a candidate antibody comprising a human Fc region and directed to the antigen of interest, and a serum sample from a genetically engineered non-human animal expressing a humanized C1q protein, and is designed to evaluate in vitro complement-dependent cytotoxicity of the cell expressing the antigen of interest. In specific embodiments, the cell is first mixed with the candidate antibody to allow the antibody to bind to the antigen of interest expressed on the cell surface; then a serum sample is added to the cell-antibody mixture to permit binding of the C1q proteins in the serum sample to antibodies bound to the antigen of interest on the cell. Cytotoxicity (i.e., killing of said cell) can then be measured using reagents readily available, including those from commercial sources (e.g., CytoTox-Glo™ reagent from Promega), using flow cytometry methods or release of pre-loaded radioisotopes from target cells. Cytotoxicity using a serum sample from a humanized non-human animal expressing a humanized C1q protein can be compared with a serum sample from a control non-human animal without the humanization (negative control), and with a human serum sample (positive control).

In some embodiments, cells suitable for use in this method include Raji cells, Ramos cells, Daudi cells, HEK293 cells, and A431 cells. In some embodiments, Raji cells, Ramos cells, or Daudi cells are used in the present methods. The cells can naturally express an antigen of interest on the cell surface, or can be modified to recombinantly express an antigen of interest on the cell surface.

In some embodiments, the candidate antibody is a human antibody directed to a tumor antigen, a bacterial or viral antigen, etc. Examples of candidate antibodies include, e.g., anti-CD20, etc.

In some embodiments, the methods of assessing whether an antibody comprising a human Fc region can activate classical complement pathway is performed in vivo by comparing the effects of a candidate antibody in a C1q humanized animal with a C1q knockout animal. To rule out that the effect is due to ADCC (as opposed to CDC), NK cells, neutrophils and macrophages in the animals could be depleted, leaving the complement system intact.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1. Generation of Humanized C1q Mouse

Mouse genomic sequence of C1q genes can be found under NCBI Accession Number NC_000070.6, and C1q loci are located at mouse chromosome 4D3 (Reference GRCm38.p4 C57BL/6J). Human genomic sequence of C1q genes can be found under NCBI Accession Numbers NG_007281.1, NG_007283.1 and NG_007565.1, and C1q loci are located at human chromosome 1p36.1. Some examples of genomic and amino acid sequences for human and mouse C1q are listed below in Tables 1 and 2. Predicted signal peptide in the listed SEQ ID NOs boundaries are indicated. The signal peptide boundaries are also boxed in FIGS. 3A-3C.

TABLE 1

GeneBank Accession Numbers for Mouse C1q sequences

| Protein/<br>Gene Name | Genomic Sequence<br>NCBI Accession<br>Number | Protein NCBI<br>Accession<br>Number | Sequence<br>ID No.<br>(Immature<br>Protein) | Signal<br>peptide<br>(amino<br>acids) |
| --- | --- | --- | --- | --- |
| Mouse C1qa | NC_000070.6 | NP_031598.2 | 1 | 1-22 |
| Mouse C1qb | NC_000070.6 | NP_033907.1 | 2 | 1-25 |
| Mouse C1qc | NC_000070.6 | NP_031600.2 | 3 | 1-29 |

TABLE 2

GeneBank Accession Numbers for Human C1q Sequences

| Protein/Gene<br>Name | Genomic<br>Sequence<br>NCBI<br>Accession<br>Number | Protein NCBI<br>Accession<br>Number | Sequence<br>ID No.<br>(Immature<br>Protein) | Signal<br>peptide |
| --- | --- | --- | --- | --- |
| Human C1QA | NG_007282.1 | NP_001334394.1 | 4 | 1-22 |
| Human C1QB | NG_007283.1 | NP_000482.3 | 5 | 1-27 |
| Human C1QC | NG_007565.1 | NP_001334548.1 | 6 | 1-28 |

Briefly, to generate chimeric C1q mice, the mouse C1q locus was humanized by construction of a unique targeting vector from human and mouse bacterial artificial chromosomes (BAC) DNA using VELOCIGENE® technology (see, e.g., U.S. Pat. No. 6,586,251 and Valenzuela et al. (2003) High-throughput engineering of the mouse genome couple with high-resolution expression analysis. *Nat. Biotech.* 21(6): 652-659, both incorporated herein by reference) using the mouse BAC library Mouse BAC ES release 2 (Incyte Genomics, 129/SvJ in pBeloBAC11). DNA from mouse BAC clone 302p21 was modified to replace genomic DNA encoding portions of mouse C1qa, C1qb, and C1qc (mouse C1q genes are located in close proximity to one another on the reverse strand of mouse chromosome 4) with corresponding portions of human C1qa, C1qb, and C1qc, respectively (human C1q genes are located in close proximity to one another on the forward strand of human chromosome 1).

The mouse C1q BAC was modified by introduction of human C1q sequences, to generate a BAC comprising humanized C1qa, C1qb, and C1qc genes. The sequences encoding substantially the mouse C1qa, C1qb, and C1qc globular domains were replaced, respectively, with the corresponding sequences encoding substantially the human C1qa, C1qb, and C1qc globular domains. Alignments of human and mouse C1q (and rat) protein sequences are depicted in FIGS. 3A, B, and C, where the boundaries for globular heads are as indicated, and the boundaries of mouse/human genes are indicated with arrows. The amino acid sequences of the humanized mouse C1qa C1qb, and C1qc proteins are set forth in SEQ ID NOs: 10, 11, and 12, respectively, and are listed in Table 3 below, with mouse sequences italicized.

TABLE 3

Amino Acid Sequences of the Chimeric Mouse/Human C1q proteins

| Protein | Sequence | SEQ ID<br>NO: |
| --- | --- | --- |
| C1qa | *METSQGWLVACVLTMTLVWTVAEDVCRAPNGKDGAPGNPG*<br>*RPGRPGLKGERGEPGAAGIRTGIRGFKGDPGESGPPGKPGN*<br>*VGLPGPTGPLGDSGPQGLKGVKGNPGNIRD* QPRPAFSAIRRN<br>PPMGGNVVIFDTVITNQEEPYQNHSGRFVCTVPGYYFTFQV<br>LSQWEICLSIVSSSRGQVRRSLGFCDTTNKGLFQVVSGGMVL<br>QLQQGDQVWVEKDPKKGHIYQGSEADSVFSGFLIFPSA* | 10 |
| C1qb | *MKTQWGEVWTHLLLLLLGFLHVSWAQSSCTGPPGIPGIPGV*<br>*PGVPGSDGQPGTPGIKGEKGLPGLAGDLGEFGEKGDPGIPG*<br>*TPGKVGPKGPVGPKGTPGPSGPRGPKGDSGDYGAT*<br>QKIAFSATRTINVPLRRDQTIRFDHVITNMNNNYEPRSGKFTCKVP<br>GLYYFTYHASSRGNLCVNLMRGRERAQKVVTFCDYAYNTFQVTT<br>GGMVLKLEQGENVFLQATDKNSLLGMEGANSIFSGFLLFPDMEA* | 11 |
| C1qc | *MVVGPSCQPPCGLCLLLLFLLALPLRSQASAGCYGIPGMPGMP*<br>*GAPGKDGHDGLQGPKGEPGIPAVPGTRGPKGQKGEPGMPG*<br>*HRGKNGPRGTSGLPGDPGPRGPPGEPGVEGR* YKQKFQS<br>VFTVTRQTHQPPAPNSLIRFNAVLTNPQGDYDTSTGKFTCKV<br>PGLYYFVYHASHTANLCVLLYRSGVKVVTFCGHTSKTNQVNSGG<br>VLLRLQVGEEVWLAVNDYYDMVGIQGDSVFSGFLLFPD* | 12 |

Example 1.1. Generation of C1q Knock Out Mouse

Figure 1B:
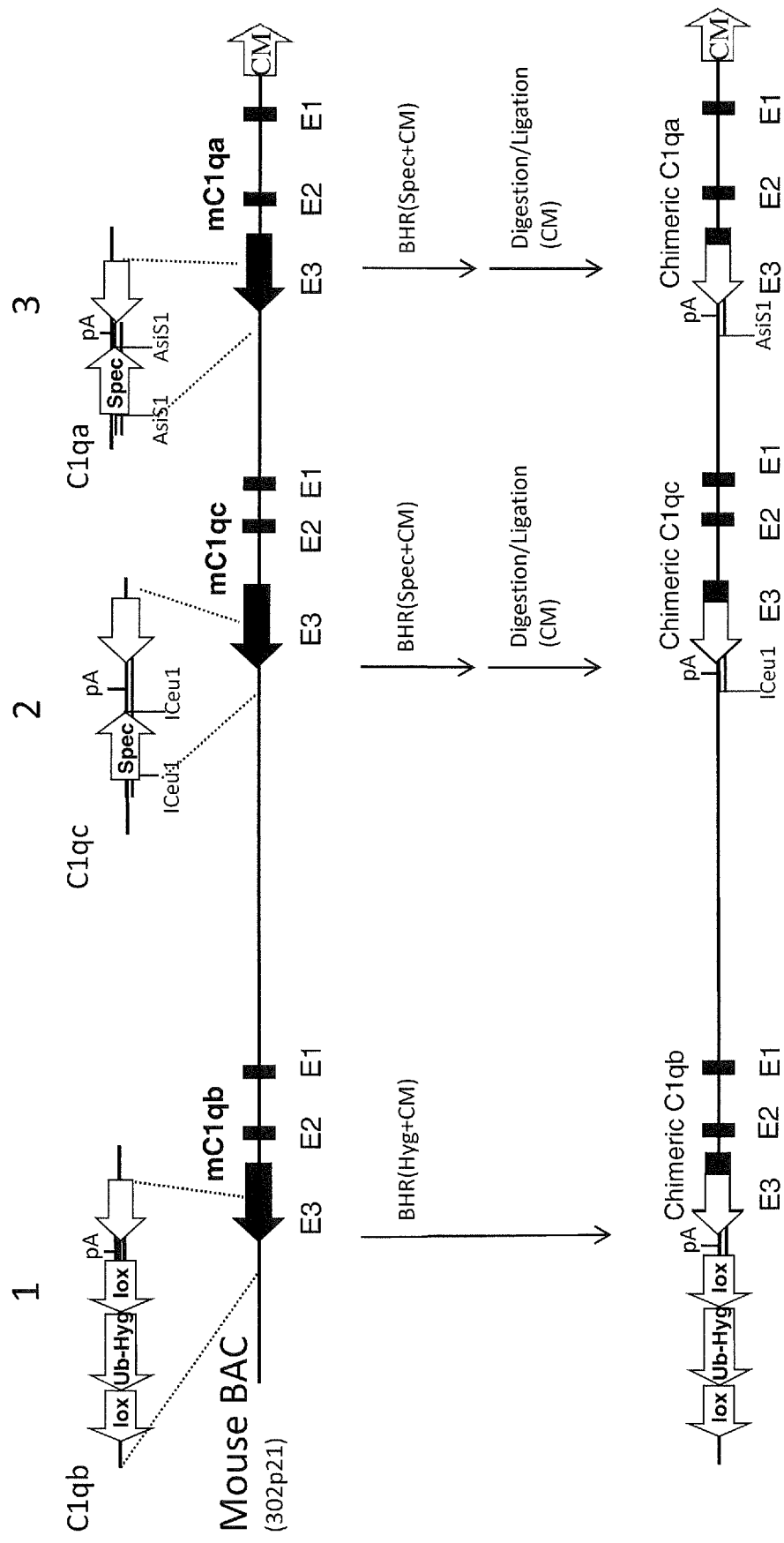
FIG. 1B shows a schematic representation (not to scale) of the creation of a humanized mouse C1q targeting vector, with chimeric human/mouse genes inserted by digestion/ligation and/or bacterial homologous recombination (BHR) into the mouse BAC genes (mouse genes are indicated with "m" before the gene label). Exons of the three C1q genes are labeled below the diagram (e.g., E1, E2, and E3). Several restriction enzyme locations are indicated. CM=chloramphenicol; lox=loxP site; Ub-Hyg=hygromycin selection cassette; p=polyA tail; Spec=spectinomycin.

In detail, first, a mouse C1q locus comprising all three C1q genes was modified to delete the 17.6 kB nucleotide sequence comprising genes encoding mouse C1q (see FIG. 1A). A targeting vector comprising LacZ-neo cassette, 20 Kb 5' homology arm and 55 kb 3' homology arm was introduced into mouse BAC 302p21 by bacterial homologous recombination such that 17.6 Kb of nucleotide sequence comprising all three mouse C1q genes from C1qa ATG to C1qb stop codon was deleted. The deletion spanned C1qa exon 2 just after the start ATG through C1qb exon 3 past the stop codon including 19 bp into the C1qb 3' UTR. The cassette was inserted such that the LacZ coding sequence was in frame with the C1qa ATG codon. LacZ coding sequence is followed by an SV40 polyadenylation site, then a floxed neomycin resistance cassette under control of the mouse phosphoglycerate kinase 1 (Pgk1) promoter with Pgk1 polyadenylation signal. The resultant vector was used to electroporate mouse ES cells to create modified ES cells for generating a mouse that lacked the endogenous C1q locus. The sequences of the various junctions in the deleted locus are labeled in the second schematic diagram in FIG. 1C, with corresponding nucleic acid sequences listed in Table 4 below. The junctions shown in Tables in this example only list short nucleotide sequences, but direct one skilled in the art to the location where the sequences were inserted into the mouse genome.

TABLE 4

Junction Sequences of the mouse C1q Knock Out Locus

| Junction Description | Sequence | SEQ ID NO |
|---|---|---|
| Mouse C1qa/KpnI/lacZ | CATACCCAGTGTCCCTGTGTGTCTCTGTAGGGACA CCATG/GGTACC/GATTTAAATGATCCAGTGGTC | 13 |
| Pgk1 polyA/loxP/XhoI/ Mouse C1qb | GCAGCCCCTAG/ATAACTTCGTATAATGTATGCT ATACGAAGTTAT/CCTAGG/CTATCCAACACCATCT TCCTGC | 14 |

ES cells containing deletion of mouse C1q sequences were identified by a quantitative TAQMAN™ assay (see, e.g., Lie and Petropoulos, 1998. Curr. Opin. Biotechnology 9:43-48, incorporated herein by reference), modification of allele assay (MOA). Specific primer sets and probes were designed for detecting insertion of the cassette sequences (gain-of-allele, GOA) and deletion of mouse sequences (loss-of-allele, LOA). Table 5 identifies the names and locations of each of primers/probe sets used in the quantitative PCR assays.

TABLE 5

Primer and Probes Used in a MOA Assay to Confirm Deletion of mouse C1q locus

| Description | Sequence | Loss of Allele (LOA) or Gain of Allele (GOA) | SEQ ID NO |
|---|---|---|---|
| 598TU Probe | TCCCGCACCATCCTGGAGGCAAT | LOA (mouse C1qa) | 15 |
| F | TAAGCGTTCTCTCCGGCTGG | | 16 |
| R | CCTCTTCTCAGGACCCCTAAAC | | 17 |
| | | | |
| LacZ probe | CGATACTGTCGTCGTCCCCTCAAACTG | GOA | 18 |
| F | GGAGTGCGATCTTCCTGAGG | | 19 |
| R | CGCATCGTAACCGTGCATC | | 20 |
| | | | |
| Neo probe | TGGGCACAACAGACAATCGGCTG | GOA | 21 |
| F | GGTGGAGAGGCTATTCGGC | | 22 |
| R | GAACACGGCGGCATCAG | | 23 |
| | | | |
| 587tnTD Probe | AGGACCATCAACAGCCCCTTCrCGAC | LOA (mouse C1qb) | 24 |
| F | GAAAGTCGCCTTCTCTGCCC | | 25 |
| R | CGAAGCGAATGACCTGGTTc | | 26 |

Targeted ES cells described above were used as donor ES cells and introduced into an 8-cell stage mouse embryo by the VELOCIMOUSE® method (see, e.g., U.S. Pat. No. 7,294,754 and Poueymirou et al. (2007) F0 generation mice that are essentially fully derived from the donor gene-targeted ES cells allowing immediate phenotypic analyses Nature Biotech. 25(1):91-99). VELOCIMICE® (F0 mice fully derived from the donor ES cell) independently bearing a mouse C1q deletion were identified by genotyping using a modification of allele assay (see above) that detects the absence of mouse C1q gene sequences. Modified mouse ES cells comprising the deleted mouse C1q locus (mouse C1q KO HET ES cells) were used for humanized C1q construction as described below.

The selection cassette used in this method may be removed by methods known by the skilled artisan. For example, ES cells bearing the C1q knock out locus may be transfected with a construct that expresses Cre in order to remove the foxed cassette. The selection cassette may optionally be removed by breeding to mice that express Cre recombinase. Optionally, the selection cassette is retained in the mice.

Example 1.2. Generation of Humanized C1q Mouse

To generate humanized mouse C1q, donor plasmids were generated by In-Fusion HD Cloning Kits™ (Clontech) using sequences for C1q globular head domains (the same sequences as used for the humanized C1q rat in the Example below) and overlapping mouse sequences. For C1qb humanization construct, a loxP-Ub-Hyg selection cassette was inserted by restriction digest downstream of the human C1qb polyA sequence. For both C1qa and C1qc constructs, a spectinomycin (Spec) selection cassette was inserted by restriction digest downstream of each C1qa and C1qc polyA sequences. The resultant constructs were introduced sequentially into the mouse C1q BAC (302p21) through bacterial homologous recombination followed by selection and/or digestion steps to remove the selection cassettes, as demonstrated in FIG. 1B. In this particular embodiment, the chimeric nucleic acid sequence for C1qb was introduced first (1 in the figure), followed by introduction of chimeric C1qc DNA (2 in the figure), and then chimeric C1qa DNA (3 in the figure).

The large targeting vector containing all three chimeric C1q genes was electroporated into mouse C1q KO HET ES cells as depicted in FIG. 1C, and successful integration was confirmed by a TAQMAN® real-time PCT-based modification of allele (MOA) assay described above. Primers and probes used for the MOA assay, and their locations, are described in Table 6.

TABLE 6

Primer and Probes Used in MOA Assay to Confirm Presence of Chimeric Mouse/Human C1q genes

| Description | Sequence | Loss of Allele (LOA) or Gain of Allele (GOA) | SEQ ID NO |
|---|---|---|---|
| 1565ma1 | TGACAAGGTCCTCACCAACCAGGAGAG | LOA (mouse | 27 |
| F | CGCTTGGCAACGTGGTTAT | C1qa) | 28 |
| R | CCCGTGTGGTTCTGGTATGG | | 29 |
| | | | |
| 1565mb1 | TATGAGCCACGCAACGGCAAGTTCA | LOA (mouse | 30 |
| F | TCACCAACGCGAACGAGAA | C1qb) | 31 |
| R | GGCCAGGCACCTTGCA | | 32 |
| | | | |
| 1565mc5 | CCCATCCTCACTCAGACCTCTTCCTCCA | LOA (mouse | 33 |
| F | CACCTCGCTCCCTCTGCTT | C1qc) | 34 |
| R | CAGGAACCAGGGTGGACTTC | | 35 |
| | | | |
| 1565ha1 | CAACGTGGTCATCTTCGACACGGTCA | GOA (human | 36 |
| F | CGGAACCCCCCAATGG | C1qa) | 37 |
| R | TGGTTCTGGTACGGTTCTTCCT | | 38 |
| | | | |
| 1565bh2 | ACCATCAACGTCCCCCTGCGC | GOA (human | 39 |
| F | AATCGCCTTCTCTGCCACAA | C1qb) | 40 |
| R | GTGGTCGAAGCGGATGGT | | 41 |
| | | | |
| 1565hc4 | CACCTGCAAAGTCCCCGGCCTC | GOA (human | 42 |
| F | TGACACGAGCACTGGCAAGT | C1qc) | 43 |
| R | CGACGCGTGGTAGACAAAGTAG | | 44 |
| | | | |
| Hyg | ACGAGCGGGTTCGGCCCATTC | LOA | 45 |
| F | TGCGGCCGATCTTAGCC | (hygromycin | 46 |
| R | TTGACCGATTCCTTGCGG | resistance deletion after introduction of Cre) | 47 |

Junction sequences between various genetically engineered components at the chimeric locus are depicted in Table 7 below, and are indicated on the bottom schematic diagram in FIG. 1C. The junctions shown in Tables in this Example only list short nucleotide sequences, but direct one skilled in the art to the location where the sequences were inserted into the mouse genome.

located at Rat chromosome 5 (Reference Rnor_6.0 Primary Assembly). Human genomic sequence of C1q genes can be found under NCBI Accession Numbers NG_007283.1, NG_007282.1 and NG_007565.1, and C1q loci are located at human chromosome 1p36.1. Some examples of genomic and amino acid sequences for rat and human C1q are listed in Tables 8 and 2, respectively. Predicted signal peptide boundaries in the listed SEQ ID NOs are indicated. The signal peptide boundaries are also boxed in FIGS. 3A-3C.

TABLE 7

Junction Sequences of the Chimeric Human/Mouse C1q Locus

| Junction Description | Sequence | SEQ ID NO |
|---|---|---|
| Mouse C1qa exon 3/human C1QA (globular domain) | CGGCCCCCAAGGACTGAAGGGCGTGAAAGGCAATCCA GGCAATATCAGGGAC/CAGCCGAGGCCAGCCTTCTCCG CCATTCGGCGGAACCCCCCAATGGGGGGC | 48 |
| Human C1QA 3' UTR/AsiSI site/3' of mouse C1qa (non-coding) | TTGAGAGGGAGGCCTAAGAATAATAACAATCCAGTG CTTAAGAGTCAGGC/GCGATCGC/TGATGCACGCCTTT AATCCCAGCACTTGGGAGGCAGAGACAGGTGA | 49 |
| Mouse C1qc exon 3/human C1QC (globular domain) | GCCAGGGGACCCAGGCCCCAGGGGGCCTCCGGGGG AGCCAGGTGTGGAGGGCCGA/TACAAGCAGAAATTC CAGTCAGTGTTCACGGTCACTCGGCAGACCCACCA | 50 |
| Human C1QC 3' UTR/3' of mouse C1qc (non-coding) | TGAATTTCGGATCTTCAACTTTGCATCAGCCATAGCT GGGCTCTGGACTC/TACCTAACTATAACGGTCCTAAGGT AGCGAAAGGGGGATGATTTGGAGT | 51 |
| Mouse C1qb exon 3/ human C1QB (globular domain) | TCCAGGCCCCTCTGGACCCCGCGGTCCCAAAGGCGATT CTGGGGACTACGGGGCTACA/CAGAAAATCGCCTTCTC TGCCACAAGAACCATCAACGTCCCCCTGCGCCGGG | 52 |
| Human CIQB 3'UTR/loxp-Ub-Hyg region | GCACCTGGCACACCAGAAGTGCCATGCTCAGAAATG TTGGTTACATGAATGAAT/GCGGCCGCACCGGTATAA CTTCGTATAATGTATGCTATACGAAGTTA | 53 |
| loxp-Ub-Hyg region/3' of mouse C1qb (non-coding) | CCGGCGCGCCATAACTTCGTATAATGTATGCTATACG AAGTTATGTCGAC/GAATGTTCATAGGCTGGGGAGATG GCTCAGTCAGTAAAGTACTTAGCTTGC | 54 |

Targeted ES cells described above are used as donor ES cells and introduced into an 8-cell stage mouse embryo by the VELOCIMOUSE® method described above. VELOCIMICE® independently bearing a humanized C1q genes are identified by genotyping using a modification of allele assay (see above) that detects the presence of the unique human C1q gene sequences. Mice comprising a heterozygous modification of the C1q genes are bred to homozygousity.

To generate ES cells without the hygromycin resistance cassette, a plasmid containing cre recombinase coding sequence was electroporated into mouse C1q KO HET ES cells and resulting ES cell clones were screened for loss of the hygromycin resistance cassette by TaqMan assay using primers and probe depicted in Table 6. Selected clones were then microinjected into 8-cell stage mouse embryos as described above and resulting mice were bred to homozygosity. The resulting expressed chimeric proteins are shown above in Table 3 and the Sequence Listing.

Example 2. Generation of Humanized C1q Rat

Rat genomic sequence of C1q genes can be found under NCBI Accession Number NC_005104.4, and C1q loci are

TABLE 8

GeneBank Accession Numbers for Rat C1q sequences

| Protein/ Gene Name | Genomic Sequence NCBI Accession Number | Protein NCBI Accession Number | Sequence ID No. (Immature protein) | Signal peptide |
|---|---|---|---|---|
| rat C1qa | NC_005104.4 | NP_001008515.1 | 7 | 1-22 |
| rat C1qb | NC_005104.4 | NP_062135.1 | 8 | 1-25 |
| rat C1qc | NC_005104.4 | NP_001008524.1 | 9 | 1-31 |

To generate chimeric C1q rat, briefly, the rat C1q locus was humanized by construction of a unique targeting vector from synthesized human sequences and rat bacterial artificial chromosomes (BACs) DNA using the rat BAC library generated for Regeneron by LUCIGEN® from rat Dark Agouti ES cells, and the rat targeting technology described in US 2014/0310828, incorporated herein in its entirety by reference. The BAC sequences were confirmed and updated based on the data from Next Generation Sequencing. DNA from rat BAC (rat C1q BAC, LUCIGEN®) was modified to replace genomic DNA encoding portions of rat C1qa, C1qb, and C1qc (rat C1q genes are located in close proximity to one another on the reverse strand of rat chromosome 5) with corresponding portions of human C1qa, C1qb, and C1qc, respectively (human C1q genes are located in close proximity to one another on the forward strand of human chromosome 1).

The rat C1q BAC generated in-house and described above was modified by introduction of human C1q sequences, to generate a vector comprising humanized C1qa, C1qb, and C1qc genes. The sequences encoding the majority of rat C1qa, C1qb, and C1qc globular domains were replaced, respectively, with the corresponding sequences of human C1qa, C1qb, and C1qc. Alignments of human and rat C1q (and mouse) protein sequences are depicted in FIGS. 3A, B, and C, where the boundaries for globular heads are as indicated, and the boundaries of rat/human genes are indicated with arrows. The amino acid sequences of the humanized rat C1qa, C1qb, and C1qc proteins are set forth in SEQ ID NOs: 55, 56, and 57, respectively, and are listed in Table 9, with rat sequences italicized.

TABLE 9

Amino Acid Sequences of the Chimeric Rat/Human C1q proteins

| Protein | Sequence | SEQ ID NO: |
|---|---|---|
| C1qa | *METSQGWLVACVLAVTLVWTVAEDVCRAPNGKDGVAGIPG RPGRPGLKGERGEPGAAGIRTGIRGLKGDMGESGPPGKPGN VGFPGPTGPLGNSGPQGLKGVKGNPGNIRD* QPRPAFSAIRRN PPMGGNVVIFDTVITNQEEPYQNHSGRFVCTVPGYYYFTFQV LSQWEICLSIVSSSRGQVRRSLGFCDTTNKGLFQVVSGGMVL QLQQGDQVWVEKDPKKGHIYQGSEADSVFSGFLIFPSA\* | 55 |
| C1qb | *MKTQWSEILTPLLLLLLGLLHVSWAQSSCTGSPGIPGVPGIPG VPGSDGKPGTPGIKGEKGLPGLAGDHGELGEKGDAGIPGIPG KVGPKGPVGPKGAPGPPGPRGPKGDSGDYKAT* QKIAFSATRT INVPLRRDQTIRFDHVITNMNNNYEPRSGKFTCKVPGLYYFTY HASSRGNLCVNLMRGRERAQKVVTFCDYAYNTFQVTTGGM VLKLEQGENVFLQATDKNSLLGMEGANSIFSGFLLFPDMEA\* | 56 |
| C1qc | *MLRMVVGTSCQPQHGLYLLLLLLALPLRSQANAGCYGIPGMP GLPGTPGKDGHDGLQGPKGEPGIRAIPGTQGPKGQKGEPGM PGHRGKNGPMGTSGSPGDPGPRGPPGEPGEEGR* YKQKFQS VFTVTRQTHQPPAPNSLIRFNAVLTNPQGDYDTSTGKFTCKV PGLYYFVYHASHTANLCVLLYRSGVKVVTFCGHTSKTNQVNS GGVLLRLQVGEEVWLAVNDYYDMVGIQGSDSVFSGFLLFPD\* | 57 |

Example 2.1 Generation of C1q Knock Out Rat

Figure 2A:
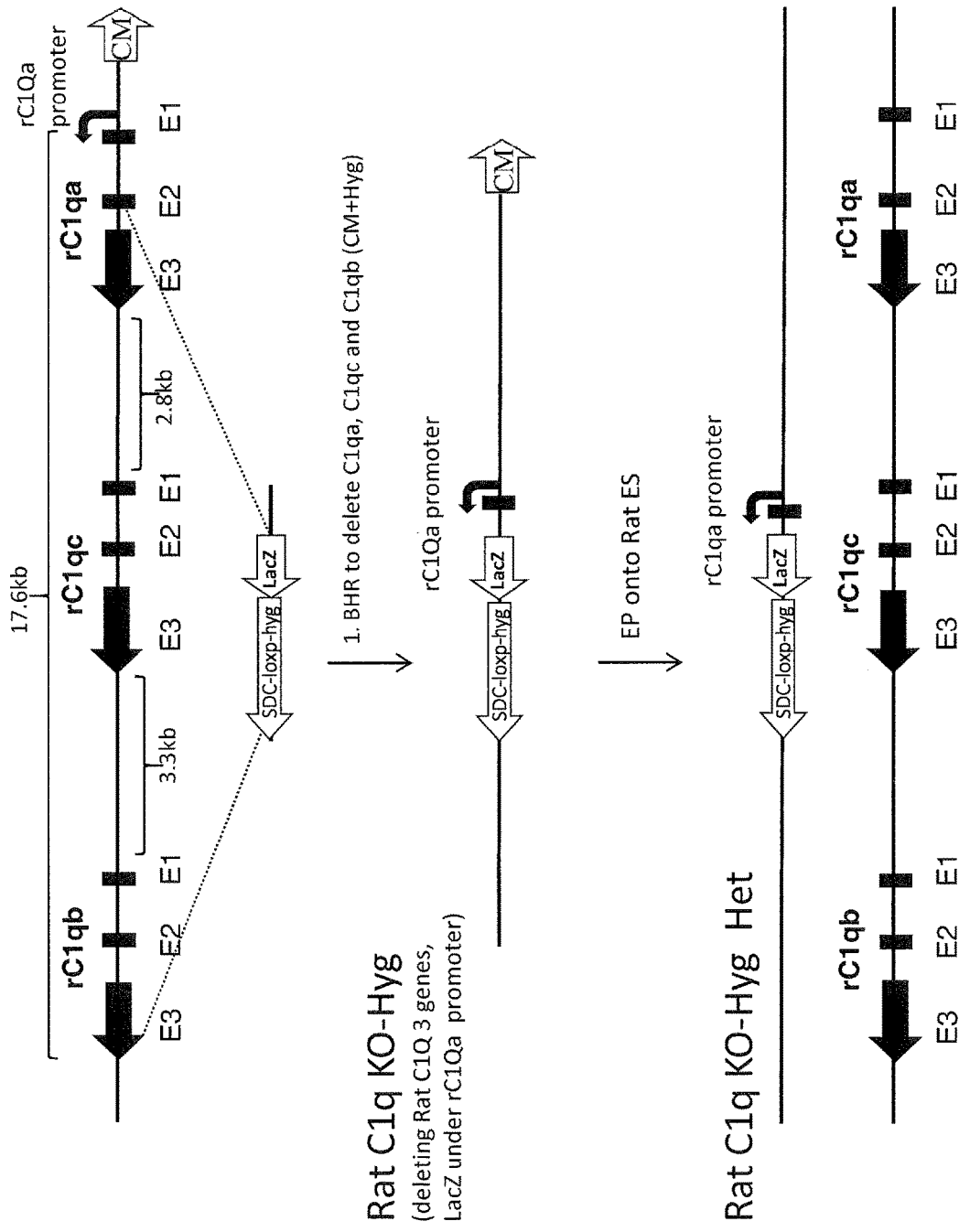
FIG. 2A shows a schematic representation (not to scale) of the exemplary method of deleting of the rat C1q locus comprising all three rat C1q genes (rat genes are indicated with "r" before the gene label). Exons of the three C1q genes are labeled below the diagram (e.g., E1, E2, and E3). Rat C1q BAC stands for rat bacterial artificial chromosome; BHR stands for bacterial homologous recombination; EP stands for electroporation. HET=heterozygous; CM=chloramphenicol; loxP=loxP site; SDC-loxP-Hyg=self-deleting LoxP-Hygromycin selection cassette.

In detail, first, a rat C1q locus comprising all three C1q genes was modified to delete a 17.6 Kb nucleotide sequence comprising genes encoding rat C1q (see FIG. 2A). A targeting vector was synthesized to comprise a LacZ gene and a self-deleting hygromycin selection cassette, and the vector contained 5' and 3' homology arms allowing deletion of all three rat C1q genes from C1qa ATG to C1qb stop codon. The vector comprising the C1q sequence deletion was introduced into rat C1q BAC via bacterial homologous recombination (BHR), and the resultant BAC DNA was used to electroporate rat ES cells to create modified ES cells for generating a rat that lacked the endogenous C1q locus. The sequences of the various junctions in the deleted locus are labeled in the second schematic diagram in FIG. 2C, with corresponding nucleic acid sequences listed in Table 10 below. The junctions shown in Tables in this example only list short nucleotide sequences, but direct one skilled in the art to the location where the sequences were inserted into the rat genome.

TABLE 10

Junction Sequences of the deletion of Rat C1q Locus

| Junction Description | Sequence | SEQ ID NO |
|---|---|---|
| Rat C1qa promoter/LacZ sequence | GATTCTCCCAATCTCTCCTCTGCAGGACCACTGGATCATT TAAATCGGTACC/CATGATGTTCCTGCAGAGACACACA GGGACCCCGGGCATGCTGGACAGTCA | 58 |

TABLE 10-continued

Junction Sequences of the deletion of Rat C1q Locus

| Junction Description | Sequence | SEQ ID NO |
|---|---|---|
| LacZ sequence/SDC-loxP-Hyg cassette | TAGTTATCGAGCCCGGGGATCCACTAGTTCTAGTGTTTAA ACTCTAGCCG/GGGGATCCAGACATGATAAGATACATTGA TGAGTTTGGACAAACCACAACT | 59 |
| SDC-loxP-Hyg cassette/3' of rat C1q sequence | AGGATTACTGGCAGGGAGGAGGTTTTGGATAGGAGTGAT TTGACCCCGTGA/*GCTAGCATAACTTCGTATAGCATACATT ATACGAAGTTATCTAGGGGCTG* | 60 |

ES cells containing deletion of rat C1q sequences were identified by a quantitative TAQMAN™ assay modification of allele assay (MOA), described above. Table 11 identifies the names and locations of each of primers/probe sets used in the quantitative PCR assays. Same ES cells are used to introduce human C1q sequences to generate a chimeric rat as described below.

TABLE 11

Primer and Probes Used in a MOA Assay to Confirm Deletion of Rat C1q locus

| Description | Sequence | Loss of Allele (LOA) or Gain of Allele (GOA) | SEQ ID NO |
|---|---|---|---|
| RnoC1qTU2-Probe | AACCCACCGACGTATGGCAACGT | LOA (rat C1qa) | 61 |
| F | GCCAGCTTTCTCAGCTATTCG | | 62 |
| R | GCGGTTCTGGTATGGATTCTC | | 63 |
| RnoC1qTD-Probe | AAACACCTTCCAGGTCACCACGGG | LOA (rat C1qb) | 64 |
| F | TCTCACCTTCTGCGACTATGC | | 65 |
| R | CCTGCTCCAGCTTCAAGACTAC | | 66 |
| Hyg-Probe | ACGAGCGGGTTCGGCCCATTC | GOA (hygromycin) | 67 |
| F | TGCGGCCGATCTTAGCC | | 68 |
| R | TTGACCGATTCCTTGCGG | | 69 |
| LacZ Probe | CGATACTGTCGTCGTCCCCTCAAACTG | GOA (LacZ) | 70 |
| F | GGAGTGCGATCTTCCTGAGG | | 71 |
| R | CGCATCGTAACCGTGCATC | | 72 |

Targeted chimeric C1q Dark Agouti ES cells are implanted into Sprague Dawley rat embryos to generate F0 pups bearing deletion of C1q locus. F0 chimeric pups are bred to wild type rats to create F1 pups that are heterozygous for the genetic manipulation; the presence of the modified allele is confirmed by TAQMAN® assay as described above. F1 pups are subsequently bred to homozygosity.

Example 2.2. Generation of Humanized C1q Rat

Figure 2B:
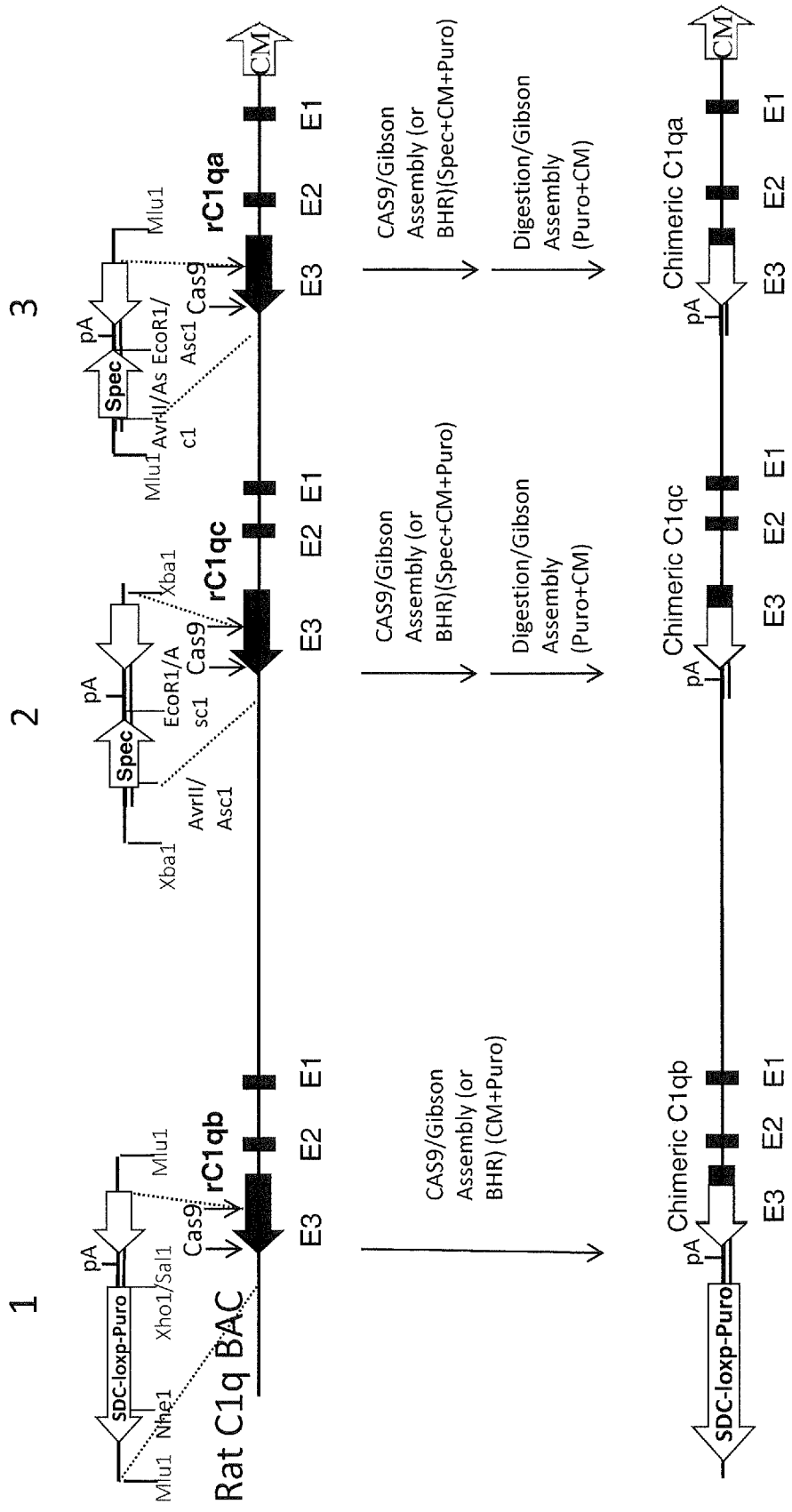
FIG. 2B shows a schematic representation (not to scale) of the creation of a humanized rat C1q cassette, with chimeric human/rat genes inserted by digestion/Gibson assembly and/or CAS9/Gibson assembly into the rat BAC genes (rat genes are indicated with "r" before the gene label). Exons of the three C1q genes are labeled below the diagram (e.g., E1, E2, and E3). Several restriction enzyme locations are indicated. CM=chloramphenicol; SDC-loxp-puro=self-deleting loxp-puromycin cassette.

To generate humanized C1q rat, plasmids were synthesized by Blue Heron using sequences for human C1q globular head domains (the same sequences as used for the humanized C1q mouse in Example 1 above) and overlapping rat sequences. For C1qb humanization construct, a self-deleting loxP-puromycin (SDC-loxp-Puro) selection cassette was inserted by restriction digest downstream of the human C1qb polyA sequence. For both C1qa and C1qc constructs, a spectinomycin (Spec) selection cassette was inserted by restriction digest downstream of each C1qa and C1qc polyA sequences. The resultant constructs are introduced sequentially into the Rat C1q BAC from LUCIGEN® through either a combination CRISPR/CAS9 technology and Gibson Assembly or bacterial homologous recombination (BHR) followed by selection and/or digestion steps to remove the selection cassettes, as demonstrated in FIG. 2B. In this particular embodiment, the chimeric nucleic acid sequence for C1qb was introduced by BHR first (1 in the figure), followed by BHR of chimeric C1qc DNA (2 in the figure), and then introduction by BHR of chimeric C1qa DNA (3 in the figure).

Figure 2C:
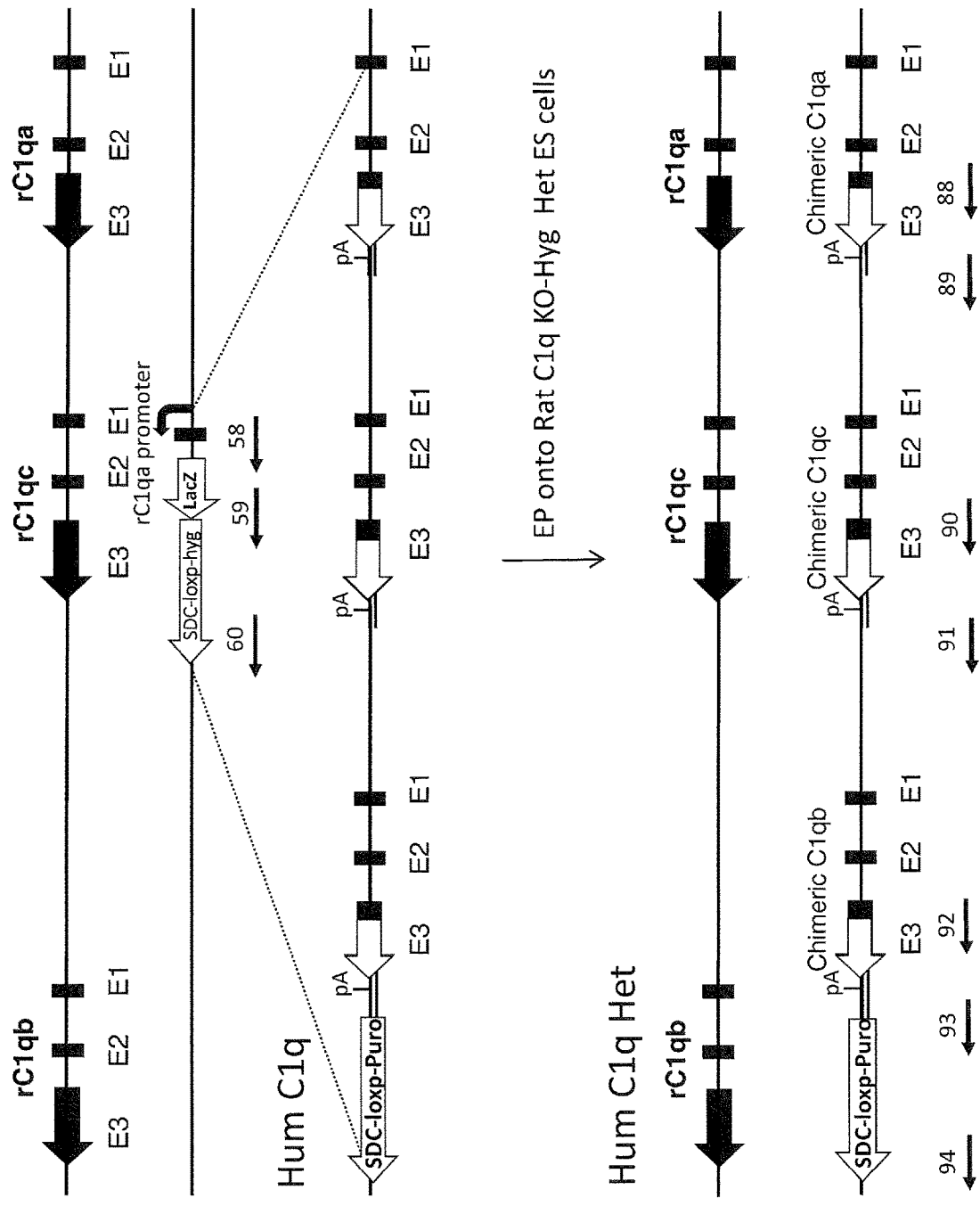
FIG. 2C shows a schematic representation (not to scale) of the electroporation (EP) of a large targeting vector containing all three rat/human chimeric C1q genes into rat C1q KO HET ES cells. Exons of the three C1q genes are labeled below the diagram (e.g., E1, E2, and E3). SDC-loxp-puro=self-deleting loxp-puromycin cassette; p=polyA sequence. Sequence junctions between rat, human, or cassette sequences are indicated with a line and a SEQ ID NO for that respective sequence below each junction.

The large targeting vector containing all three chimeric C1q genes was electroporated into Rat C1q KO HET ES cells as depicted in FIG. 2C, and successful integration was confirmed by a TAQMAN® real-time PCT-based modification of allele (MOA) assay. Primers and probes used for the MOA assay are described in Table 12.

TABLE 12

Primer and Probes Used in MOA Assay to Confirm Presence of Chimeric Human/Rat C1q genes

| Description | Sequence | Loss of Allele (LOA) or Gain of Allele (GOA) | SEQ ID NO |
|---|---|---|---|
| RnoC1qTU2-Probe | AACCCACCGACGTATGGCAACGT | LOA (rat C1qa) | 73 |
| F | GCCAGCTTTCTCAGCTATTCG | | 74 |
| R | GCGGTTCTGGTATGGATTCTC | | 75 |
| RnoC1qTD-Probe | AAACACCTTCCAGGTCACCACGGG | LOA (rat C1qb) | 76 |
| F | TCTCACCTTCTGCGACTATGC | | 77 |
| R | CCTGCTCCAGCTTCAAGACTAC | | 78 |
| 1565ha2-Probe | CCTTCCAGGTGCTGTCCCAGTG | GOA (human C1qa) | 79 |
| F | GTACCCGGCTACTACTACTTCA | | 80 |
| R | GAGACGATGGACAGGCAGATTTC | | 81 |
| 1565hb2 | ACCATCAACGTCCCCCTGCGC | GOA (human C1qb) | 82 |
| F | AATCGCCTTCTCTGCCACAA | | 83 |
| R | GTGGTCGAAGCGGATGGT | | 84 |
| 1565hc4 | CACCTGCAAAGTCCCCGGCCTC | GOA (human C1qc) | 85 |
| F | TGACACGAGCACTGGCAAGT | | 86 |
| R | CGACGCGTGGTAGACAAAGTAG | | 87 |

Junction sequences between various genetically engineered components at the chimeric locus are depicted in Table 13 below, and are indicated on the bottom schematic diagram in FIG. 2C. The junctions shown in Tables in this example only list short nucleotide sequences, but direct one skilled in the art to the location where the sequences were inserted into the rat genome.

TABLE 13

Junction Sequences of the Chimeric Human/Rat C1q Locus

| Junction Description | Sequence | SEQ ID NO |
|---|---|---|
| Rat C1qa exon 3/Human C1QA (globular domain) | GCCCCCAAGGGTTGAAAGGTGTGAAAGGCAATCCGGGC AATATCAGGGA/CCAGCCGAGGCCAGCCTTCTCCGCCATT CGGCGGAACCCCCCAATGGGGGGCA | 88 |
| Human C1QA UTR/3' of rat C1qa (non-coding) | GCATTGAGAGGGAGGCCTAAGAATAATAACAATCCA GTGCTTAAGAGTCAGGC/GCTGGGTAGCTGCCCCACG TTCTGCCATCTCCTGCACTCCCTGTTGCGGGGCC | 89 |
| Rat C1qc exon 3/human C1QC (globular domain) | GGGATCCAGGCCCCAGGGGTCCTCCCGGGGAGCCG GGTGAGGAGGGTCG/ATACAAGCAGAAATTCCAGTC AGTGTTCACGGTCACTCGGCAGACCCACCAGCCCC | 90 |
| Human C1QC 3'UTR/3' of rat C1qc (non-coding) | TGAATTTCGGATCTTCAACTTTGCATCAGCCATAG CTGGGCTCTGGACTC/GAATGGCAGGCTGGGTCCA GCACCCGGACGCCCGCCTCGCTCCCTCTGCT | 91 |
| Rat C1qb exon 3/human C1QB (globular domain) | GCCCCCCTGGACCCCGCGGTCCCAAAGGTGACTCTGG AGACTACAAGGCTACC/CAGAAAATCGCCTTCTCTGCCA CAAGAACCATCAACGTCCCCCTGCGCCGG | 92 |
| Human C1QB 3UTR/SDC-loxP-puro region | CTGGCACACCAGAAGTGCCATGCTCAGAAATGTTGGTT ACATGAATGAAT/GTCGAGATAACTTCGTATAATGTATG CTATACGAAGTTATATGCATGCCAG | 93 |

TABLE 13-continued

Junction Sequences of the Chimeric Human/Rat C1q Locus

| Junction Description | Sequence | SEQ ID NO |
|---|---|---|
| SDC-loxP-puro region/1-Ceu site/3' of rat C1qb (non-coding) | GGCGGCCTAGATAACTTCGTATAATGTATGCTATACG AAGTTATGCTAGG/TAACTATAACGGTCCTAAG GTAGCGA/GCTAGCTCACGGGGTCAAATCACTCCTATC CAAAACCTCCTCCCTGCCAGTAATCC | 94 |

Targeted chimeric C1q Dark Agouti ES cells are implanted into Sprague Dawley rat embryos to generate F0 pups bearing the chimeric human/rat C1q locus. F0 chimeric pups are bred to wild type rats to create F1 pups that are heterozygous for the genetic manipulation; the presence of the modified allele is confirmed by TAQMAN® assay as described above. F pups are subsequently bred to homozygosity.

Example 3: Characterization of Humanized C1q Mouse

Example 3.1: Chimeric C1q is Present and Functional in Mouse Serum

In order to determine if chimeric C1q was expressed and functional in mouse serum, humanized C1q mice were phenotyped by Western blot and classical complement hemolysis assay. All mice were housed and bred in the specific pathogen-free facility at Regeneron Pharmaceuticals. All animal experiments were approved by IACUC and Regeneron Pharmaceuticals.

(1) Western Blot:

Serum C1q concentrations were assayed in 1615 HO mice (mice homozygous for humanized C1q as described above) using Western blot, as follows: mouse or normal human serum (NHS) were diluted in PBS. Normal human serum (Quidel) was used as a positive control. Serum was added to electorophoresis sample loading buffer containing mercaptoethanol and SDS and run on a polyacrylamide gel under reducing/denaturing conditions, then transferred onto nitrocellulose membrane. Blots were blocked, then probed with goat anti-human C1q primary antibody (Quidel), followed by detection with donkey anti-goat IgG HRP (Santa Cruz). ThermoScientific Super Signal West Pico Chemiluminescent Subtrate was used to develop the blot. GE Image Quant LAS4000 was used for imaging.

(2) Classical Pathway Hemolysis Assay:

Desired number of SRBC (sheep red blood cells) were washed in GVB++ buffer and re suspended at $1 \times 10^9$ cells/mL and opsonized with rabbit anti-sheep hemolysin. Sensitized SRBC were diluted to $2 \times 10^8$ cells/mL in GVB++ buffer prior to using in hemolysis assay. Serum from WT littermates (n=5) and 1615HO (n=4) mice was collected at seven to nine weeks of age. Mouse serum was serially diluted in a 6 point, 2-fold dilution series from 1/5 to 1/160 with GVB++ buffer (100 ul diluted serum/well). Immediately, 100 uL of sensitized SRBCs (at $2 \times 10^8$ cells/mL) were added, for a total volume of 200 uL, and incubated 1 hr at 37° C. After the incubation time, cells were spun down by centrifugation at 1250×g at 4° C. A total of 100 uL of the supernatant was transferred to a fresh 96-well flat bottom plate and read at 541 nm on a Molecular Devices Spectramax M5 microplate reader and SoftMax Pro software. The hemolytic activity was calculated: OD541 of all experimental samples was divided by the OD541 at Maximum cell lysis (cells treated with 100 uL water) and then multiplied by 100. Data represented are single points (duplicates not run).

Figure 4:
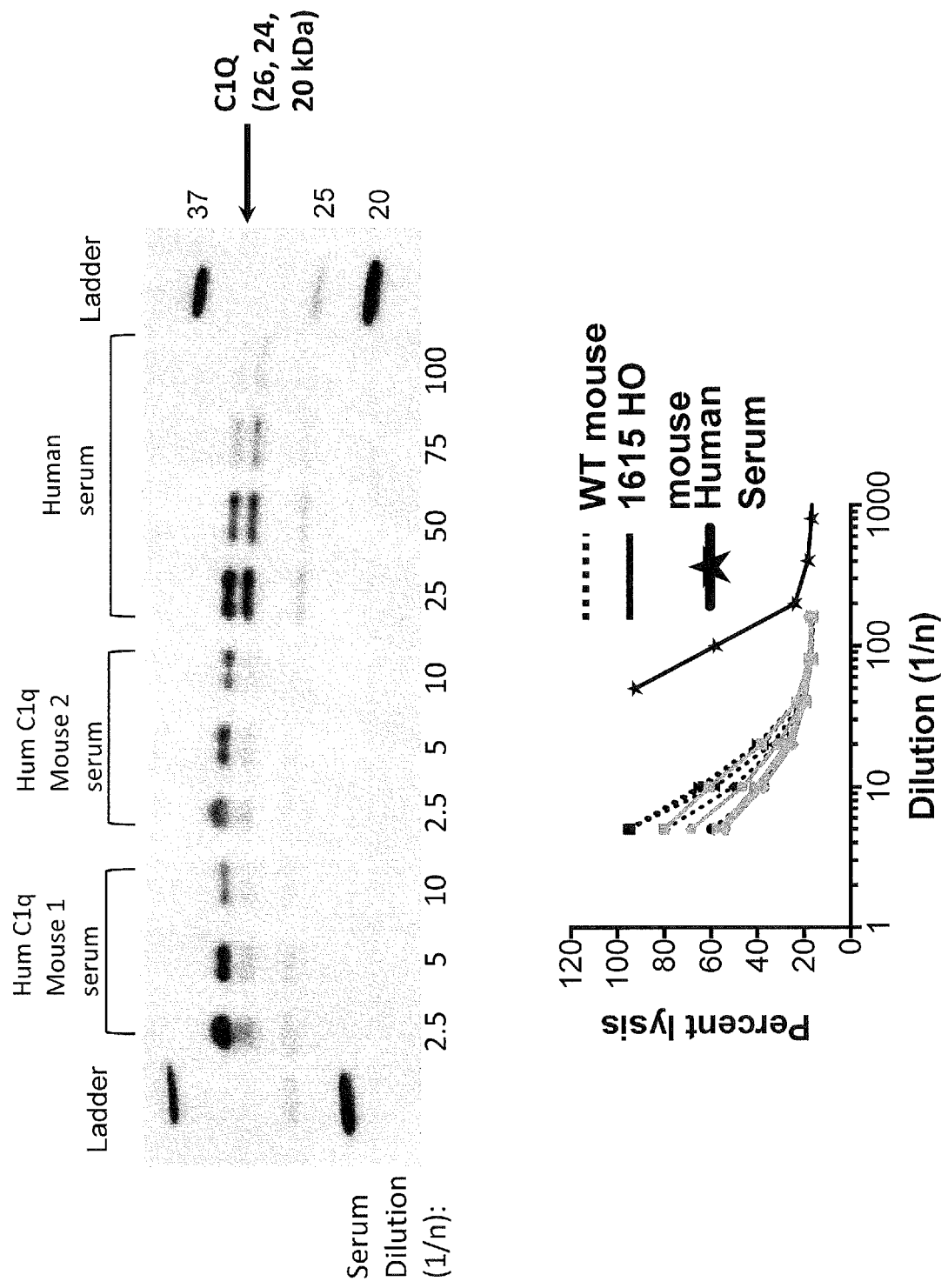
FIG. 4 top panel shows the presence chimeric C1q proteins in the serum of humanized C1q mice as detected by anti-human C1q antibody.

As demonstrated in FIG. 4, top panel, chimeric C1q proteins, as detected by anti-human C1q antibody, were detected in the serum of humanized C1q mice, albeit less C1q protein was detected in humanized C1q mouse serum than in human serum. The chimeric C1q protein obtained from the humanized mouse displayed similar classical complement activity as measured by hemolysis assay to that observed in the mice comprising wild type mouse C1q (FIG. 4, bottom panel).

The concentration of chimeric human/mouse C1q in mouse serum was also determined using a sandwich ELISA format with antibodies specific for human head of C1q. The standard curve was generated using a known concentration of human C1q protein, and the concentration of chimeric C1q in mouse serum was determined to be in the range of about 10-30 ug/mL.

Example 4: Humanized C1q Mouse as a Model for Testing Human Therapeutics

To confirm whether the humanized C1q mouse can serve as a model for testing human therapeutics, we first developed an in vitro assay to assess the ability of humanized C1q to activate complement dependent cytotoxicity (CDC) of Raji cells (B cells expressing cell-surface antigen CD20) by binding to human anti-CD20 antibody. Therapeutic anti-CD20 antibodies against the B-cell specific cell-surface antigen CD20 have been shown to lead to CDC of B-cells (Glennie et al. 2007, *Mechanisms of killing by anti-CD20 monoclonal antibodies*, Mol. Immunol., Vol. 44(16) pp. 3823-37) and CDC assay using cell lines expressing CD20 has been described previously (Flieger et al. 2000, *Mechanisms of Cytotoxicity Induced by Chimeric Mouse Human Monoclonal Antibody IDEC-C2BB in CD20-Expressing Lymphoma Lines*, Cell Immunol., Vol. 204(1) pp. 55-63).

For the CDC bioassay, Raji cells were seeded onto a 96-well assay plates at 10.000 cells/well in 1% BSA containing RPMI 1640. To measure CDC with human or mouse serum (from either humanized C1q or WT mice), the human anti-CD20 antibody was diluted 1:4 from 2 nM to 0.007 nM and incubated with cells for 10 minutes at 25° C. At the conclusion of the incubation with the anti-CD20 antibody, the serum was added to cells at a final concentration of 1%. Cytotoxicity was measured after 1 hour of incubation at 37° C. and in 5% CO2, followed by a 30 minute incubation at 25° C., and addition of CytoTox-Glo™ reagent (Promega, # G9291). CytoTox-Glo™ is a luminescence-based reagent that measures cell killing such that increased luminescence is observed with increased cytotoxicity (measured in relative light units, RLUs). Untreated cells in control wells were lysed by treatment with digitonin 10 minutes before addition of CytoTox-Glo™ reagent to determine maximal killing of cells. Plates were read for luminescence by a Victor X instrument (Perkin Elmer) 10-15 minutes following the addition of CytoTox-Glo™. Where calculated, the percentage of cytotoxicity was calculated with the RLU values by using the following equation:

$$\% \text{ Cytoxicity} = 100 \times \frac{(\text{Experimental Cell Lysis} - \text{Background Cell Lysis})}{(\text{Maximum Cell Lysis} - \text{Background Cell Lysis})}$$

In this equation "background cell lysis" is the luminescence from the cells treated with media and serum alone without any anti-CD20 antibody and the "maximum cell lysis" is the luminescence from the cells treated with digitonin. The results, expressed as % cytotoxicity or RLUs, were analyzed using nonlinear regression (4-parameter logistics) with Prism 7 software (GraphPad).

Figure 5:
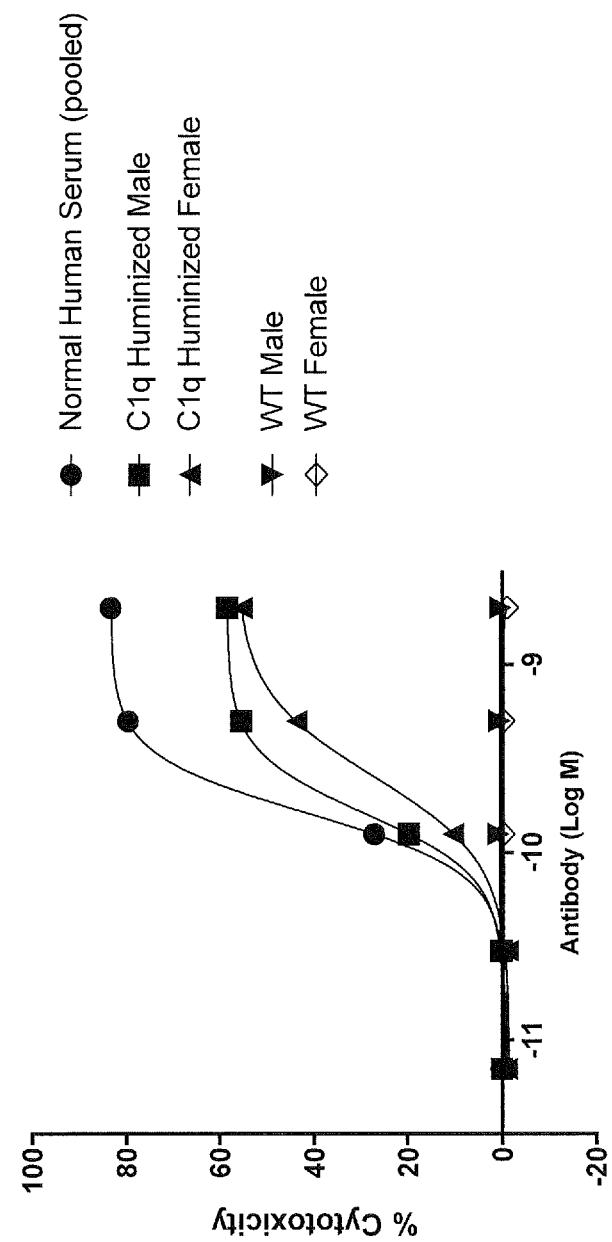
FIG. 5 shows complement dependent cytotoxicity (CDC) activity mediated by a human anti-CD20 antibody at 2 nM and a serum sample (normal human serum, humanized C1q mouse serum, or wild type mouse serum) on Raji cells.

Complement dependent cytotoxicity (CDC) activity mediated by 2 nM human anti-CD20 antibody and normal human serum resulted in 83% of maximum lysis, while CDC mediated by 2 nM human CD20 antibody and serum from humanized C1q mice was 55-58% of maximum lysis (FIG. 5). No cell lysis was detected using wild type mouse serum. Thus, serum containing humanized C1q globular head led to more efficient complement dependent lysis of Raji cells mediated by the human anti-CD20 antibody compared to the serum containing wild-type mouse C1q protein.

For in vivo testing, *S. aureus* infection model was chosen. *S. aureus* is a major cause of bacteremia in patients, and these infections are often fatal. Mouse models of bacteremia have been developed by many laboratories using a variety of laboratory-adapted and clinical *S. aureus* isolates and in a variety of mouse backgrounds (O'Keeffe K M, et al. Infect Immun. 2015 September; 83(9):3445-57. Manipulation of Autophagy in Phagocytes Facilitates *Staphylococcus aureus* Bloodstream Infection; Rauch et al, Infect Immun. 2012 October; 80(10):3721-32. Abscess formation and alpha-hemolysin induced toxicity in a mouse model of *Staphylococcus aureus* peritoneal infection) to study the infection dynamics and effect of potential therapeutics. A bacteremia model was established to evaluate the activity of bispecific antibodies (bisAbs), with one arm targeting C1q and another arm targeting an antigen expressed on *S. aureus*, in both reducing bacterial burden and improving survival.

Humanized C1q mice and control wild type mice were infected intraperitoneally with $1.7 \times 10^8$ colony forming units (CFUs) per mouse in a 200 ul volume of *S. aureus* Newman grown to log phase, $OD_{600} \leq 1$, in TSB at 37° C. and washed 3 times in PBS. Immediately following infection, mice were dosed with 100 ug of each bisAb and isotype-matched antibody in a 100 ul volume, intraperitoneally. Mice were euthanized on Day 3 and kidneys were collected to determine organ burden. Briefly, kidneys were homogenized in 5.0 mL PBS using gentleMACS Octo Dissociator (Miltenyi Biotec). Tissue homogenate was diluted in PBS and multiples of 10-fold serial dilutions were plated on LB agar plates and incubated at 37° C. overnight. Next day individual colonies were counted to determine bacterial burden at that time point post-infection and results were reported as CFUs¡gram tissue.

BisAbs were tested alongside an isotype control antibody for efficacy in reducing bacterial kidney burden in female humanized C1q mice and WT control mice. Compared to mice treated with isotype control Ab, on day 3 after treatment, 2-4 log reduction of bacterial CFUs was detected in kidneys of bisAbs treated humanized C1q mice; however, similar to results obtained with isotype control antibody, no reduction in bacterial burden was observed in WT mice expressing endogenous mouse C1q treated with BisAbs (data not shown).

To examine the effect of the bisAbs on survival, humanized C1q mice were infected with $1.5 \times 10^8$ CFUs per mouse of *S. aureus* Newman and treated with test antibodies as described above. Instead of sacrificing the mice on Day 3, they were monitored until Day 18. Mice that lost 20% of their starting body weight were sacrificed and recorded as a death. The percentage of surviving animals was reported at the end of the study.

BisAb was tested alongside an isotype control antibody for efficacy in a survival study in humanized C1q female mice (n=9). As shown in Table 14, at the end of the study, on Day 18 post infection, 100% of the mice treated with BisAb survived, in comparison to 78% of the isotype control treated mice.

TABLE 14

Survival of Humanized C1q Mice in Bacteremia Model

| Ab | Survival at D18 post-infection (%) | Mice (n) |
|---|---|---|
| BisAb | 100 | 9 |
| Isotype Control | 78 | 9 |
| Sham (PBS) | 56 | 9 |

In conclusion, this study demonstrates that humanized C1q mice are a valuable model for testing therapeutic agents, such as antibodies (e.g., bispecific antibodies), which are directed against human C1q protein.

Example 5: Characterization of Humanized C1q Rat

In order to determine if chimeric C1q was functional in rat serum, humanized C1q rats described in Example 2 were phenotyped by classical complement hemolysis assay. Results were compared to C1q knock-out (KO) rats and normal human serum. All rats were 50% Dark Agouti 50%/o Sprague Dawley background. All rats were housed and bred in the specific pathogen-free facility at Regeneron Pharmaceuticals. All animal experiments were approved by IACUC and Regeneron Pharmaceuticals.

(1) Classical Pathway Hemolysis Assay

Desired number of SRBCs (sheep red blood cells) were washed in GVB++ buffer and re suspended at $1 \times 10^9$ cells/mL and opsonized with rabbit anti-sheep hemolysin. Sensitized SRBCs were diluted to $2 \times 10^8$ cells/mL in GVB++ buffer prior to using in hemolysis assay. Serum from WT (n=3 females and n=4 males), 100015 HO (homozygous humanized C1q rats) (n=5 females and n=6 males) and homozygous C1q knock-out rats (n=2 females) was collected at ten to seventeen weeks of age. Normal human serum (Quidel) was used as a positive control, while C1q depleted human serum (Quidel) was used as a negative control. Rat and human serum was serially diluted in a 12 point, 2-fold dilution series from 1/5 to 1/10240 with GVB++ buffer (100 ul diluted serum/well). Immediately, 100 uL of sensitized SRBCs (at $2 \times 10^8$ cells/mL) were added, for a total volume of 200 uL, and incubated 1 hr at 37° C. After the incubation time, cells were spun down by centrifugation at 1250×g at 4° C. A total of 100 uL of the supernatant was transferred to a fresh 96-well flat bottom plate and read at 412 nm on a Molecular Devices Spectramax M5 microplate reader and SoftMax Pro software. The hemolytic activity was calculated: OD541 of all experimental samples was divided by the OD541 at Maximum cell lysis (cells treated with 100 uL water) and then multiplied by 100. Data represented are single points (duplicates not run).

Figure 6:
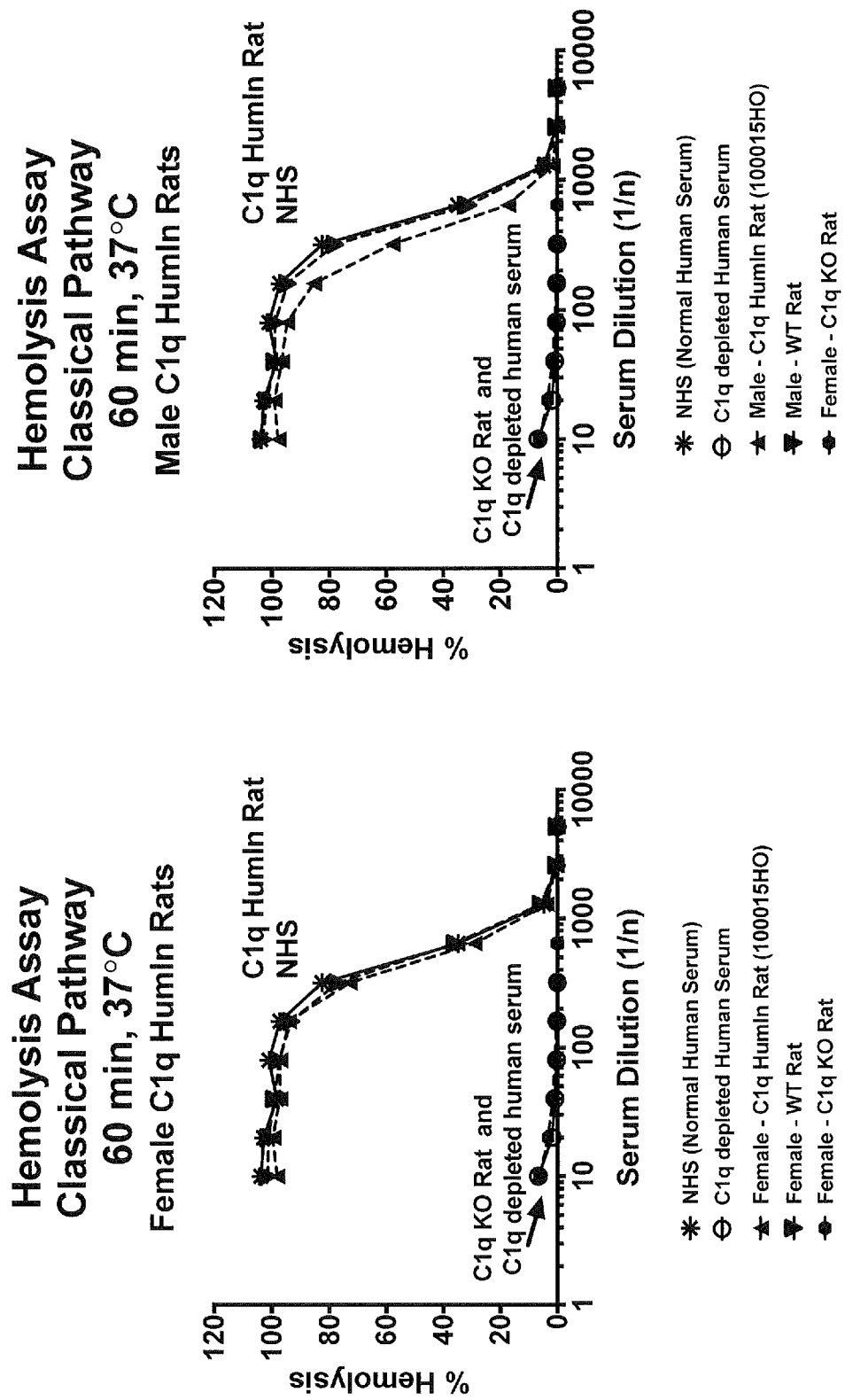
FIG. 6 shows results from a hemolysis assay measuring complement activity comparing serum samples from wild-type littermate rats ("WT"), humanized C1q rats ("C1q Humin" or 100015HO; HO=homozygous), C1q knock-out rats ("C1q KO"), normal human serum ("NHS"), and C1q depleted human serum. Left panel: female rats; right panel, with the exception of C1q KO rats: male rats.

As shown in FIG. 6, the chimeric C1q protein obtained from humanized rats displayed similar classical complement activity as measured by hemolysis assay to that observed in the rats comprising wild type rat C1q, and to that observed with normal human serum. No differences were observed between male and female rats.

Example 6: Humanized C1q Rat as a Model for Testing Human Therapeutics

To confirm whether a humanized C1q rat can serve as a model for testing human therapeutics, an in vitro complement dependent cytotoxicity assay and a whole blood bacterial survival assay were performed.

(1) Complement Dependent Cytotoxicity (CDC) Assay

For the CDC bioassay, Raji cells (a human B cell line expressing CD20), a serum sample (complement preserved human serum, WT rat serum, or serum from a homozygous C1q humanized rat as described in Example 2), and an anti-CD20 antibody, were used.

Raji cells were seeded onto a 96-well assay plates at 10,000 cells/well in 1% BSA containing RPMI 1640. To measure CDC with human or rat serum, the anti-CD20 antibody was diluted 1:4 from 20 nM to 0.019 nM (including a control sample containing no antibody) and incubated with cells for 10 minutes at 25° C. followed by addition of 0.5% serum. Cytotoxicity was measured after 1 hour of incubation at 37° C. and in 5% CO2, followed by 30 minute incubation at 25° C., and addition of CytoTox-Glo™ reagent (Promega, # G9291). CytoTox-Glo™ is a luminescence-based reagent that measures cell killing such that increased luminescence is observed with increased cytotoxicity (measured in relative light units, RLUs). Untreated cells in control wells were lysed by treatment with digitonin immediately after addition of CytoTox-Glo™ reagent to determine maximal killing of cells. Plates were read for luminescence by a Victor X instrument (Perkin Elmer) 10-15 minutes following the addition of CytoTox-Glo™. Where calculated, the percentage of cytotoxicity was calculated with the RLU values by using the following equation:

$$\% \text{ Cytoxicity} = 100 \times \frac{(\text{Experimental Cell Lysis} - \text{Background Cell Lysis})}{(\text{Maximum Cell Lysis} - \text{Background Cell Lysis})}$$

In this equation "background cell lysis" is the luminescence from the cells treated with media and serum alone without any anti-CD20 antibody and the "maximum cell lysis" is the luminescence from the cells treated with digitonin. The results, expressed as % cytotoxicity or RLUs, were analyzed using nonlinear regression (4-parameter logistics) with Prism 7 software (GraphPad).

As shown in FIG. 7, complement dependent cytotoxicity activity mediated by 20 nM CD20 antibody and the humanized C1q rat (MAID10015) serum resulted in 85-90% maximum lysis of Raji cells, which was similar to lysis using wild type rat serum (93-112% lysis) and normal human serum (83% lysis). Humanization of the C1q molecule did not alter the complement dependent lysis of Raji cells mediated by the CD20 antibody as compared to the rat C1q.

(2) S. aureus Survival in C1q Humanized Rat Blood and the Effects of a Bispecific Antibody S. aureus survival in whole human blood can be assessed in an ex vivo assay to explore the role of complement and immune effector cells in modulating bacterial growth (Thammavongsa et al., J Exp Med. 2009 Oct. 26; 206(11): 2417-27). In this assay, the activity of a bispecific antibody targeting C1q and a S. aureus antigen in modulating S. aureus survival is measured where the bispecific antibody is added into whole blood and survival is assessed after 24 hours. This assay has been adapted in this Example to use C1q humanized rat blood and examine the functionality of the humanized chimeric C1q protein in mediating the effects of a bispecific antibody that specifically recognizes a S. aureus antigen and the human or humanized C1q protein but not the rat C1q protein. A bivalent monospecific antibody against the same S. aureus antigen was used as a control.

Briefly, a culture of S. aureus Newman was grown in RPMI overnight, washed in PBS, and resuspended to a concentration of $1.25 \times 10^8$ colony forming units (CFU)/mL in PBS and serially diluted to a concentration of $10^5$ CFU/mL. In duplicates, $10^4$ CFU of the S. aureus suspension was mixed with 100 ug/mL bispecific antibody, control antibody or no antibody and 100 uL of humanized C1q or wild type (WT) rat blood (in sodium citrate as anti-coagulant with additional 500 nM dabigatran to prevent clot formation). The samples were incubated in 96 well plates at 37° C. with shaking (100 rpm) for 24 hours. After incubation, 100 ul of agglutination lysis buffer (PBS supplemented with 200 U Streptokinase, 2 ug/mL RNase, 10 ug/mL DNase, 0.5% saponin, 100 ug trypsin per ml of PBS) was added to the samples and vigorously vortexed until the pellet disappeared. A total of 50 uL from each sample was serially diluted in PBS and plated onto LB agar plates for enumeration of CFUs.

In this assay, freshly drawn blood samples from 11 humanized C1q and 10 WT rats were tested. Percent survival of S. aureus after treatment with the bispecific or control antibodies was determined. The overall growth in rat blood in the absence of test antibody is normalized to 100%. Survival of S. aureus in the WT rat blood with the bispecific antibody treatment ranged from 58-131%, while the bispecific antibody treatment in C1q humanized rat blood resulted in 7-49% survival. Survival of S. aureus in the WT rat blood with the control antibody treatment ranged from 40-139%, and the control antibody treatment in C1q humanized rat blood resulted in 61-114% survival.

What is claimed is:

1. A genetically modified rodent comprising in its genome
   a. a nucleic acid encoding a chimeric C1qa polypeptide, wherein the chimeric C1qa polypeptide comprises (i) a globular head domain that is substantially identical to the globular head domain of a human C1qa polypeptide, and (ii) an N-terminal stalk-stem region that is substantially identical to the N-terminal stalk-stem region of an endogenous rodent C1qa polypeptide;
   b. a nucleic acid encoding a chimeric C1qb polypeptide, wherein the chimeric C1qb polypeptide comprises (i) a globular head domain that is substantially identical to the globular head domain of a human C1qb polypeptide, and (ii) an N-terminal stalk-stem region that is substantially identical to the N-terminal stalk-stem region of an endogenous rodent C1qb polypeptide; and
   c. a nucleic acid encoding a chimeric C1qc polypeptide, wherein the chimeric C1qc polypeptide comprises (i) a globular head domain that is substantially identical to the globular head domain of a human C1qc polypeptide, and (ii) an N-terminal stalk-stem region that is substantially identical to the N-terminal stalk-stem region of an endogenous rodent C1qc polypeptide;
   wherein the genetically modified rodent does not express the endogenous rodent C1qa polypeptide, the endogenous rodent C1qb polypeptide, or the endogenous rodent C1qc polypeptide; and
   wherein the chimeric C1qa, C1qb and C1qc polypeptides are expressed in the rodent and form a functional C1q complex.

2. The genetically modified rodent of claim 1, wherein the rodent is a rat or a mouse.

3. The genetically modified rodent of claim 1, wherein the chimeric C1qa polypeptide comprises the signal peptide of the endogenous rodent C1qa polypeptide, the chimeric C1qb polypeptide comprises the signal peptide of the endogenous rodent C1qb polypeptide, and the chimeric C1qc polypeptide comprises the signal peptide of the endogenous rodent C1qc polypeptide.

4. The genetically modified rodent of claim 1, wherein the nucleic acid encoding the chimeric C1qa polypeptide is at the endogenous rodent C1qa locus, the nucleic acid encoding the chimeric C1qb polypeptide is at the endogenous rodent C1qb locus, and the nucleic acid encoding the chimeric C1qc polypeptide is at the endogenous rodent C1qc locus.

5. The genetically modified rodent of claim 4, wherein the nucleic acid encoding the chimeric C1qa polypeptide results from a replacement of a rodent genomic sequence at the endogenous rodent C1qa locus by a human C1qa nucleic acid sequence, the nucleic acid encoding the chimeric C1qb polypeptide results from a replacement of a rodent genomic sequence at the endogenous rodent C1qb locus by a human C1qb nucleic acid sequence, and the nucleic acid encoding the chimeric C1qc polypeptide results from a replacement of a rodent genomic sequence at the endogenous rodent C1qc locus by a human C1qc nucleic acid sequence.

6. The genetically modified rodent of claim 5, wherein the human C1qa nucleic acid sequence is a genomic fragment of a human C1qa gene, the human C1qb nucleic acid sequence is a genomic fragment of a human C1qb gene, and the human C1qc nucleic acid sequence is a genomic fragment of a human C1qc gene.

7. The genetically modified rodent of claim 6, wherein each genomic fragment comprises the 3' UTR of the corresponding human C1q gene.

8. The genetically modified rodent of claim 4, wherein the rodent is a rat and wherein:
   a. the nucleic acid encoding the chimeric C1qa polypeptide comprises, 5' to 3' and in operable linkage, a first nucleotide sequence encoding amino acids 1-111 of a rat C1qa polypeptide of SEQ ID NO: 7 and a second nucleotide sequence encoding amino acids 112-245 of a human C1qa polypeptide of SEQ ID NO: 4;
   b. the nucleic acid encoding the chimeric C1qb polypeptide comprises, 5' to 3' and in operable linkage, a third nucleotide sequence encoding amino acids 1-117 of a rat C1qb polypeptide of SEQ ID NO: 8 and a fourth nucleotide sequence encoding amino acids 118-251 of a human C1qb polypeptide of SEQ ID NO: 5; and
   c. the nucleic acid encoding the chimeric C1qc polypeptide comprises, 5' to 3' and in operable linkage, a fifth nucleotide sequence encoding amino acids 1-116 of a rat C1qc polypeptide of SEQ ID NO: 9 and a sixth nucleotide sequence encoding amino acids 114-245 of a human C1qc polypeptide of SEQ ID NO: 6.

9. The genetically modified rodent of claim 4, wherein the rodent is a mouse and wherein:
  a. the nucleic acid encoding the chimeric C1qa polypeptide comprises, 5' to 3' and in operable linkage, a first nucleotide sequence encoding amino acids 1-111 of a mouse C1qa polypeptide of SEQ ID NO: 1 and a second nucleotide sequence encoding amino acids 112-245 of a human C1qa polypeptide of SEQ ID NO: 4;
  b. the nucleic acid encoding the chimeric C1qb polypeptide comprises, 5' to 3' and in operable linkage, a third nucleotide sequence encoding amino acids 1-117 of a mouse C1qb polypeptide of SEQ ID NO: 2 and a fourth nucleotide sequence encoding amino acids 118-251 of a human C1qb polypeptide of SEQ ID NO: 5; and
  c. the nucleic acid encoding the chimeric C1qc polypeptide comprises, 5' to 3' and in operable linkage, a fifth nucleotide sequence encoding amino acids 1-114 of a mouse C1qc polypeptide of SEQ ID NO: 3 and a sixth nucleotide sequence encoding amino acids 114-245 of a human C1qc polypeptide of SEQ ID NO: 6.

10. The genetically modified rodent of claim 4, wherein the globular head domain of a human C1qa polypeptide comprises amino acids 108-245 of SEQ ID NO: 4.

11. The genetically modified rodent of claim 4, wherein the rodent is a mouse, wherein the chimeric C1qa polypeptide comprises an N-terminal stalk-stem region substantially identical to the N-terminal stalk-stem region of the endogenous mouse C1qa polypeptide, and wherein the N-terminal stalk-stem region of the endogenous mouse C1qa polypeptide comprises amino acids 23-107 of SEQ ID NO: 1.

12. The genetically modified rodent of claim 4, wherein the rodent is a mouse, and wherein the chimeric C1qa polypeptide comprises amino acids 23-245 of SEQ ID NO: 10.

13. The genetically modified rodent of claim 4, wherein the rodent is a rat, wherein the chimeric C1qa polypeptide comprises an N-terminal stalk-stem region substantially identical to the N-terminal stalk-stem region of the endogenous rat C1qa polypeptide, and wherein the N-terminal stalk-stem region of the endogenous rat C1qa polypeptide comprises amino acids 23-107 of SEQ ID NO: 7.

14. The genetically modified rodent of claim 4, wherein the rodent is a rat, and wherein the chimeric C1qa polypeptide comprises amino acids 23-245 of SEQ ID NO: 55.

15. The genetically modified rodent of claim 4, wherein the globular head domain of a human C1qb polypeptide comprises amino acids 115-251 of SEQ ID NO: 5.

16. The genetically modified rodent of claim 4, wherein the rodent is a mouse, wherein the chimeric C1qb polypeptide comprises an N-terminal stalk-stem region substantially identical to the N-terminal stalk-stem region of the endogenous mouse C1qb polypeptide, and wherein the N-terminal stalk-stem region of the endogenous mouse C1qb polypeptide comprises amino acids 26-114 of SEQ ID NO: 2.

17. The genetically modified rodent of claim 4, wherein the rodent is a mouse, and wherein the chimeric C1qb polypeptide comprises amino acids 26-251 of SEQ ID NO: 11.

18. The genetically modified rodent of claim 4, wherein the rodent is a rat, wherein the chimeric C1qb polypeptide comprises an N-terminal stalk-stem region substantially identical to the N-terminal stalk-stem region of the endogenous rat C1qb polypeptide, and wherein the N-terminal stalk-stem region of the endogenous rat C1qb polypeptide comprises amino acids 26-114 of SEQ ID NO: 8.

19. The genetically modified rodent of claim 4, wherein the rodent is a rat, and wherein the chimeric C1qb polypeptide comprises amino acids 26-251 of SEQ ID NO: 56.

20. The genetically modified rodent of claim 4, wherein the globular head domain of a human C1qc polypeptide comprises amino acids 113-245 of SEQ ID NO: 6.

21. The genetically modified rodent of claim 4, wherein the rodent is a mouse, wherein the chimeric C1qc polypeptide comprises an N-terminal stalk-stem region substantially identical to the N-terminal stalk-stem region of the endogenous mouse C1qc polypeptide, and wherein the N-terminal stalk-stem region of the endogenous mouse C1qc polypeptide comprises amino acids 30-113 of SEQ ID NO: 3.

22. The genetically modified rodent of claim 4, wherein the rodent is a mouse, and wherein the chimeric C1qc polypeptide comprises amino acids 30-246 of SEQ ID NO: 12.

23. The genetically modified rodent of claim 4, wherein the rodent is a rat, wherein the chimeric C1qc polypeptide comprises an N-terminal stalk-stem region substantially identical to the N-terminal stalk-stem region of the endogenous rat C1qc polypeptide, and wherein the N-terminal stalk-stem region of the endogenous rat C1qc polypeptide comprises amino acids 32-115 of SEQ ID NO: 9.

24. The genetically modified rodent of claim 4, wherein the rodent is a rat, and wherein the chimeric C1qc polypeptide comprises amino acids 32-248 SEQ ID NO: 57.

25. A rodent embryonic stem cell, comprising:
  a. at the endogenous C1qa locus a nucleic acid sequence encoding a chimeric C1qa polypeptide, wherein the chimeric C1qa polypeptide comprises a globular head domain that is substantially identical to the globular head domain of a human C1qa polypeptide, and an N-terminal stalk-stem region that is substantially identical to the N-terminal stalk-stem region of the endogenous rodent C1qa polypeptide;
  b. at the endogenous C1qb locus a nucleic acid sequence encoding a chimeric C1qb polypeptide, wherein the chimeric C1qb polypeptide comprises a globular head domain that is substantially identical to the globular head domain of a human C1qb polypeptide, and an N-terminal stalk-stem region that is substantially identical to the N-terminal stalk-stem region of the endogenous rodent C1qb polypeptide; and
  c. at the endogenous C1qc locus a nucleic acid sequence encoding a chimeric C1qc polypeptide, wherein the chimeric C1qc polypeptide comprises a globular head domain that is substantially identical to the globular head domain of a human C1qc polypeptide, and an N-terminal stalk-stem region that is substantially identical to the N-terminal stalk-stem region of the endogenous rodent C1qc polypeptide.

* * * * *

SEQUENCE LISTING

<160> NUMBER OF SEQ ID NOS: 94

<210> SEQ ID NO 1
<211> LENGTH: 245
<212> TYPE: PRT

<213> ORGANISM: Mus musculus

<400> SEQUENCE: 1

Met Glu Thr Ser Gln Gly Trp Leu Val Ala Cys Val Leu Thr Met Thr
1               5                   10                  15

Leu Val Trp Thr Val Ala Glu Asp Val Cys Arg Ala Pro Asn Gly Lys
            20                  25                  30

Asp Gly Ala Pro Gly Asn Pro Gly Arg Pro Gly Arg Pro Gly Leu Lys
        35                  40                  45

Gly Glu Arg Gly Glu Pro Gly Ala Ala Gly Ile Arg Thr Gly Ile Arg
    50                  55                  60

Gly Phe Lys Gly Asp Pro Gly Glu Ser Gly Pro Pro Gly Lys Pro Gly
65                  70                  75                  80

Asn Val Gly Leu Pro Gly Pro Ser Gly Pro Leu Gly Asp Ser Gly Pro
                85                  90                  95

Gln Gly Leu Lys Gly Val Lys Gly Asn Pro Gly Asn Ile Arg Asp Gln
            100                 105                 110

Pro Arg Pro Ala Phe Ser Ala Ile Arg Gln Asn Pro Met Thr Leu Gly
        115                 120                 125

Asn Val Val Ile Phe Asp Lys Val Leu Thr Asn Gln Glu Ser Pro Tyr
    130                 135                 140

Gln Asn His Thr Gly Arg Phe Ile Cys Ala Val Pro Gly Phe Tyr Tyr
145                 150                 155                 160

Phe Asn Phe Gln Val Ile Ser Lys Trp Asp Leu Cys Leu Phe Ile Lys
                165                 170                 175

Ser Ser Ser Gly Gly Gln Pro Arg Asp Ser Leu Ser Phe Ser Asn Thr
            180                 185                 190

Asn Asn Lys Gly Leu Phe Gln Val Leu Ala Gly Gly Thr Val Leu Gln
        195                 200                 205

Leu Arg Arg Gly Asp Glu Val Trp Ile Glu Lys Asp Pro Ala Lys Gly
    210                 215                 220

Arg Ile Tyr Gln Gly Thr Glu Ala Asp Ser Ile Phe Ser Gly Phe Leu
225                 230                 235                 240

Ile Phe Pro Ser Ala
                245

<210> SEQ ID NO 2
<211> LENGTH: 253
<212> TYPE: PRT
<213> ORGANISM: Mus musculus

<400> SEQUENCE: 2

Met Lys Thr Gln Trp Gly Glu Val Trp Thr His Leu Leu Leu Leu Leu
1               5                   10                  15

Leu Gly Phe Leu His Val Ser Trp Ala Gln Ser Ser Cys Thr Gly Pro
            20                  25                  30

Pro Gly Ile Pro Gly Ile Pro Gly Val Pro Gly Val Pro Gly Ser Asp
        35                  40                  45

Gly Gln Pro Gly Thr Pro Gly Ile Lys Gly Glu Lys Gly Leu Pro Gly
    50                  55                  60

Leu Ala Gly Asp Leu Gly Glu Phe Gly Glu Lys Gly Asp Pro Gly Ile
65                  70                  75                  80

Pro Gly Thr Pro Gly Lys Val Gly Pro Lys Gly Pro Val Gly Pro Lys
                85                  90                  95

Gly Thr Pro Gly Pro Ser Gly Pro Arg Gly Pro Lys Gly Asp Ser Gly

```
            100                 105                 110
Asp Tyr Gly Ala Thr Gln Lys Val Ala Phe Ser Ala Leu Arg Thr Ile
            115                 120                 125

Asn Ser Pro Leu Arg Pro Asn Gln Val Ile Arg Phe Glu Lys Val Ile
        130                 135                 140

Thr Asn Ala Asn Glu Asn Tyr Glu Pro Arg Asn Gly Lys Phe Thr Cys
145                 150                 155                 160

Lys Val Pro Gly Leu Tyr Tyr Phe Thr Tyr His Ala Ser Ser Arg Gly
                165                 170                 175

Asn Leu Cys Val Asn Leu Val Arg Gly Arg Asp Arg Asp Ser Met Gln
            180                 185                 190

Lys Val Val Thr Phe Cys Asp Tyr Ala Gln Asn Thr Phe Gln Val Thr
        195                 200                 205

Thr Gly Gly Val Val Leu Lys Leu Glu Gln Glu Val Val His Leu
    210                 215                 220

Gln Ala Thr Asp Lys Asn Ser Leu Leu Gly Ile Glu Gly Ala Asn Ser
225                 230                 235                 240

Ile Phe Thr Gly Phe Leu Leu Phe Pro Asp Met Asp Ala
                245                 250

<210> SEQ ID NO 3
<211> LENGTH: 246
<212> TYPE: PRT
<213> ORGANISM: Mus musculus

<400> SEQUENCE: 3

Met Val Val Gly Pro Ser Cys Gln Pro Pro Cys Gly Leu Cys Leu Leu
1               5                   10                  15

Leu Leu Phe Leu Leu Ala Leu Pro Leu Arg Ser Gln Ala Ser Ala Gly
            20                  25                  30

Cys Tyr Gly Ile Pro Gly Met Pro Gly Met Pro Gly Ala Pro Gly Lys
        35                  40                  45

Asp Gly His Asp Gly Leu Gln Gly Pro Lys Gly Glu Pro Gly Ile Pro
    50                  55                  60

Ala Val Pro Gly Thr Arg Gly Pro Lys Gly Gln Lys Gly Glu Pro Gly
65                  70                  75                  80

Met Pro Gly His Arg Gly Lys Asn Gly Pro Arg Gly Thr Ser Gly Leu
                85                  90                  95

Pro Gly Asp Pro Gly Pro Arg Gly Pro Pro Gly Glu Pro Gly Val Glu
            100                 105                 110

Gly Arg Tyr Lys Gln Lys His Gln Ser Val Phe Thr Val Thr Arg Gln
        115                 120                 125

Thr Thr Gln Tyr Pro Glu Ala Asn Ala Leu Val Arg Phe Asn Ser Val
130                 135                 140

Val Thr Asn Pro Gln Gly His Tyr Asn Pro Ser Thr Gly Lys Phe Thr
145                 150                 155                 160

Cys Glu Val Pro Gly Leu Tyr Tyr Phe Val Tyr Tyr Thr Ser His Thr
                165                 170                 175

Ala Asn Leu Cys Val His Leu Asn Leu Asn Leu Ala Arg Val Ala Ser
            180                 185                 190

Phe Cys Asp His Met Phe Asn Ser Lys Gln Val Ser Ser Gly Gly Val
        195                 200                 205

Leu Leu Arg Leu Gln Arg Gly Asp Glu Val Trp Leu Ser Val Asn Asp
    210                 215                 220
```

```
Tyr Asn Gly Met Val Gly Ile Glu Gly Ser Asn Ser Val Phe Ser Gly
225                 230                 235                 240

Phe Leu Leu Phe Pro Asp
                245
```

<210> SEQ ID NO 4
<211> LENGTH: 245
<212> TYPE: PRT
<213> ORGANISM: Homo sapiens

<400> SEQUENCE: 4

```
Met Glu Gly Pro Arg Gly Trp Leu Val Leu Cys Val Leu Ala Ile Ser
1               5                   10                  15

Leu Ala Ser Met Val Thr Glu Asp Leu Cys Arg Ala Pro Asp Gly Lys
                20                  25                  30

Lys Gly Glu Ala Gly Arg Pro Gly Arg Arg Gly Arg Pro Gly Leu Lys
            35                  40                  45

Gly Glu Gln Gly Glu Pro Gly Ala Pro Gly Ile Arg Thr Gly Ile Gln
50                  55                  60

Gly Leu Lys Gly Asp Gln Gly Glu Pro Gly Pro Ser Gly Asn Pro Gly
65                  70                  75                  80

Lys Val Gly Tyr Pro Gly Pro Ser Gly Pro Leu Gly Ala Arg Gly Ile
                85                  90                  95

Pro Gly Ile Lys Gly Thr Lys Gly Ser Pro Gly Asn Ile Lys Asp Gln
            100                 105                 110

Pro Arg Pro Ala Phe Ser Ala Ile Arg Arg Asn Pro Pro Met Gly Gly
        115                 120                 125

Asn Val Val Ile Phe Asp Thr Val Ile Thr Asn Gln Glu Glu Pro Tyr
130                 135                 140

Gln Asn His Ser Gly Arg Phe Val Cys Thr Val Pro Gly Tyr Tyr Tyr
145                 150                 155                 160

Phe Thr Phe Gln Val Leu Ser Gln Trp Glu Ile Cys Leu Ser Ile Val
                165                 170                 175

Ser Ser Ser Arg Gly Gln Val Arg Arg Ser Leu Gly Phe Cys Asp Thr
            180                 185                 190

Thr Asn Lys Gly Leu Phe Gln Val Val Ser Gly Gly Met Val Leu Gln
        195                 200                 205

Leu Gln Gln Gly Asp Gln Val Trp Val Glu Lys Asp Pro Lys Lys Gly
    210                 215                 220

His Ile Tyr Gln Gly Ser Glu Ala Asp Ser Val Phe Ser Gly Phe Leu
225                 230                 235                 240

Ile Phe Pro Ser Ala
                245
```

<210> SEQ ID NO 5
<211> LENGTH: 251
<212> TYPE: PRT
<213> ORGANISM: Homo sapiens

<400> SEQUENCE: 5

```
Met Lys Ile Pro Trp Gly Ser Ile Pro Val Leu Met Leu Leu Leu Leu
1               5                   10                  15

Leu Gly Leu Ile Asp Ile Ser Gln Ala Gln Leu Ser Cys Thr Gly Pro
                20                  25                  30

Pro Ala Ile Pro Gly Ile Pro Gly Ile Pro Gly Thr Pro Gly Pro Asp
            35                  40                  45
```

Gly Gln Pro Gly Thr Pro Gly Ile Lys Gly Glu Lys Gly Leu Pro Gly
 50              55                  60
Leu Ala Gly Asp His Gly Glu Phe Gly Lys Gly Asp Pro Gly Ile
65              70                  75                  80
Pro Gly Asn Pro Gly Lys Val Gly Pro Lys Gly Pro Met Gly Pro Lys
                85                  90                  95
Gly Gly Pro Gly Ala Pro Gly Ala Pro Gly Pro Lys Gly Glu Ser Gly
            100                 105                 110
Asp Tyr Lys Ala Thr Gln Lys Ile Ala Phe Ser Ala Thr Arg Thr Ile
            115                 120                 125
Asn Val Pro Leu Arg Arg Asp Gln Thr Ile Arg Phe Asp His Val Ile
        130                 135                 140
Thr Asn Met Asn Asn Tyr Glu Pro Arg Ser Gly Lys Phe Thr Cys
145                 150                 155                 160
Lys Val Pro Gly Leu Tyr Tyr Phe Thr Tyr His Ala Ser Ser Arg Gly
                165                 170                 175
Asn Leu Cys Val Asn Leu Met Arg Gly Arg Glu Arg Ala Gln Lys Val
            180                 185                 190
Val Thr Phe Cys Asp Tyr Ala Tyr Asn Thr Phe Gln Val Thr Thr Gly
        195                 200                 205
Gly Met Val Leu Lys Leu Glu Gln Gly Glu Asn Val Phe Leu Gln Ala
    210                 215                 220
Thr Asp Lys Asn Ser Leu Leu Gly Met Glu Gly Ala Asn Ser Ile Phe
225                 230                 235                 240
Ser Gly Phe Leu Leu Phe Pro Asp Met Glu Ala
                245                 250

<210> SEQ ID NO 6
<211> LENGTH: 245
<212> TYPE: PRT
<213> ORGANISM: Homo sapiens

<400> SEQUENCE: 6

Met Asp Val Gly Pro Ser Ser Leu Pro His Leu Gly Leu Lys Leu Leu
1               5                   10                  15
Leu Leu Leu Leu Leu Leu Pro Leu Arg Gly Gln Ala Asn Thr Gly Cys
                20                  25                  30
Tyr Gly Ile Pro Gly Met Pro Gly Leu Pro Gly Ala Pro Gly Lys Asp
            35                  40                  45
Gly Tyr Asp Gly Leu Pro Gly Pro Lys Gly Glu Pro Gly Ile Pro Ala
        50                  55                  60
Ile Pro Gly Ile Arg Gly Pro Lys Gly Gln Lys Gly Glu Pro Gly Leu
65              70                  75                  80
Pro Gly His Pro Gly Lys Asn Gly Pro Met Gly Pro Pro Gly Met Pro
                85                  90                  95
Gly Val Pro Gly Pro Met Gly Ile Pro Gly Glu Pro Gly Glu Glu Gly
            100                 105                 110
Arg Tyr Lys Gln Lys Phe Gln Ser Val Phe Thr Val Thr Arg Gln Thr
            115                 120                 125
His Gln Pro Pro Ala Pro Asn Ser Leu Ile Arg Phe Asn Ala Val Leu
        130                 135                 140
Thr Asn Pro Gln Gly Asp Tyr Asp Thr Ser Thr Gly Lys Phe Thr Cys
145                 150                 155                 160
Lys Val Pro Gly Leu Tyr Tyr Phe Val Tyr His Ala Ser His Thr Ala
                165                 170                 175

```
Asn Leu Cys Val Leu Leu Tyr Arg Ser Gly Val Lys Val Val Thr Phe
            180                 185                 190

Cys Gly His Thr Ser Lys Thr Asn Gln Val Asn Ser Gly Gly Val Leu
        195                 200                 205

Leu Arg Leu Gln Val Gly Glu Glu Val Trp Leu Ala Val Asn Asp Tyr
    210                 215                 220

Tyr Asp Met Val Gly Ile Gln Gly Ser Asp Ser Val Phe Ser Gly Phe
225                 230                 235                 240

Leu Leu Phe Pro Asp
                245

<210> SEQ ID NO 7
<211> LENGTH: 245
<212> TYPE: PRT
<213> ORGANISM: Rattus norvegicus

<400> SEQUENCE: 7

Met Glu Thr Ser Gln Gly Trp Leu Val Ala Cys Val Leu Ala Val Thr
1               5                   10                  15

Leu Val Trp Thr Val Ala Glu Asp Val Cys Arg Ala Pro Asn Gly Lys
            20                  25                  30

Asp Gly Val Ala Gly Ile Pro Gly Arg Pro Gly Arg Pro Gly Leu Lys
        35                  40                  45

Gly Glu Arg Gly Glu Pro Gly Ala Ala Gly Ile Arg Thr Gly Ile Arg
    50                  55                  60

Gly Leu Lys Gly Asp Met Gly Glu Ser Gly Pro Pro Gly Lys Pro Gly
65                  70                  75                  80

Asn Val Gly Phe Pro Gly Pro Thr Gly Pro Leu Gly Asn Ser Gly Pro
                85                  90                  95

Gln Gly Leu Lys Gly Val Lys Gly Asn Pro Gly Asn Ile Arg Asp Gln
            100                 105                 110

Pro Arg Pro Ala Phe Ser Ala Ile Arg Gln Asn Pro Pro Thr Tyr Gly
        115                 120                 125

Asn Val Val Val Phe Asp Lys Val Leu Thr Asn Gln Glu Asn Pro Tyr
130                 135                 140

Gln Asn Arg Thr Gly His Phe Ile Cys Ala Val Pro Gly Phe Tyr Tyr
145                 150                 155                 160

Phe Thr Phe Gln Val Ile Ser Lys Trp Asp Leu Cys Leu Ser Ile Val
                165                 170                 175

Ser Ser Ser Arg Gly Gln Pro Arg Asn Ser Leu Gly Phe Cys Asp Thr
            180                 185                 190

Asn Ser Lys Gly Leu Phe Gln Val Leu Ala Gly Gly Thr Val Leu Gln
        195                 200                 205

Leu Gln Arg Gly Asp Glu Val Trp Ile Glu Lys Asp Pro Ala Lys Gly
    210                 215                 220

Arg Ile Tyr Gln Gly Thr Glu Ala Asp Ser Ile Phe Ser Gly Phe Leu
225                 230                 235                 240

Ile Phe Pro Ser Ala
                245

<210> SEQ ID NO 8
<211> LENGTH: 253
<212> TYPE: PRT
<213> ORGANISM: Rattus norvegicus

<400> SEQUENCE: 8
```

```
Met Lys Thr Gln Trp Ser Glu Ile Leu Thr Pro Leu Leu Leu Leu
1               5                   10                  15

Leu Gly Leu Leu His Val Ser Trp Ala Gln Ser Ser Cys Thr Gly Ser
            20                  25                  30

Pro Gly Ile Pro Gly Val Pro Gly Ile Pro Gly Val Pro Gly Ser Asp
            35                  40                  45

Gly Lys Pro Gly Thr Pro Gly Ile Lys Gly Glu Lys Gly Leu Pro Gly
50                  55                  60

Leu Ala Gly Asp His Gly Glu Leu Gly Glu Lys Gly Asp Ala Gly Ile
65                  70                  75                  80

Pro Gly Ile Pro Gly Lys Val Gly Pro Lys Gly Pro Val Gly Pro Lys
            85                  90                  95

Gly Ala Pro Gly Pro Pro Gly Pro Arg Gly Pro Lys Gly Asp Ser Gly
            100                 105                 110

Asp Tyr Lys Ala Thr Gln Lys Val Ala Phe Ser Ala Leu Arg Thr Val
            115                 120                 125

Asn Ser Ala Leu Arg Pro Asn Gln Ala Ile Arg Phe Glu Lys Val Ile
130                 135                 140

Thr Asn Val Asn Asp Asn Tyr Glu Pro Arg Ser Gly Lys Phe Thr Cys
145                 150                 155                 160

Lys Val Pro Gly Leu Tyr Tyr Phe Thr Tyr His Ala Ser Ser Arg Gly
            165                 170                 175

Asn Leu Cys Val Asn Ile Val Arg Gly Arg Asp Arg Asp Arg Met Gln
            180                 185                 190

Lys Val Leu Thr Phe Cys Asp Tyr Ala Gln Asn Thr Phe Gln Val Thr
            195                 200                 205

Thr Gly Gly Val Val Leu Lys Leu Glu Gln Glu Val Val His Leu
            210                 215                 220

Gln Ala Thr Asp Lys Asn Ser Leu Leu Gly Val Glu Gly Ala Asn Ser
225                 230                 235                 240

Ile Phe Thr Gly Phe Leu Phe Pro Asp Met Asp Val
            245                 250

<210> SEQ ID NO 9
<211> LENGTH: 248
<212> TYPE: PRT
<213> ORGANISM: Rattus norvegicus

<400> SEQUENCE: 9

Met Leu Arg Met Val Val Gly Thr Ser Cys Gln Pro Gln His Gly Leu
1               5                   10                  15

Tyr Leu Leu Leu Leu Leu Ala Leu Pro Leu Arg Ser Gln Ala Asn
            20                  25                  30

Ala Gly Cys Tyr Gly Ile Pro Gly Met Pro Gly Leu Pro Gly Thr Pro
            35                  40                  45

Gly Lys Asp Gly His Asp Gly Leu Gln Gly Pro Lys Gly Glu Pro Gly
50                  55                  60

Ile Pro Ala Ile Pro Gly Thr Gln Gly Pro Lys Gly Gln Lys Gly Glu
65                  70                  75                  80

Pro Gly Met Pro Gly His Arg Gly Lys Asn Gly Pro Met Gly Thr Ser
            85                  90                  95

Gly Ser Pro Gly Asp Pro Gly Pro Arg Gly Pro Pro Gly Glu Pro Gly
            100                 105                 110

Glu Glu Gly Arg Tyr Lys Gln Lys His Gln Ser Val Phe Thr Val Thr
```

```
             115                 120                 125
Arg Gln Thr Ala Gln Tyr Pro Ala Ala Asn Gly Leu Val Lys Phe Asn
        130                 135                 140
Ser Ala Ile Thr Asn Pro Gln Gly Asp Tyr Asn Thr Asn Thr Gly Lys
145                 150                 155                 160
Phe Thr Cys Lys Val Pro Gly Leu Tyr Tyr Phe Val His His Thr Ser
                165                 170                 175
Gln Thr Ala Asn Leu Cys Val Gln Leu Leu Asn Asn Ala Lys Val
        180                 185                 190
Thr Ser Phe Cys Asp His Met Ser Asn Ser Lys Gln Val Ser Ser Gly
                195                 200                 205
Gly Val Leu Leu Arg Leu Gln Arg Gly Asp Glu Val Trp Leu Ala Val
        210                 215                 220
Asn Asp Tyr Asn Gly Met Val Gly Thr Glu Gly Ser Asp Ser Val Phe
225                 230                 235                 240
Ser Gly Phe Leu Leu Phe Pro Asp
                245

<210> SEQ ID NO 10
<211> LENGTH: 245
<212> TYPE: PRT
<213> ORGANISM: Artificial Sequence
<220> FEATURE:
<223> OTHER INFORMATION: polypeptide sequence of a chimeric mouse/human
      C1qa

<400> SEQUENCE: 10

Met Glu Thr Ser Gln Gly Trp Leu Val Ala Cys Val Leu Thr Met Thr
1               5                   10                  15
Leu Val Trp Thr Val Ala Glu Asp Val Cys Arg Ala Pro Asn Gly Lys
            20                  25                  30
Asp Gly Ala Pro Gly Asn Pro Gly Arg Pro Gly Arg Pro Gly Leu Lys
        35                  40                  45
Gly Glu Arg Gly Glu Pro Gly Ala Ala Gly Ile Arg Thr Gly Ile Arg
    50                  55                  60
Gly Phe Lys Gly Asp Pro Gly Glu Ser Gly Pro Pro Gly Lys Pro Gly
65                  70                  75                  80
Asn Val Gly Leu Pro Gly Pro Thr Gly Pro Leu Gly Asp Ser Gly Pro
                85                  90                  95
Gln Gly Leu Lys Gly Val Lys Gly Asn Pro Gly Asn Ile Arg Asp Gln
            100                 105                 110
Pro Arg Pro Ala Phe Ser Ala Ile Arg Arg Asn Pro Pro Met Gly Gly
        115                 120                 125
Asn Val Val Ile Phe Asp Thr Val Ile Thr Asn Gln Glu Glu Pro Tyr
    130                 135                 140
Gln Asn His Ser Gly Arg Phe Val Cys Thr Val Pro Gly Tyr Tyr Tyr
145                 150                 155                 160
Phe Thr Phe Gln Val Leu Ser Gln Trp Glu Ile Cys Leu Ser Ile Val
                165                 170                 175
Ser Ser Ser Arg Gly Gln Val Arg Arg Ser Leu Gly Phe Cys Asp Thr
            180                 185                 190
Thr Asn Lys Gly Leu Phe Gln Val Val Ser Gly Gly Met Val Leu Gln
        195                 200                 205
Leu Gln Gln Gly Asp Gln Val Trp Val Glu Lys Asp Pro Lys Lys Gly
    210                 215                 220
```

```
His Ile Tyr Gln Gly Ser Glu Ala Asp Ser Val Phe Ser Gly Phe Leu
225                 230                 235                 240

Ile Phe Pro Ser Ala
            245

<210> SEQ ID NO 11
<211> LENGTH: 251
<212> TYPE: PRT
<213> ORGANISM: Artificial Sequence
<220> FEATURE:
<223> OTHER INFORMATION: polypeptide sequence of a chimeric mouse/human
      C1qb

<400> SEQUENCE: 11

Met Lys Thr Gln Trp Gly Glu Val Trp Thr His Leu Leu Leu Leu Leu
1               5                   10                  15

Leu Gly Phe Leu His Val Ser Trp Ala Gln Ser Ser Cys Thr Gly Pro
            20                  25                  30

Pro Gly Ile Pro Gly Ile Pro Gly Val Pro Gly Val Pro Gly Ser Asp
        35                  40                  45

Gly Gln Pro Gly Thr Pro Gly Ile Lys Gly Glu Lys Gly Leu Pro Gly
    50                  55                  60

Leu Ala Gly Asp Leu Gly Glu Phe Gly Glu Lys Gly Asp Pro Gly Ile
65                  70                  75                  80

Pro Gly Thr Pro Gly Lys Val Gly Pro Lys Gly Pro Val Gly Pro Lys
                85                  90                  95

Gly Thr Pro Gly Pro Ser Gly Pro Arg Gly Pro Lys Gly Asp Ser Gly
            100                 105                 110

Asp Tyr Gly Ala Thr Gln Lys Ile Ala Phe Ser Ala Thr Arg Thr Ile
        115                 120                 125

Asn Val Pro Leu Arg Arg Asp Gln Thr Ile Arg Phe Asp His Val Ile
    130                 135                 140

Thr Asn Met Asn Asn Asn Tyr Glu Pro Arg Ser Gly Lys Phe Thr Cys
145                 150                 155                 160

Lys Val Pro Gly Leu Tyr Tyr Phe Thr Tyr His Ala Ser Ser Arg Gly
                165                 170                 175

Asn Leu Cys Val Asn Leu Met Arg Gly Arg Glu Arg Ala Gln Lys Val
            180                 185                 190

Val Thr Phe Cys Asp Tyr Ala Tyr Asn Thr Phe Gln Val Thr Thr Gly
        195                 200                 205

Gly Met Val Leu Lys Leu Glu Gln Gly Glu Asn Val Phe Leu Gln Ala
    210                 215                 220

Thr Asp Lys Asn Ser Leu Leu Gly Met Glu Gly Ala Asn Ser Ile Phe
225                 230                 235                 240

Ser Gly Phe Leu Leu Phe Pro Asp Met Glu Ala
                245                 250

<210> SEQ ID NO 12
<211> LENGTH: 246
<212> TYPE: PRT
<213> ORGANISM: Artificial Sequence
<220> FEATURE:
<223> OTHER INFORMATION: polypeptide sequence of a chimeric mouse/human
      C1qc

<400> SEQUENCE: 12

Met Val Val Gly Pro Ser Cys Gln Pro Pro Cys Gly Leu Cys Leu Leu
1               5                   10                  15
```

```
Leu Leu Phe Leu Ala Leu Pro Leu Arg Ser Gln Ala Ser Ala Gly
            20                  25                  30

Cys Tyr Gly Ile Pro Gly Met Pro Gly Met Pro Gly Ala Pro Gly Lys
        35                  40                  45

Asp Gly His Asp Gly Leu Gln Gly Pro Lys Gly Glu Pro Gly Ile Pro
    50                  55                  60

Ala Val Pro Gly Thr Arg Gly Pro Lys Gly Gln Lys Gly Glu Pro Gly
65                  70                  75                  80

Met Pro Gly His Arg Gly Lys Asn Gly Pro Arg Gly Thr Ser Gly Leu
                85                  90                  95

Pro Gly Asp Pro Gly Pro Arg Gly Pro Pro Gly Glu Pro Gly Val Glu
            100                 105                 110

Gly Arg Tyr Lys Gln Lys Phe Gln Ser Val Phe Thr Val Thr Arg Gln
            115                 120                 125

Thr His Gln Pro Pro Ala Pro Asn Ser Leu Ile Arg Phe Asn Ala Val
    130                 135                 140

Leu Thr Asn Pro Gln Gly Asp Tyr Asp Thr Ser Thr Gly Lys Phe Thr
145                 150                 155                 160

Cys Lys Val Pro Gly Leu Tyr Tyr Phe Val Tyr His Ala Ser His Thr
                165                 170                 175

Ala Asn Leu Cys Val Leu Leu Tyr Arg Ser Gly Val Lys Val Val Thr
            180                 185                 190

Phe Cys Gly His Thr Ser Lys Thr Asn Gln Val Asn Ser Gly Gly Val
            195                 200                 205

Leu Leu Arg Leu Gln Val Gly Glu Val Trp Leu Ala Val Asn Asp
    210                 215                 220

Tyr Tyr Asp Met Val Gly Ile Gln Gly Ser Asp Ser Val Phe Ser Gly
225                 230                 235                 240

Phe Leu Leu Phe Pro Asp
                245

<210> SEQ ID NO 13
<211> LENGTH: 67
<212> TYPE: DNA
<213> ORGANISM: Artificial Sequence
<220> FEATURE:
<223> OTHER INFORMATION: synthetic oligonucleotide

<400> SEQUENCE: 13
catacccagt gtccctgtgt gtctctgtag ggacaccatg ggtaccgatt taaatgatcc     60
agtggtc                                                              67

<210> SEQ ID NO 14
<211> LENGTH: 73
<212> TYPE: DNA
<213> ORGANISM: Artificial Sequence
<220> FEATURE:
<223> OTHER INFORMATION: synthetic oligonucleotide

<400> SEQUENCE: 14
gcagccccta gataacttcg tataatgtat gctatacgaa gttatcctag gctatccaac     60
accatcttcc tgc                                                       73

<210> SEQ ID NO 15
<211> LENGTH: 23
<212> TYPE: DNA
<213> ORGANISM: Artificial Sequence
<220> FEATURE:
```

<223> OTHER INFORMATION: synthetic oligonucleotide

<400> SEQUENCE: 15
tcccgcacca tcctggaggc aat                                    23

<210> SEQ ID NO 16
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 16
taagcgttct ctccggctgg                                        20

<210> SEQ ID NO 17
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 17
cgcttctcag gaccccctaaa c                                     21

<210> SEQ ID NO 18
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 18
cgatactgtc gtcgtcccct caaactg                                27

<210> SEQ ID NO 19
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 19
ggagtgcgat cttcctgagg                                        20

<210> SEQ ID NO 20
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 20
cgcatcgtaa ccgtgcatc                                         19

<210> SEQ ID NO 21
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 21
tgggcacaac agacaatcgg ctg                                    23

```
<210> SEQ ID NO 22
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 22
ggtggagagg ctattcggc                                                  19

<210> SEQ ID NO 23
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 23
gaacacggcg gcatcag                                                    17

<210> SEQ ID NO 24
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 24
aggaccatca acagcccctt gcgac                                           25

<210> SEQ ID NO 25
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 25
gaaagtcgcc ttctctgccc                                                 20

<210> SEQ ID NO 26
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 26
cgaagcgaat gacctggttc                                                 20

<210> SEQ ID NO 27
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 27
tgacaaggtc ctcaccaacc aggagag                                         27

<210> SEQ ID NO 28
<211> LENGTH: 19
<212> TYPE: DNA
<213> ORGANISM: Artificial Sequence
<220> FEATURE:
<223> OTHER INFORMATION: probe
```

```
<400> SEQUENCE: 28
cgcttggcaa cgtggttat                                              19

<210> SEQ ID NO 29
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 29
cccgtgtggt tctggtatgg                                             20

<210> SEQ ID NO 30
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 30
tatgagccac gcaacggcaa gttca                                       25

<210> SEQ ID NO 31
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 31
tcaccaacgc gaacgagaa                                              19

<210> SEQ ID NO 32
<211> LENGTH: 16
<212> TYPE: DNA
<213> ORGANISM: Artificial Sequence
<220> FEATURE:
<223> OTHER INFORMATION: synthetic oligonucleotide

<400> SEQUENCE: 32
ggccaggcac cttgca                                                 16

<210> SEQ ID NO 33
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 33
cccatcctca ctcagacctc ttcctcca                                    28

<210> SEQ ID NO 34
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 34
cacctcgctc cctctgctt                                              19

<210> SEQ ID NO 35
<211> LENGTH: 20
```

```
<212> TYPE: DNA
<213> ORGANISM: Artificial Sequence
<220> FEATURE:
<223> OTHER INFORMATION: synthetic oligonucleotide

<400> SEQUENCE: 35
caggaaccag ggtggacttc                                                        20

<210> SEQ ID NO 36
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 36
caacgtggtc atcttcgaca cggtca                                                 26

<210> SEQ ID NO 37
<211> LENGTH: 16
<212> TYPE: DNA
<213> ORGANISM: Artificial Sequence
<220> FEATURE:
<223> OTHER INFORMATION: synthetic oligonucleotide

<400> SEQUENCE: 37
cggaaccccc caatgg                                                            16

<210> SEQ ID NO 38
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 38
tggttctggt acggttcttc ct                                                     22

<210> SEQ ID NO 39
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 39
accatcaacg tccccctgcg c                                                      21

<210> SEQ ID NO 40
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 40
aatcgccttc tctgccacaa                                                        20

<210> SEQ ID NO 41
<211> LENGTH: 18
<212> TYPE: DNA
<213> ORGANISM: Artificial Sequence
<220> FEATURE:
<223> OTHER INFORMATION: probe

<400> SEQUENCE: 41
```

```
gtggtcgaag cggatggt                                                       18

<210> SEQ ID NO 42
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 42
cacctgcaaa gtccccggcc tc                                                  22

<210> SEQ ID NO 43
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 43
tgacacgagc actggcaagt                                                     20

<210> SEQ ID NO 44
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 44
cgacgcgtgg tagacaaagt ag                                                  22

<210> SEQ ID NO 45
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 45
acgagcgggt tcggcccatt c                                                   21

<210> SEQ ID NO 46
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 46
tgcggccgat cttagcc                                                        17

<210> SEQ ID NO 47
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 47
ttgaccgatt ccttgcgg                                                       18

<210> SEQ ID NO 48
<211> LENGTH: 103
<212> TYPE: DNA
<213> ORGANISM: Artificial Sequence
```

<220> FEATURE:
<223> OTHER INFORMATION: synthetic oligonucleotide

<400> SEQUENCE: 48
cggcccccaa ggactgaagg gcgtgaaagg caatccaggc aatatcaggg accagccgag    60
gccagccttc tccgccattc ggcggaaccc cccaatgggg ggc    103

<210> SEQ ID NO 49
<211> LENGTH: 104
<212> TYPE: DNA
<213> ORGANISM: Artificial Sequence
<220> FEATURE:
<223> OTHER INFORMATION: synthetic oligonucleotide

<400> SEQUENCE: 49
ttgagaggga ggcctaagaa taataacaat ccagtgctta agagtcaggc gcgatcgctg    60
atgcacgcct ttaatcccag cacttgggag gcagagacag gtga    104

<210> SEQ ID NO 50
<211> LENGTH: 105
<212> TYPE: DNA
<213> ORGANISM: Artificial Sequence
<220> FEATURE:
<223> OTHER INFORMATION: synthetic oligonucleotide

<400> SEQUENCE: 50
gccaggggac ccaggcccca gggggcctcc gggggagcca ggtgtggagg gccgatacaa    60
gcagaaattc cagtcagtgt tcacggtcac tcggcagacc cacca    105

<210> SEQ ID NO 51
<211> LENGTH: 99
<212> TYPE: DNA
<213> ORGANISM: Artificial Sequence
<220> FEATURE:
<223> OTHER INFORMATION: synthetic oligonucleotide

<400> SEQUENCE: 51
tgaatttcgg atcttcaact ttgcatcagc catagctggg ctctggactc tacctaacta    60
taacggtcct aaggtagcga aaggggatg atttggagt    99

<210> SEQ ID NO 52
<211> LENGTH: 110
<212> TYPE: DNA
<213> ORGANISM: Artificial Sequence
<220> FEATURE:
<223> OTHER INFORMATION: synthetic oligonucleotide

<400> SEQUENCE: 52
tccaggcccc tctggacccc gcggtcccaa aggcgattct ggggactacg ggctacaca    60 gaaaatcgcc ttctctgcca caagaaccat caacgtcccc ctgcgccggg    110

<210> SEQ ID NO 53
<211> LENGTH: 101
<212> TYPE: DNA
<213> ORGANISM: Artificial Sequence
<220> FEATURE:
<223> OTHER INFORMATION: synthetic oligonucleotide

<400> SEQUENCE: 53
gcacctggca caccagaagt gccatgctca gaaatgttgg ttacatgaat gaatgcggcc    60
gcaccggtat aacttcgtat aatgtatgct atacgaagtt a    101

<210> SEQ ID NO 54
<211> LENGTH: 101
<212> TYPE: DNA
<213> ORGANISM: Artificial Sequence
<220> FEATURE:
<223> OTHER INFORMATION: synthetic oligonucleotide

<400> SEQUENCE: 54
ccggcgcgcc ataacttcgt ataatgtatg ctatacgaag ttatgtcgac gaatgttcat    60
aggctgggga gatggctcag tcagtaaagt acttagcttg c                       101

<210> SEQ ID NO 55
<211> LENGTH: 245
<212> TYPE: PRT
<213> ORGANISM: Artificial Sequence
<220> FEATURE:
<223> OTHER INFORMATION: polypeptide sequence of a chimeric rat/human
      C1qa

<400> SEQUENCE: 55

Met Glu Thr Ser Gln Gly Trp Leu Val Ala Cys Val Leu Ala Val Thr
1               5                   10                  15

Leu Val Trp Thr Val Ala Glu Asp Val Cys Arg Ala Pro Asn Gly Lys
            20                  25                  30

Asp Gly Val Ala Gly Ile Pro Gly Arg Pro Gly Arg Pro Gly Leu Lys
        35                  40                  45

Gly Glu Arg Gly Glu Pro Gly Ala Ala Gly Ile Arg Thr Gly Ile Arg
    50                  55                  60

Gly Leu Lys Gly Asp Met Gly Glu Ser Gly Pro Gly Lys Pro Gly
65                  70                  75                  80

Asn Val Gly Phe Pro Gly Pro Thr Gly Pro Leu Gly Asn Ser Gly Pro
                85                  90                  95

Gln Gly Leu Lys Gly Val Lys Gly Asn Pro Gly Asn Ile Arg Asp Gln
            100                 105                 110

Pro Arg Pro Ala Phe Ser Ala Ile Arg Arg Asn Pro Pro Met Gly Gly
        115                 120                 125

Asn Val Val Ile Phe Asp Thr Val Ile Thr Asn Gln Glu Glu Pro Tyr
    130                 135                 140

Gln Asn His Ser Gly Arg Phe Val Cys Thr Val Pro Gly Tyr Tyr Tyr
145                 150                 155                 160

Phe Thr Phe Gln Val Leu Ser Gln Trp Glu Ile Cys Leu Ser Ile Val
                165                 170                 175

Ser Ser Ser Arg Gly Gln Val Arg Arg Ser Leu Gly Phe Cys Asp Thr
            180                 185                 190

Thr Asn Lys Gly Leu Phe Gln Val Val Ser Gly Gly Met Val Leu Gln
        195                 200                 205

Leu Gln Gln Gly Asp Gln Val Trp Val Glu Lys Asp Pro Lys Lys Gly
    210                 215                 220

His Ile Tyr Gln Gly Ser Glu Ala Asp Ser Val Phe Ser Gly Phe Leu
225                 230                 235                 240

Ile Phe Pro Ser Ala
                245

<210> SEQ ID NO 56
<211> LENGTH: 251
<212> TYPE: PRT
<213> ORGANISM: Artificial Sequence
<220> FEATURE:

<223> OTHER INFORMATION: polypeptide sequence of a chimeric rat/human C1qb

<400> SEQUENCE: 56

Met Lys Thr Gln Trp Ser Glu Ile Leu Thr Pro Leu Leu Leu Leu
1               5                   10                  15

Leu Gly Leu Leu His Val Ser Trp Ala Gln Ser Ser Cys Thr Gly Ser
            20                  25                  30

Pro Gly Ile Pro Gly Val Pro Gly Ile Pro Gly Val Pro Gly Ser Asp
            35                  40                  45

Gly Lys Pro Gly Thr Pro Gly Ile Lys Gly Glu Lys Gly Leu Pro Gly
        50                  55                  60

Leu Ala Gly Asp His Gly Glu Leu Gly Glu Lys Gly Asp Ala Gly Ile
65                  70                  75                  80

Pro Gly Ile Pro Gly Lys Val Gly Pro Lys Gly Pro Val Gly Pro Lys
            85                  90                  95

Gly Ala Pro Gly Pro Pro Gly Pro Arg Gly Pro Lys Gly Asp Ser Gly
            100                 105                 110

Asp Tyr Lys Ala Thr Gln Lys Ile Ala Phe Ser Ala Thr Arg Thr Ile
            115                 120                 125

Asn Val Pro Leu Arg Arg Asp Gln Thr Ile Arg Phe Asp His Val Ile
            130                 135                 140

Thr Asn Met Asn Asn Tyr Glu Pro Arg Ser Gly Lys Phe Thr Cys
145                 150                 155                 160

Lys Val Pro Gly Leu Tyr Tyr Phe Thr Tyr His Ala Ser Ser Arg Gly
            165                 170                 175

Asn Leu Cys Val Asn Leu Met Arg Gly Arg Glu Arg Ala Gln Lys Val
            180                 185                 190

Val Thr Phe Cys Asp Tyr Ala Tyr Asn Thr Phe Gln Val Thr Thr Gly
            195                 200                 205

Gly Met Val Leu Lys Leu Glu Gln Gly Glu Asn Val Phe Leu Gln Ala
            210                 215                 220

Thr Asp Lys Asn Ser Leu Leu Gly Met Glu Gly Ala Asn Ser Ile Phe
225                 230                 235                 240

Ser Gly Phe Leu Leu Phe Pro Asp Met Glu Ala
            245                 250

<210> SEQ ID NO 57
<211> LENGTH: 248
<212> TYPE: PRT
<213> ORGANISM: Artificial Sequence
<220> FEATURE:
<223> OTHER INFORMATION: polypeptide sequence of a chimeric rat/human C1qc

<400> SEQUENCE: 57

Met Leu Arg Met Val Val Gly Thr Ser Cys Gln Pro Gln His Gly Leu
1               5                   10                  15

Tyr Leu Leu Leu Leu Leu Leu Ala Leu Pro Leu Arg Ser Gln Ala Asn
            20                  25                  30

Ala Gly Cys Tyr Gly Ile Pro Gly Met Pro Gly Leu Pro Gly Thr Pro
            35                  40                  45

Gly Lys Asp Gly His Asp Gly Leu Gln Gly Pro Lys Gly Glu Pro Gly
        50                  55                  60

Ile Pro Ala Ile Pro Gly Thr Gln Gly Pro Lys Gly Gln Lys Gly Glu
65                  70                  75                  80

-continued

```
Pro Gly Met Pro Gly His Arg Gly Lys Asn Gly Pro Met Gly Thr Ser
            85                  90                  95
Gly Ser Pro Gly Asp Pro Gly Pro Arg Gly Pro Pro Gly Glu Pro Gly
        100                 105                 110
Glu Glu Gly Arg Tyr Lys Gln Lys Phe Gln Ser Val Phe Thr Val Thr
    115                 120                 125
Arg Gln Thr His Gln Pro Pro Ala Pro Asn Ser Leu Ile Arg Phe Asn
130                 135                 140
Ala Val Leu Thr Asn Pro Gln Gly Asp Tyr Asp Thr Ser Thr Gly Lys
145                 150                 155                 160
Phe Thr Cys Lys Val Pro Gly Leu Tyr Tyr Phe Val Tyr His Ala Ser
                165                 170                 175
His Thr Ala Asn Leu Cys Val Leu Leu Tyr Arg Ser Gly Val Lys Val
            180                 185                 190
Val Thr Phe Cys Gly His Thr Ser Lys Thr Asn Gln Val Asn Ser Gly
        195                 200                 205
Gly Val Leu Leu Arg Leu Gln Val Gly Glu Val Trp Leu Ala Val
    210                 215                 220
Asn Asp Tyr Tyr Asp Met Val Gly Ile Gln Gly Ser Asp Ser Val Phe
225                 230                 235                 240
Ser Gly Phe Leu Leu Phe Pro Asp
                245

<210> SEQ ID NO 58
<211> LENGTH: 103
<212> TYPE: DNA
<213> ORGANISM: Artificial Sequence
<220> FEATURE:
<223> OTHER INFORMATION: synthetic oligonucleotide

<400> SEQUENCE: 58
gattctccca atctctcctc tgcaggacca ctggatcatt taaatcggta cccatgatgt      60
tcctgcagag acacacaggg accccgggca tgctggacag tca                      103

<210> SEQ ID NO 59
<211> LENGTH: 101
<212> TYPE: DNA
<213> ORGANISM: Artificial Sequence
<220> FEATURE:
<223> OTHER INFORMATION: synthetic oligonucleotide

<400> SEQUENCE: 59
tagttatcga gcccggggat ccactagttc tagtgtttaa actctagccg ggggatccag      60
acatgataag atacattgat gagtttggac aaaccacaac t                        101

<210> SEQ ID NO 60
<211> LENGTH: 101
<212> TYPE: DNA
<213> ORGANISM: Artificial Sequence
<220> FEATURE:
<223> OTHER INFORMATION: synthetic oligonucleotide

<400> SEQUENCE: 60
aggattactg gcagggagga ggttttggat aggagtgatt tgaccccgtg agctagcata      60
acttcgtata gcatacatta tacgaagtta tctaggggct g                        101

<210> SEQ ID NO 61
<211> LENGTH: 23
<212> TYPE: DNA
```

```
<213> ORGANISM: Artificial Sequence
<220> FEATURE:
<223> OTHER INFORMATION: synthetic oligonucleotide

<400> SEQUENCE: 61
aacccaccga cgtatggcaa cgt                                              23

<210> SEQ ID NO 62
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 62
gccagctttc tcagctattc g                                                21

<210> SEQ ID NO 63
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 63
gcggttctgg tatggattct c                                                21

<210> SEQ ID NO 64
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 64
aaacaccttc caggtcacca cggg                                             24

<210> SEQ ID NO 65
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 65
tctcaccttc tgcgactatg c                                                21

<210> SEQ ID NO 66
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 66
cctgctccag cttcaagact ac                                               22

<210> SEQ ID NO 67
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 67
acgagcgggt tcggcccatt c                                                21
```

```
<210> SEQ ID NO 68
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 68
tgcggccgat cttagcc                                                      17

<210> SEQ ID NO 69
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 69
ttgaccgatt ccttgcgg                                                     18

<210> SEQ ID NO 70
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 70
cgatactgtc gtcgtcccct caaactg                                           27

<210> SEQ ID NO 71
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 71
ggagtgcgat cttcctgagg                                                   20

<210> SEQ ID NO 72
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 72
cgcatcgtaa ccgtgcatc                                                    19

<210> SEQ ID NO 73
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 73
aacccaccga cgtatggcaa cgt                                               23

<210> SEQ ID NO 74
<211> LENGTH: 21
<212> TYPE: DNA
<213> ORGANISM: Artificial Sequence
<220> FEATURE:
```

<223> OTHER INFORMATION: synthetic oligonucleotide

<400> SEQUENCE: 74
gccagctttc tcagctattc g                                      21

<210> SEQ ID NO 75
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 75
gcggttctgg tatggattct c                                      21

<210> SEQ ID NO 76
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 76
aaacaccttc caggtcacca cggg                                   24

<210> SEQ ID NO 77
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 77
tctcaccttc tgcgactatg c                                      21

<210> SEQ ID NO 78
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 78
cctgctccag cttcaagact ac                                     22

<210> SEQ ID NO 79
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 79
ccttccaggt gctgtcccag tg                                     22

<210> SEQ ID NO 80
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 80
gtacccggct actactactt ca                                     22

<210> SEQ ID NO 81
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 81
gagacgatgg acaggcagat ttc                                              23

<210> SEQ ID NO 82
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 82
accatcaacg tccccctgcg c                                                21

<210> SEQ ID NO 83
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 83
aatcgccttc tctgccacaa                                                  20

<210> SEQ ID NO 84
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 84
gtggtcgaag cggatggt                                                    18

<210> SEQ ID NO 85
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 85
cacctgcaaa gtccccggcc tc                                               22

<210> SEQ ID NO 86
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 86
tgacacgagc actggcaagt                                                  20

<210> SEQ ID NO 87
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 87
cgacgcgtgg tagacaaagt ag                                              22

<210> SEQ ID NO 88
<211> LENGTH: 102
<212> TYPE: DNA
<213> ORGANISM: Artificial Sequence
<220> FEATURE:
<223> OTHER INFORMATION: synthetic oligonucleotide

<400> SEQUENCE: 88
gcccccaagg gttgaaaggt gtgaaaggca atccgggcaa tatcagggac cagccgaggc     60
cagccttctc cgccattcgg cggaaccccc caatgggggg ca                       102

<210> SEQ ID NO 89
<211> LENGTH: 106
<212> TYPE: DNA
<213> ORGANISM: Artificial Sequence
<220> FEATURE:
<223> OTHER INFORMATION: synthetic oligonucleotide

<400> SEQUENCE: 89
gcattgagag ggaggcctaa gaataataac aatccagtgc ttaagagtca ggcgctgggt     60
agctgcccca cgttctgcca tctcctgcac tccctgttgc ggggcc                   106

<210> SEQ ID NO 90
<211> LENGTH: 105
<212> TYPE: DNA
<213> ORGANISM: Artificial Sequence
<220> FEATURE:
<223> OTHER INFORMATION: synthetic oligonucleotide

<400> SEQUENCE: 90
gggatccagg ccccaggggt cctcccgggg agccgggtga ggagggtcga tacaagcaga     60
aattccagtc agtgttcacg gtcactcggc agacccacca gcccc                    105

<210> SEQ ID NO 91
<211> LENGTH: 100
<212> TYPE: DNA
<213> ORGANISM: Artificial Sequence
<220> FEATURE:
<223> OTHER INFORMATION: synthetic oligonucleotide

<400> SEQUENCE: 91
tgaatttcgg atcttcaact ttgcatcagc catagctggg ctctggactc gaatggcagg     60
ctgggtccag cacccggacg cccgcctcgc tccctctgct                          100

<210> SEQ ID NO 92
<211> LENGTH: 104
<212> TYPE: DNA
<213> ORGANISM: Artificial Sequence
<220> FEATURE:
<223> OTHER INFORMATION: synthetic oligonucleotide

<400> SEQUENCE: 92
gcccccctgg accccgcggt cccaaaggtg actctggaga ctacaaggct acccagaaaa     60
tcgccttctc tgccacaaga accatcaacg tcccccctgcg ccgg                    104

<210> SEQ ID NO 93
<211> LENGTH: 101
<212> TYPE: DNA
<213> ORGANISM: Artificial Sequence

```
<220> FEATURE:
<223> OTHER INFORMATION: synthetic oligonucleotide

<400> SEQUENCE: 93
ctggcacacc agaagtgcca tgctcagaaa tgttggttac atgaatgaat gtcgagataa     60
cttcgtataa tgtatgctat acgaagttat atgcatgcca g                        101

<210> SEQ ID NO 94
<211> LENGTH: 132
<212> TYPE: DNA
<213> ORGANISM: Artificial Sequence
<220> FEATURE:
<223> OTHER INFORMATION: synthetic oligonucleotide

<400> SEQUENCE: 94
ggcggcctag ataacttcgt ataatgtatg ctatacgaag ttatgctagg taactataac    60
ggtcctaagg tagcgagcta gctcacgggg tcaaatcact cctatccaaa acctcctccc   120
tgccagtaat cc                                                       132
```